(12) United States Patent
Steff et al.

(10) Patent No.: US 11,571,472 B2
(45) Date of Patent: Feb. 7, 2023

(54) IMMUNOGENIC COMBINATIONS

(71) Applicant: GLAXOSMITHKLINE BIOLOGICALS SA, Rixensart (BE)

(72) Inventors: Ann-Muriel Steff, Laval (CA); Jean-Francois Toussaint, Rixensart (BE); Alessandra Vitelli, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/318,490

(22) PCT Filed: Jun. 12, 2015

(86) PCT No.: PCT/EP2015/063248
§ 371 (c)(1),
(2) Date: Dec. 13, 2016

(87) PCT Pub. No.: WO2015/189425
PCT Pub. Date: Dec. 17, 2015

(65) Prior Publication Data
US 2017/0143820 A1    May 25, 2017

Related U.S. Application Data

(60) Provisional application No. 62/011,712, filed on Jun. 13, 2014.

(51) Int. Cl.
| A61K 39/155 | (2006.01) |
| A61K 39/235 | (2006.01) |
| A61K 39/12  | (2006.01) |
| A61K 39/00  | (2006.01) |

(52) U.S. Cl.
CPC ............ *A61K 39/155* (2013.01); *A61K 39/12* (2013.01); *A61K 39/235* (2013.01); *A61K 2039/5256* (2013.01); *A61K 2039/545* (2013.01); *C12N 2710/10343* (2013.01); *C12N 2760/18534* (2013.01)

(58) Field of Classification Search
None
See application file for complete search history.

(56) References Cited

U.S. PATENT DOCUMENTS

| 6,180,398 | B1 | 1/2001 | Klein et al. |
| 6,511,845 | B1 | 1/2003 | Davis et al. |
| 7,514,087 | B2 | 4/2009 | McMichael et al. |
| 8,206,978 | B2 | 6/2012 | Lacoste et al. |
| 8,216,834 | B2 | 7/2012 | Colloca et al. |
| 8,398,993 | B2 | 3/2013 | Parra et al. |
| 8,563,002 | B2 | 10/2013 | Baudoux et al. |
| 9,095,546 | B2 | 8/2015 | Chow |
| 9,107,939 | B2 | 8/2015 | Luytjes et al. |
| 9,895,431 | B1 | 2/2018 | Reyes et al. |
| 2005/0214323 | A1 | 9/2005 | Chaplin et al. |
| 2009/0104232 | A1 | 4/2009 | Crystal et al. |
| 2010/0203071 | A1 | 8/2010 | Blais et al. |
| 2010/0272752 | A1 | 10/2010 | Spector et al. |
| 2011/0305727 | A1 | 12/2011 | Swanson et al. |
| 2012/0027788 | A1 | 2/2012 | Colloca et al. |
| 2012/0093847 | A1* | 4/2012 | Baudoux ............... A61K 39/12 424/186.1 |
| 2012/0141525 | A1 | 6/2012 | Jain et al. |
| 2012/0276138 | A1 | 11/2012 | Tang |
| 2014/0141037 | A1 | 5/2014 | Swanson et al. |
| 2014/0141042 | A1 | 5/2014 | Vitelli et al. |
| 2014/0147463 | A1 | 5/2014 | Radosevic |

FOREIGN PATENT DOCUMENTS

| WO | WO 98/02179 A1 | 1/1998 |
| WO | WO 2005/071093 A2 | 8/2005 |
| WO | 2008/107370 | 9/2008 |
| WO | WO 2008/114149 A2 | 9/2008 |
| WO | WO-2008107370 A1 * | 9/2008 ............ A61P 31/22 |
| WO | WO 2008/133663 A2 | 11/2008 |
| WO | WO 2009/025770 A2 | 2/2009 |
| WO | WO 2009/079796 A1 | 7/2009 |
| WO | WO 2010/009277 A2 | 1/2010 |
| WO | WO 2010/073043 A1 | 7/2010 |
| WO | WO 2010/086189 A2 | 8/2010 |
| WO | WO 2010/149745 A1 | 12/2010 |
| WO | WO 2011/008974 A2 | 1/2011 |
| WO | WO 2012/021730 A2 | 2/2012 |
| WO | WO 2012/085936 A2 | 6/2012 |

(Continued)

OTHER PUBLICATIONS

Swanson et al., PNAS Jun. 2011, 108 (23) 9619-9624.*
Connors et al., J of Virology vol. 65, No. 3, pp. 1634-1637, year 1991.*
Weisshaar et al. DNA and Cell Biology 2015, vol. 34, pp. 505-510.*
Murphy et al. Virus Research 1994 vol. 32, pp. 13-26.*
Rigter A, et al. (2013) A Protective and Safe Intranasal RSV Vaccine Based on a Recombinant Prefusion-Like Form of the F Protein Bound to Bacterium-Like Particles. PLoS ONE 8(8): e71072. (Year: 2013).*
Langley, et al., "A Randomized, Controlled, Observer-Blinded Phase 1 Study of the Safety a nd Immunogenicity of a Respiratory Syncytial Virus Vaccine With or Without Alum Adjuvant." The Journal of Infectious Diseases; 2017; vol. 215; pp. 24-33.

(Continued)

*Primary Examiner* — Shanon A. Foley
*Assistant Examiner* — Myron G Hill
(74) *Attorney, Agent, or Firm* — Birch, Stewart, Kolasch & Birch, LLP

(57) ABSTRACT

Immunogenic combinations that include a) an immunogenic component containing a peptide or polypeptide antigen of a respiratory pathogen; and b) an immunogenic component containing a nucleic acid encoding an antigen of the same respiratory pathogen, wherein the immunogenic components are formulated for concurrent administration are provided, as well as methods for making and for administering such immunogenic combinations to elicit an immune response specific for the respiratory pathogen.

13 Claims, 15 Drawing Sheets

Specification includes a Sequence Listing.

(56) References Cited

FOREIGN PATENT DOCUMENTS

| WO | WO 2012/089231 A1 | 7/2012 | |
|---|---|---|---|
| WO | WO 2012/089833 A2 | 7/2012 | |
| WO | WO-2012089833 A2 * | 7/2012 | ......... C07K 16/1027 |
| WO | WO 2012/158613 A1 | 11/2012 | |
| WO | 2013/006842 | 1/2013 | |
| WO | 2013/116965 | 8/2013 | |
| WO | WO 2013/139911 A1 | 9/2013 | |
| WO | 2014/079842 | 5/2014 | |

OTHER PUBLICATIONS

Beran, et al., "Safety and Immunogenicity of 3 Formulations of an Investigational Respiratory Syncytial Virus Vaccine in Nonpregnant Women: Results From 2 Phase 2 Trials." The Journal of Infectious Diseases; 2018; vol. 217; pp. 1616-1625.

Prince et al., Enhancement of respiratory syncytial virus pulmonary pathology in cotton rats by prior intramuscular inoculation of formalin-inactivated virus, Journal of Virology, 1986, p. 721-728, vol. 57, No. 3.

Hotard et al., Identification of residues in the human respiratory syncytial virus fusion protein that modulate fusion activity and pathogenesis, Journal of Virology, 2015, p. 512-522, vol. 89, No. 1.

Murphy et al., Immunization of cotton rats with the fusion (F) and large (G) glycoproteins of respiratory syncytial virus (RSV) protects against RSV challenge without potentiating RSV disease, Vaccine, 1989, p. 533-540, vol. 7.

McLellan, Jason, et al. "Structure-Based Design of a Fusion Glycoprotein Vaccine for Respiratory Syncytial Virus" Science, vol. 342, Nov. 1, 2013, corrected Sep. 18, 2014, pp. 592-598.

McLellan, Jason, et al., "Structure of RSV Fusion Glycoprotein Trimer Bound to a Prefusion-Specific Neutralizing Antibody" Science, vol. 340, May 31, 2013, pp. 1113-1117.

Extended European Search Report for European Application No. 21153269.2, dated Aug. 26, 2021.

Assignment of rights from the inventors to Okairos AG, dated Sep. 2-3, 2013.

Boxus etal., "DNA immunization with Plasmids Encoding Fusion and Nucieocapsid Proteins of Bovine Respiratory Syncytial Virus Induces a Strong Cell-Mediated immunity and Protects Calves against Challenge," Journal of Virology, vol. 81, No. 13, Jul. 2007, pp. 6873-6889.

Carine et al., "Vaccination of calves using the BRSV nucteocapsid protein in a DNA prime-protein boost strategy stimulates cell-mediated immunity and protects the lungs against BRSV replication and pathology," Vaccine, vol. 26, 2008, pp. 4840-4848.

Certified Copy of Priority Document for International Application No. PCT/EP2013/055335, dated April 9. 2013.

Colloca et al., "Generation and screening of a large collection of novel simian Adenovirus allows the identification of vaccine vectors inducing potent cellular immunity in humans: A range of novel simian adenoviral vectors, which are capable of priming high levels of T cell responses in man, has been defined," Science Translational Medicine, vol. 4, No. 115, 2012. pp. 1-24, 24 pages total.

Connors et al., "Respiratory Syncytial Virus (RSV) F, G, M2 (22K), and N Proteins Each Induce Resistance to RSV Challenge, but Resistance Induced by M2 and N Proteins Is Relatively Short-Lived," Journal of Virology, vol. 65, No. 3, March 1391, pp. 1634-1637.

Czub et al., "Evaluation of modified vaccinia virus Ankara based recombinant SARS vaccine In ferrets." Vaccine, vol. 23, 2005, pp. 2273-2279.

Ebata et al., "Function and immunogenicity of human parainfluenza virus 3 glycoproteins expressed by recombinant adenoviruses," Virus Research, vol. 24, 1932, pp. 21-33, 13 pages total.

European Statement of Opposition for European Patent No. EP2863841, dated May 24, 2022.

First Priority Application of Patent Application No. EP12160682.6, dated May 2, 2013.

Garlapati el al, "Enhanced immune responses and protection by vaccination with respiratory syncytial virus fusion protein formulated with CpG oligodeoxynucleotide and innate defense regulator peptide in polyphosphazene microparticles," Vaccine, vol. 30, 2012, pp. 5206-5214, 9 pages total.

Graham et al., "Biological Challenges and Technological Opportunities for Respiratory Syncytial Virus 'Vaccine Development," Immunological Reviews, vol. 233, No. 1, Jan. 2011, pp. 143-166.

Guan et al., "Effect of route of delivery on heterologous protection against HCV induced by an adenovirus vector carrying HCV structural genes," Virology Jouma!, vol. 8, No. 506, 2011, pp. 1-9.

Kohlmann et al., "Protective Efficacy and Immunogenicity of an Adenoviral Vector Vaccine Encoding the Codon-Optimized F Protein of Respiratory Syncytial Virus," Journal of Virology, 2009, pp. 12601-12610, 10 pages total.

Krause et al., "Absence of vaccine-enhanced RSV disease and changes in pulmonary dendritic cells with adenovirus-based RSV vaccine," Virology Journal, vol. 8, No. 375, 2011, pp. 1-12, 12 pages total.

Martinez et al., "Combining DNA and protein vaccines for early life immunization against respiratory syncytial virus in mice," European Journal of Immunology, vol. 23, 1399, pp. 3390-3400, 11 pages total.

PCT Request (Form PCT/RO/101) for international Application No. PCT/EP2012/063196, dated Jul. 5, 2012.

Roediger et al., "Heterologous Boosting of Recombinant Adenoviral Prime Immunization with a Novel Vesicular Stomatitis Virus-vectored Tuberculosis Vaccine." Molecular Therapy. vol. 16, No. 6, Jun. 2008 (Mar. 23, 20008), pp. 1161-1169. XP055800858.

Schulze et al., "A prime-boost vaccination protocol optimizes immune responses against the nucieocapsid protein of the SARS coronavirus," Vaccine, vol. 26, 2808, pp. 6678-6684.

Shaw et al., "The path to an RSV vaccine," Current Opinion in Virology, vol. 3, 2013, pp. 332-342.

Simoes el al., "Palivizumab Prophylaxis, Respiratory Syncylial Virus, and Subsequent Recurrent Wheezing," The Journal of Pediatrics, vol. 15, No. 1, Jul. 2007, pp. 34-41.

Tatsis et al., "Adenoviruses as Vaccine Vectors," Molecular Therapy, vol. 10, No. 4, 2004, pp. 616-629, 14 pages total.

Wyatt et al., "Priming and Boosting Immunity to Respiratory Syncytial Virus by Recombinant Replication-defective Vaccinia Virus MVA," Vaccine, vol. 18, No. 5-6, 2000 (Oct. 1, 1999), pp. 392-397, XP002316543.

Zeng et al., "Protective effect of a RSV subunit vaccine candidate G1F/M2 was enhanced by a HSP70-Like protein in mice," Biochemical and Biophysical Research Communications, vol. 377, 2008, pp. 495-499.

* cited by examiner

IMMUNOGENIC COMBINATIONS

This application is filed pursuant to 35 U.S.C. § 371 as a United States National Phase Application of International Patent Application Serial No. PCT/2015/063248 filed Jun. 12, 2015, which claims priority to U.S. Provisional Application No. 62/011,712 filed Jun. 13, 2014, and the entire contents of each of the foregoing applications are hereby incorporated by reference.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

This disclosure concerns the field of immunology. More particularly this disclosure relates to a method for eliciting an immune response to protect against respiratory pathogens.

Because the respiratory tract is in direct contact with the environment and is exposed to numerous airborne organisms, the respiratory tract is the most frequent site of infection by pathogenic organisms. Such infections can result in symptoms and disease ranging from the common cold, to bronchitis, bronchiolitis and pneumonia, as well as severe and chronic conditions. Common causal agents of respiratory infection include both viruses, such as rhinoviruses, coronaviruses, influenza virus, respiratory syncytial virus and other paramyxoviruses, adenovirus, and bacteria, such as *Streptococcus* sp., *Corynebacterium diptheriae, Bordatella pertussis, Haemophilus influenza*, and *Mycobacterium tuberculosis*.

Effective vaccines have been produced to protect children and adults from many of these respiratory pathogens. However, developing vaccines that are effective against other respiratory pathogens has proven challenging. Accordingly, new strategies for safe and effective vaccines that are effective against respiratory pathogens are necessary, especially to protect the very young, the elderly and other vulnerable individuals.

BRIEF SUMMARY

This disclosure concerns an immunogenic combination that includes a) an immunogenic component containing a peptide or polypeptide antigen of a respiratory pathogen; and b) an immunogenic component containing a nucleic acid encoding an antigen of the same respiratory pathogen, wherein the immunogenic components are formulated for concurrent, e.g., co-localized, administration. More specifically, the respiratory pathogen is respiratory syncytial virus (RSV). This disclosure also concerns the use of such immunogenic combinations, and methods for administering such immunogenic combinations to elicit an immune response specific for the respiratory pathogen.

DETAILED DESCRIPTION

Introduction

Figure 1:
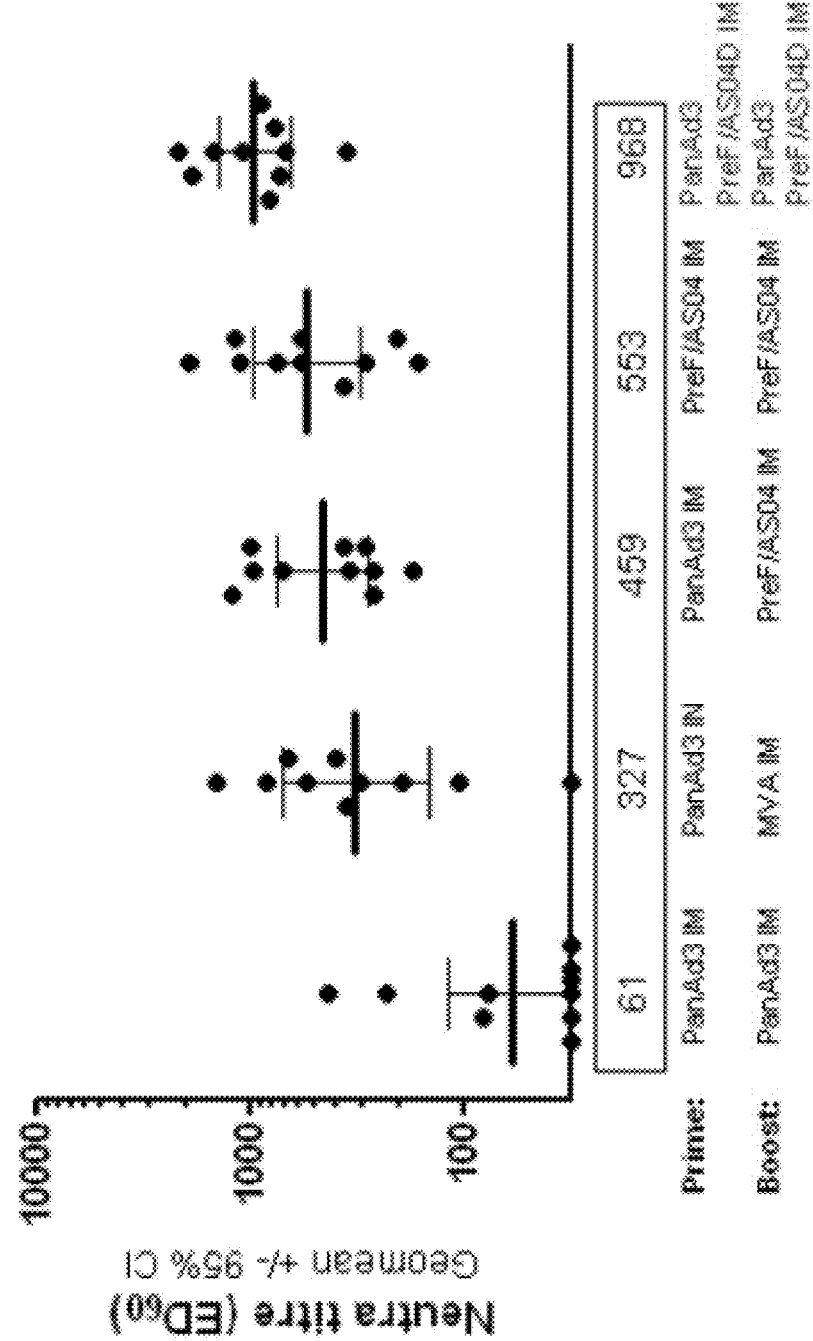
FIG. 1 is a graph illustrating RSV A neutralizing titre following immunization according to various regimens.

Developing safe and effective vaccines against certain respiratory pathogens has proven particularly challenging. The present disclosure concerns improved compositions and methods with increased immunogenic efficacy. More specifically, this disclosure provides immunogenic combinations for concurrent, and preferably co-localized administration, that elicit potent B and T cell responses, thereby enhancing immunogenicity, safety, and ultimately protection, against respiratory pathogens.

One aspect of the disclosure relates to an immunogenic combination comprising:

a) at least a first immunogenic component comprising a peptide or polypeptide antigen of a respiratory pathogen; and b) at least a second immunogenic component comprising a nucleic acid encoding an antigen of the same respiratory pathogen; in which the first immunogenic component and the second immunogenic component are formulated for concurrent administration.

In certain embodiments, the respiratory pathogen is a virus, such as a paramyxovirus. In one specific embodiment, the respiratory pathogen is Respiratory Syncytial Virus (RSV). In such an embodiment, the antigens can be selected from RSV antigens including the fusion protein (F), the attachment protein (G), the matrix protein (M2—which may include either or both of the M2-1(which may be written herein as M2.1) and M2-2 gene products) and the nucleoprotein (N). In a specific embodiment, the polypeptide antigen component contains a F protein antigen that is conformationally constrained in either a pre-fusion or a post-fusion conformation.

In certain embodiments of the immunogenic combination, the antigen of the first component and the antigen encoded by the nucleic acid of the second component share substantial sequence identity, such as about 70% sequence. In an exemplary embodiment, the immunogenic combination includes a first component that includes a polypeptide with the amino acid sequence represented by; and/or a second component that includes a nucleic acid that encodes a polypeptide with the amino acid sequence represented by:

a) a polypeptide comprising SEQ ID NO:2;

b) a polypeptide with at least 80% sequence identity to SEQ ID NO:2, which polypeptide comprises an amino acid sequence corresponding to the RSV F protein polypeptide of a naturally occurring RSV strain; or c) a polypeptide with at least 80% sequence identity to SEQ ID NO:2, which polypeptide comprises an amino acid sequence that does not correspond to a naturally occurring RSV strain.

In certain embodiments, the first immunogenic component contains and second immunogenic component encodes homologous antigens. Such homologous antigens may either be identical in sequence or non-identical in sequence. For example, the antigens can possess partially identical amino acid sequences. Favorably, such antigens include one or more identical or overlapping immunogenic epitopes.

For example, one exemplary immunogenic combination for eliciting an immune response specific for RSV comprises a first immunogenic component that contains a polypeptide of at least about 500 amino acids of an RSV F protein, the second immunogenic component contains a nucleic acid that encodes an identical or non-identical polypeptide (e.g., of at least about 500 amino acids of an RSV F protein). When non-identical, the RSV F protein polypeptides possess at least 80% sequence identity within the F1 and F2 domains. Favorably, the polypeptide of the first immunogenic component and or the polypeptide encoded by the second immunogenic component include or are an ectodomain of an RSV F Protein ($F_{TM}$).

In certain embodiments, the first immunogenic component and/or the second immunogenic components contain a plurality of antigens (e.g., of a respiratory pathogen, in particular of RSV).

As described above, the first immunogenic component contains a peptide or polypeptide (or fragment thereof) antigen of a respiratory pathogen. Such a peptide or polypeptide can optionally be in the form of a particle, such as a VLP or virosome, or a nanoscale biological particle.

Likewise, as described above, the second immunogenic component contains a nucleic acid that encodes an antigen of a respiratory pathogen. Both deoxy-ribonucleic acids and ribonucleic acids are suitable. Favorably, the nucleic acid is a nucleic acid other than a plasmid DNA. The nucleic acid can be included in a DNA or RNA vector, such as a replicable vector (e.g., a viral replicon, a self-amplifying nucleic acid), or in a virus (e.g., a live attenuated virus) or viral vector (e.g., replication proficient or replication deficient viral vector). Suitable viral vectors include but are not limited to an adenovirus, a modified vaccinia ankara virus (MVA), a paramyxovirus, a Newcastle disease virus, an alphavirus, a retrovirus, a lentivirus, an adeno-associated virus (AAV), a vesicular stomatitis virus, and a flavivirus. Optionally, the viral vector is replication defective.

In one embodiment, the first component contains an RSV F protein antigen, and the second component contains a nucleic acid that encodes an RSV F antigen and RSV, M and N antigens. More specifically, the first component contains an RSV F protein antigen conformationally constrained in the prefusion conformation, and the second component contains a nucleic acid that encodes an RSV FΔTM antigen and RSV M2-1 and N antigens, wherein a self-cleavage site is included between the RSV FΔTM antigen and the RSV M2-1 and a flexible linker is included between the RSV M2-1 and N antigens.

The first and second immunogenic components of the immunogenic combination can be formulated (for example, with a pharmaceutically acceptable buffer, carrier, excipient and/or adjuvant) in different compositions. Alternatively, the first and second immunogenic components can be co-formulated in a single composition for administration (either at the point of manufacturing, e.g., in a stable co-formulation suitable for storage, distribution, and administration, or at the point of delivery prior to administration). When the first and second immunogenic components are formulated in different compositions, they are favorably administered colocationally at or near the same site. For example, the first and second immunogenic components can be administered parentally by injection (e.g., via an administration route selected from intramuscular, transdermal, intradermal, subcutaneous) to the same side or extremity (co-lateral) administration). Alternatively, the first and second immunogenic components can be administered via mucosal, intranasal, oral, sublingual, or aerosol route or delivered to the lung in the form of a powder (particulate) or liquid.

In formulations containing an adjuvant, the adjuvant can include one or more of a metallic salt (Aluminum hydroxide, Aluminum phosphate, Aluminum potassium sulfate, aluminum hydroxyphosphate sulfate, Calcium hydroxide, Calcium fluoride, Calcium phosphate, Cerium(III) nitrate hexahydrate, Zinc sulfate heptahydrate), 3-D-monophosphoryl-lipid-A (MPL), a saponin, an oil and water emulsion, and/or a nanoparticle.

Another aspect of the present disclosure concerns use of the immunogenic combinations described above in medicine, e.g., for the prevention, reduction or treatment in a subject (such as a human subject, for example, a neonate, and infant, a child, an adolescent, an adult, e.g., a pregnant female or an elderly adult) of infection by or disease associated with a respiratory pathogen. Accordingly, also included are methods for eliciting an immune response specific for a pathogen by administering the immunogenic combinations described above. The administration can be in a vaccination regimen for the prevention, reduction or treatment of infection by or disease associated with a respiratory pathogen, such as a virus or bacterium that causes an infection of the upper and/or lower respiratory tract and/or the lungs. As disclosed above, in one particular embodiment, the use, method (or vaccination regimen) is for the prevention, reduction or treatment of infection by or disease associated with a paramyxovirus, such as Respiratory Syncytial Virus (RSV). In such a method, use or vaccination regimen, the first and second immunogenic components are administered concurrently (at or about the same time), and generally at or near the same location (e.g., co-laterally when administered by injection). When administered by injection, the first and second immunogenic components can be co-formulated, or individually formulated, in which case it is contemplated that the first and second immunogenic components are administered using a multi-chamber syringe or by a needle-free device, such as a transdermal patch.

In some embodiments, the method, use or vaccination regimen concurrently and/or co-locally administering the first and second immunogenic component elicits an immune response specific for the pathogen that is greater than the additive effect of an immune response elicited by the first immunogenic component and the second immunogenic component when administered or used separately. Favorably, administration of the immunogenic combinations disclosed herein elicits a humoral immune response, a cellular immune response or both a humoral immune response and a cellular immune response.

Also disclosed are kits containing the immunogenic combination described herein. Such kits also favorably include at least one device for administering the immunogenic combination, such as one or more pre-filled syringes, e.g., a multi-chambered syringe or a needle-free device, such as a transdermal patch.

Terms

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, are intended to be approximate. Thus, where a concentration is indicated to be at least (for example) 200 pg, it is intended that the concentration be understood to be at least approximately (or "about" or "~") 200 pg.

Although methods and materials similar or equivalent to those described herein can be used in the practice or testing of this disclosure, suitable methods and materials are described below. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of terms are provided. Additional terms and explanations can be provided in the context of this disclosure.

The term "immunogenic" when referring, e.g., to a composition, means that the composition is capable of eliciting a specific immune response, e.g., against a pathogen, such as a respiratory pathogen. An "immunogenic epitope" is a portion of an antigen to which a specific immune response (e.g., a B cell response and/or a T cell response) is directed, for example, via specific binding of a T cell receptor and/or antibody.

An "immunogenic composition" or "immunogenic component" is a composition suitable for administration to a human or animal subject (e.g., in an experimental setting) that is capable of eliciting a specific immune response. As such, an immunogenic composition includes one or more antigens (for example, a polypeptide antigen or nucleic acid that encode a polypeptide antigen) or antigenic epitopes. An immunogenic composition can also include one or more additional components capable of eliciting or enhancing an immune response, such as an excipient, carrier, and/or adjuvant. In certain instances, immunogenic compositions are administered to elicit an immune response that protects the subject against symptoms or conditions induced by a pathogen. In some cases, symptoms or disease caused by a pathogen is prevented (or reduced or ameliorated) by inhibiting replication of the pathogen (e.g., respiratory pathogen) following exposure of the subject to the pathogen. In the context of this disclosure, the term immunogenic composition will be understood to encompass compositions that are intended for administration to a subject or population of subjects for the purpose of eliciting a protective or palliative immune response against respiratory pathogens (that is, vaccine compositions or vaccines). In the context of the present disclosure an "immunogenic component" refers to an immunogenic composition that is preferentially used in combination with one or more additional immunogenic components or compositions. An "immunogenic combination" is an immunogenic composition that comprises or includes more than one (a plurality of) substituent "immunogenic components".

An "immune response" is a response of a cell of the immune system, such as, but not limited to, a B cell, T cell, NK cell, monocyte, dendritic cell, or polymorphonuclear cell to a stimulus. An immune response can be a B cell response, which results in the production of specific antibodies, such as antigen specific neutralizing antibodies. An immune response can also be a T cell response, such as a CD4+ response or a CD8+ response. In some cases, the response is specific for a particular antigen (that is, an "antigen-specific response"). If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or by a functional antibody response, by the reduction of signs or symptoms, or by measuring resistance to pathogen challenge in vivo.

An "antigen" is a compound, composition, or substance that can stimulate the production of antibodies and/or a T cell response in an animal, including compositions that are injected, absorbed or otherwise introduced into an animal (such as a human being). The term "antigen" includes all related antigenic epitopes. The term "epitope" or "antigenic determinant" refers to a site on an antigen to which B and/or T cells respond. The "dominant antigenic epitopes" or "dominant epitope" are those epitopes to which a functionally significant host immune response, e.g., an antibody response or a T-cell response, is made. In some cases, the host response to one or more dominant epitopes provides a protective immune response against a pathogen. The term "T-cell epitope" refers to an epitope that when bound to an appropriate MHC molecule is specifically bound by a T cell (via a T cell receptor). A "B-cell epitope" is an epitope that is specifically bound by an antibody (or B cell receptor molecule).

The term "polypeptide" refers to a polymer in which the monomers are amino acid residues which are joined together through amide bonds. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "fragment," in reference to a polypeptide, refers to a portion (that is, a subsequence) of a polypeptide. The term "immunogenic fragment" refers to all fragments of a polypeptide that retain at least one predominant immunogenic epitope of the full-length reference protein or polypeptide. The term "peptide" refers to a polymer of amino acids (joined through amide bonds), generally of less than 100 amino acids in length (e.g., of less than 50, or less than 40, or less than 30, or less than 25, or less than 20, or less than 15, or less than 10 amino acids in length). Orientation within a peptide or polypeptide is generally recited in an N-terminal to C-terminal direction, defined by the orientation of the amino and carboxy moieties of individual amino acids. Polypeptides are translated from the N or amino-terminus towards the C or carboxy-terminus.

The terms "nucleic acid" and "polynucleotide" refer to a polymeric form of nucleotides at least 10 bases in length. Nucleotides can be ribonucleotides, deoxyribonucleotides, or modified forms of either nucleotide. The term includes single and double, or positive and negative, forms of DNA or RNA. By "isolated" nucleic acid (or polynucleotide) is meant a nucleic acid (or polynucleotide that is not immediately contiguous with both of the coding sequences with which it is immediately contiguous (one on the 5' end and one on the 3' end) in the naturally occurring genome of the organism from which it is derived. In one embodiment, a polynucleotide encodes a polypeptide. The 5' and 3' direction of a nucleic acid is defined by reference to the connectivity of individual nucleotide units, and designated in accordance with the carbon positions of the deoxyribose (or ribose) sugar ring. The informational (coding) content of a nucleic acid sequence is read in a 5' to 3' direction.

In the context of a nucleic acid, the term "vector" refers to a nucleic acid that is capable of incorporating or carrying a nucleic acid obtained from a different source (an "insert") and replicating and/or expressing the inserted polynucleotide sequence, when introduced into a cell (e.g., a host cell). A nucleic acid vector can be either DNA or RNA. The term vector will be understood to include, e.g., plasmids, cosmids, phage, virus vectors, autonomously replicating viral nucleic acids, replicons, artificial chromosomes, and the like.

An "adjuvant" is an agent that enhances the production of an immune response in a non-specific manner. Common adjuvants include suspensions of minerals (alum, aluminum hydroxide, aluminum phosphate) onto which antigen is adsorbed; emulsions, including water-in-oil, and oil-in-water (and variants therof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components.

A "vaccination regimen" refers to a protocol (e.g., a sequence) of administrations of an immunogenic composition or combination of immunogenic compositions determined to elicit a desired immune response specific for an antigen (or plurality of antigens).

The term "concurrent" or "concurrently" means at or about the same time. Concurrent administration of an immunogenic combination means administration of two or more immunogenic components at or about the same time. In the context of a vaccination regimen, the term shall be understood to mean administration of two or more immunogenic components to elicit a kinetically associated immune response (e.g., a primary response, or a response that restimulates or boosts a secondary or memory response). Typically, concurrent administration with two or more immunogenic components (e.g., of an immunogenic combination) occurs between 0 and 10 days. Typically, concurrent administration occurs no longer than about 7 days apart, such as about 5 days, preferably no later than about 3 days, such as within 24 hours, such as within about 8 hours or less. Commonly, concurrent administration of two or more immunogenic components occurs within about 2 hours or less, such that the first and at least second immunogenic composition or component are administered within a period of 2 hours, a period of 1 hour, or within about 30 minutes, or about 10 minutes. In some instances, concurrent administration is performed at the same time, e.g., in one or more injections.

The term "co-administration" in relation to the administration to a subject of more than one immunogenic composition means administration of the one immunogenic compositions concurrently.

The term "colocationally" means that two compositions (for example., immunogenic compositions or immunogenic components of an immunogenic combination) are administered to the same (or about the same) location on the body of the recipient subject. The same location will be understood herein to mean to the same or approximately the same site or orifice. For example, in the case of mucosal administration, an immunogenic combination can be administered to the same orifice (e.g., the mouth or nose). In the case of parenteral administration, colocationally means in proximity at the same (or approximately the same) site on the body, such as to the same site (e.g., by the same device), or within about 10 cm, or more commonly within about 5 cm, such as within about 2 cm, or within 1 cm. In some instances, the two or more components are combined (co-formulated) in a single composition for administration to the same site. The term "co-lateral" or "co-laterally" in the case of parenteral administration means to the same side of the body in a grossly bilaterally symmetrical organism (such as a mammal, for example, a human or animal subject). The term co-lateral is contrasted with the term "contra-lateral", which refers to opposite sides of a grossly bilaterally symmetrical organism.

A "subject" is a living multi-cellular vertebrate organism. In the context of this disclosure, the subject can be an experimental subject, such as a non-human animal, e.g., a mouse, a cotton rat, or a non-human primate. Alternatively, the subject can be a human subject.

Immunogenic Combinations

This disclosure relates to immunogenic combinations capable of eliciting strong T-cell and B-cell responses, e.g., in naive subjects. The immunogenic combinations disclosed herein contain: a) at least a first immunogenic component comprising a peptide or polypeptide antigen; and b) at least a second immunogenic component comprising a nucleic acid encoding an antigen. The immunogenic components containing the peptide or polypeptide antigen and the nucleic acid that encodes an antigen are formulated for concurrent administration to a recipient. When concurrently administered, the first and second immunogenic components elicit a stronger or broader (e.g., more diverse and/or qualitatively more balanced) immune response than the additive response of each component when administered separately.

Although protective immune responses may be characterized as being predominantly either B cell (antibodies, for example, neutralizing antibodies), or T cell responses (e.g., a CD8+ T cell response), in some instances it is both desirable and advantageous to generate strong B cell and strong T cell responses specific for antigens (either the same or different) of a pathogen. Unfortunately, many vaccination regimens disproportionately elicit either a B cell or a T cell response without a protective increase in complementary response. This failure to elicit both B and T cell responses can be particularly important in protecting young infants, both due to the relative immaturity of the infant's immune system, and also due to the presence of maternal antibodies.

Typical vaccine regimens involve the repeated administration of an identical immunogenic composition (e.g., a vaccine). The first administration (designated for convenience a priming administration or "prime") induces proliferation and maturation of B and/or T cell precursors specific to one or more immunogenic epitopes present on the antigen (induction phase). The second (and in some cases subsequent) administration (designated for convenience a boosting administration or "boost"), further stimulates and potentially selects an anamnestic response of cells elicited by the prior administration(s). Thus, a bias towards either a B cell or a T cell immune response is amplified by subsequent administrations of the same immunogenic composition. In certain instances, the first administration is to a naive subject.

The present invention is predicated on the demonstration that concurrent administration of a protein (or peptide) antigen, as evidenced by pathogen specific neutralizing antibodies, with a nucleic acid that encodes an antigen of the same pathogen, is capable of eliciting B and T cell responses specific for the antigen and which exceed (both quantitatively and qualitatively) the cumulative response elicited by administering the two compositions separately and/or subsequently. Moreover, this combination can be achieved without immune interference, which is frequently observed with the combination of multiple (e.g., related) antigens. In some cases, immune interference diminishes the elicited immune response so significantly as to render combination vaccination counterproductive. Immune interference has previously been reported not only in the context of vaccines (e.g., combination vaccines) for respiratory pathogens, but also in the context of interference between maternally derived antibodies and vaccination of infants early in life (e.g., during the neonatal period through approximately 6 months of age).

As used above, "concurrent" or "simultaneous" administration refers to the same ongoing immune response. Preferably both compositions are administered at the same time (concurrent administration of both DNA+protein), however, one compound could be administered within a few minutes (for example, at the same medical appointment or doctor's visit), within a few hours, or within a few week's time (preferably 0-10 days) of the other (initial) administration and still be considered as "concurrent" since they both act during the same ongoing immune response.

Normally, when a polypeptide is administered, the immune response is considered immediate in that an immune response will initiate as soon as the antigen is exposed to the immune system. In contrast, when nucleic acid is administered, peak antigen expression (in vivo) is observed 3-7 days after administration, and thus antigen exposure to the immune system may be considered "delayed" when compared to the kinetics of protein vaccination. Regardless of this difference in kinetics, co-administration of nucleic acid and polypeptide can be considered "concurrent" by understanding that they are both functionally present during the process of an ongoing immune response. In order to present both immunogenic components (that is both as a polypeptide as such and polypeptide expressed by the administered nucleic acid), virtually simultaneously to the immune system, formulations can be conceived wherein the polypeptide is contained in such a way that its release from the formulation is delayed after the administration. This allows the expression of polypeptide from the polynucleotide to occur first, which is then subsequently complemented by the delayed released polypeptide from the formulation.

In one particular embodiment of the immunogenic combination disclosed herein involves the concurrent administration of both nucleic acid and protein where the protein (polypeptide) is present or administered in the form of delayed-release particles intended to hide the antigen from the immune system for a short period of time. Preferably such period is between 0-10 days. Typically, concurrent administration occurs at an interval of no greater than about 7 days apart, such as about 5 days, and more typically in an interval of no longer than about 3 days, such as within 24 hours, such as within about 8 hours or less. Commonly, concurrent administration of two or more immunogenic components occurs within about 2 hours or less, such that the first and at least second immunogenic composition or component are administered within a period of 2 hours, a period of 1 hour, or within about 30 minutes, or within about 20 minutes or about 10 minutes, or within about 5 minutes, or within about 2 minutes. In some instances, concurrent administration is performed at the same time, e.g., in one or more injections. It is envisioned that concurrent administration can be performed conveniently at a single medical appointment or doctor's visit.

Regardless of the different modes or possibilities of concurrent or simultaneous administration, as described above, it is important that both immunogenic components are present during the induction phase of an ongoing immune response. In comparison to this, the prime boost concept refers to 2 separate immune responses: (i) an initial priming of the immune system with a polynucleotide followed by (ii) a secondary or boosting of the immune system with a polypeptide many weeks or months after the primary immune response has been established.

The nucleic acid and protein components can thus be administered as two separate events or combined (admixed) to permit one administration. Preferably, the nucleic acid and protein components are admixed. Admixing can occur just prior to use, or when the two components are manufactured (and formulated), or any time in between.

The disclosed immunogenic combinations have been demonstrated to circumvent immune interference and exhibit superior or broader (e.g., more diverse and/or balanced) immunogenicity as compared to separate administration of either protein or nucleic acid based vaccines. The disclosed immunogenic combinations are particularly suitable for eliciting an immune response against a respiratory pathogen, particularly against RSV.

A respiratory pathogen is understood to mean a pathogen that infects cells of the upper (nasal cavity, pharynx and larynx) and/or lower (trachea, bronchi, lungs) respiratory tract, in severe cases causing bronchitis, bronchiolitis and/or pneumonia. Respiratory pathogens include both bacteria and viruses. Bacterial pathogens that infect the respiratory tract include, for example, *S. pneumoniae, N. meningitide*, as well as, *H. influenzae* and *M. catarrhalis*, which are involved in community acquired pneumonia (CAP) and acute exacerbation of chronic bronchitis (AECB). *C. diptheriae* is the causative agent of the upper respiratory tract infection, Diphtheria, while *B. pertussis* causes whooping cough or Pertussis. Other bacteria that cause respiratory tract infections include: *C. pneumoniae, M. pneumoniae* and *L. pneumophila*. Also included among the bacterial respiratory pathogens is *M. tuberculosis*, which causes (among other manifestation) pulmonary tuberculosis, *B. anthracis*, which when inhaled causes lethal respiratory tract infections, and *Y. pestis*, which is capable of causing pneumonic plague.

A broad range of viruses also infect and cause disease of the respiratory tract. Most predominantly, viral respiratory pathogens include members of the Orthomyxoviridae, for example, influenza virus and Paramyxoviridae, including Respiratory Syncytial Virus (RSV), the metapneumoviruses (e.g., human metapneumovirus, hMPV), parainfluenza viruses (PIV), as well as the viruses that cause measles (Morbillivirus), mumps (Rubulavirus), and Newcastle disease. Adenoviruses are also common respiratory pathogens. Although less frequent, certain coronaviruses (e.g., SARS virus) can cause severe respiratory disease. In addition, Rubivirus, a Togavirus, which causes Rubella, can lead to respiratory tract infections.

Thus, in the context of this disclosure, broadly speaking, both bacterial respiratory pathogens, and viral respiratory pathogens, are suitable targets for the immunogenic combinations and methods herein described. In certain embodiments, the respiratory pathogen is selected to be a bacterium. In an immunogenic combination (as described herein) to prevent or reduce (or to treat) infection or disease caused by a bacterial respiratory pathogen, the immunogenic compositions incorporate antigens selected from a bacterium, such as an antigen selected from: *S. pneumoniae, N. meningitide, H. influenza, M. catarrhalis, C. diptheriae, B. pertussis, C. pneumoniae, M. pneumoniae, L. pneumophila, M. tuberculosis, B. anthracis*, and *Y. pestis*.

In embodiments of the immunogenic combination to prevent or reduce (or to treat) infection or disease caused by a viral respiratory pathogen, the immunogenic compositions incorporate antigens selected from a virus, such as an antigen selected from: an Orthomyxovirus, such as influenza virus, a Paramyxovirus, such Respiratory Syncytial Virus (RSV), a metapneumovirus, a parainfluenza virus (PIV), measles virus (Morbillivirus), mumps virus (Rubulavirus), Newcastle disease virus, an Adenovirus, a coronaviruses (such as SARS virus), a Rubivirus and a Togavirus.

Thus, in certain embodiments, the respiratory pathogen can be an influenza virus, and the protein (or peptide) antigen and the antigen encoded by the nucleic acid are antigens of influenza virus. Suitable influenza virus antigens include: hemagglutinin (HA), neuraminidase (NA), nucleoprotein (NP) and matrix (M) proteins. In a specific embodiment, the antigens are selected to include homologous antigens. That is, both the polypeptide antigen and the antigen encoded by the nucleic acid are both selected to be an HA antigen, an NA antigen, an NP antigen and/or an M antigen. In such a case, the HA, NA, NP and/or M antigens can be identical, or non-identical. If non-identical, the two antigens can nonetheless include one or more than one homologous epitope that is identical in sequence. Alternatively, if non-identical, the two antigens can include one or more than one homologous epitope selected from different serotypes of influenza.

In certain preferred embodiments illustrated in the examples, the respiratory pathogen is a virus other than influenza, such as a Paramyxovirus (e.g., RSV, hMPV or PIV). Accordingly, such an immunogenic combination includes antigens of a Paramyxovirus. In one particular embodiment, the combination is selected to include antigens of RSV.

As indicated above, Respiratory syncytial virus (RSV) is a pathogenic virus of the family Paramyxoviridae. Suitable antigens of RSV in the context of the immunogenic combinations disclosed herein can be selected from: the fusion protein (F), the attachment protein (G), the matrix protein (M2) and the nucleoprotein (N).

The term "F protein" or "Fusion protein" or "F protein polypeptide" or "Fusion protein polypeptide" refers to a polypeptide or protein having all or part of an amino acid sequence of an RSV Fusion protein polypeptide. Similarly, the term "G protein" or "G protein polypeptide" refers to a polypeptide or protein having all or part of an amino acid sequence of an RSV Attachment protein polypeptide. The term "M protein" or "matrix protein" or "M protein polypeptide" refers to a polypeptide or protein having all or part of an amino acid sequence of an RSV Matrix protein. Likewise, the term "N protein" or "Nucleocapsid protein" or "N protein polypeptide" refers to a polypeptide or protein having all or part of an amino acid sequence of an RSV Nucleoprotein.

Two groups of human RSV strains have been described, the A and B groups, based mainly on differences in the antigenicity of the G glycoprotein. Numerous strains of RSV have been isolated to date, any of which are suitable in the context of the antigens of the immunogenic combinations disclosed herein. Exemplary strains indicated by GenBank and/or EMBL Accession number can be found in US published application number 2010/0203071 (WO2008114149), which is incorporated herein by reference for the purpose of disclosing the nucleic acid and polypeptide sequences of RSV F and G proteins suitable for use in the disclosed immunogenic combinations.

Exemplary M and N protein nucleic acids and protein sequences can be found, e.g., in US published application number 2014/0141042 (WO2012/089833), which are incorporated herein for purpose of disclosing the nucleic acid and polypeptide sequences of RSV M and N proteins suitable for use in the disclosed immunogenic combinations.

Additional strains (and their F, G, M and N protein antigens) of RSV are likely to be isolated, and are encompassed within the genus of RSV antigens. Similarly, the genus of RSV encompasses variants arising from naturally occurring (e.g., previously or subsequently identified strains) by genetic drift, or artificial synthesis and/or recombination. Sequences of documented RSV strain genomes and their substituent nucleic acids and the proteins encoded thereby (particularly F, G, M and N proteins) can readily be determined by those of ordinary skill in the art by searching GenBank (on the world wide web (http://www) at ncbi.nlm.nih.gov/genbank).

In certain favorable embodiments, the polypeptide antigen is an F protein polypeptide antigen. Particularly suitable as a polypeptide antigen component in the context of the immunogenic combinations disclosed herein are conformationally constrained F polypeptide antigens. Conformationally constrained F proteins have previously been described in both the prefusion (PreF) and postfusion (PostF) conformations. Such conformationally constrained F proteins typically comprise an engineered RSV F protein ectodomain. An F protein ectodomain polypeptide is a portion of the RSV F protein that includes all or a portion of the extracellular domain of the RSV F protein and lacks a functional (e.g., by deletion or substitution) transmembrane domain, which can be expressed, e.g., in soluble (not attached to a membrane) form in cell culture.

Exemplary F protein antigens conformationally constrained in the prefusion conformation have been described in the art and are disclosed in detail in e.g., U.S. Pat. No. 8,563,002 (WO2009079796); US Published patent application No. US2012/0093847 (WO2010/149745); US2011/0305727 (WO2011/008974); US2014/0141037 and WO2012158613, each of which is incorporated herein by reference for the purpose of illustrating prefusion F polypeptides (and nucleic acids), and methods of their production. Typically, the antigen is in the form of a trimer of polypeptides. Additional publications providing examples of F proteins in the prefusion conformation include: McLellan et al., Science, Vol. 340: 1113-1117; McLellan et al., Science, Vol 342: 592-598, and Rigter et al., PLOS One, Vol. 8: e71072, each of which can also be used in the context of the immunogenic combinations disclosed herein. Likewise, F protein antigens conformationally constrained in the postfusion conformation are also well known in the art and can be used in the context of the immunogenic combinations disclosed herein. Typically, the antigen is in the form of a timer of polypeptides. Examples of postfusion conformationally constrained F protein polypeptides are disclosed in detain in, e.g., US2011/0305727 (WO2011/008974), and Swanson et al., PNAS, Vol. 108:9619-9624, each of which is incorporated herein by reference for the purpose of illustrating postfusion F polypeptides and nucleic acids and methods of their production.

For example, an F protein polypeptide stabilized in the prefusion conformation typically includes an ectodomain of an F protein (e.g., a soluble F protein polypeptide) comprising at least one modification that stabilized the prefusion conformation of the F protein. For example, the modification can be selected from an addition of a trimerization domain (typically to the C terminal end), deletion of one or more of the furin cleavage sites (at amino acids ~105-109 and ~133-136), a deletion of the pep27 domain, substitution or addition of a hydrophilic amino acid in a hydrophobic domain (e.g., HRA and/or HRB). In an embodiment, the conformationally constrained PreF antigen comprises an F2 domain (e.g., amino acids 1-105) and an F1 domain (e.g., amino acids 137-516) of an RSV F protein polypeptide with no intervening furin cleavage site wherein the polypeptide further comprises a heterologous trimerization domain positioned C-terminal to the F1 domain. Optionally, the PreF antigen also comprises a modification that alters glycosylation (e.g., increases glycosylation), such as a substitution of one or more amino acids at positions corresponding to amino acids ~500-502 of an RSV F protein. Additionally or alternatively, the F polypeptide conformationally constrained in the prefusion conformation can include at least two introduced cysteine residues, which are in close proximity to one another and form a disulfide bond that stabilizes the pre-fusion RSV F polypeptide. For example, the two cysteines can be within about 10 Å of each other. For example, cysteines can be introduced at positions 165 and 296. An exemplary PreF antigen is represented by SEQ ID NO:2.

In other embodiments, conformationally constrained F antigens can include one or more modifications selected from: 1) one or more modifications (e.g., mutations) to one or both furin-cleavage sites, 2) one or more modifications to the fusion peptide, 3) one or more modifications to the p27 linker, 4) an added oligomerization sequence; and/or an added sequence that provides a protease cleavage site.

In an embodiment, the F antigen comprises three RSV F ectodomain polypeptides each comprising an endogenous HRA region and optionally an endogenous HRB region, and at least one oligomerization polypeptide, wherein the three ectodomain polypeptides and the at least one oligomerization polypeptide form a six-helix bundle, with the proviso that the endogenous HRA, regions of the RSV F polypeptides are not part of the six-helix bundle. The trimer can be characterized in that the six-helix bundle is formed with the inclusion of the HRB regions.

In one specific favorable embodiment, described in detail in the Examples, the F protein polypeptide is a protein with an amino acid sequence selected from the group of: a) a polypeptide comprising SEQ ID NO:2; b) a polypeptide with at least 80% sequence identity to SEQ ID NO:2, which polypeptide comprises an amino acid sequence corresponding to the RSV F protein polypeptide of a naturally occurring RSV strain; and c) a polypeptide with at least 95% sequence identity to SEQ ID NO:2, which polypeptide comprises an amino acid sequence that does not correspond to a naturally occurring RSV strain.

Methods of determining sequence identity are well known in the art, and are applicable to the foregoing antigen polypeptides, as well as the nucleic acids that encode them (e.g., as described below). Various programs and alignment algorithms are described in: Smith and Waterman, Adv. Appl. Math. 2:482, 1981; Needleman and Wunsch, J. Mol. Biol. 48:443, 1970; Higgins and Sharp, Gene 73:237, 1988; Higgins and Sharp, CABIOS 5:151, 1989; Corpet et al., Nucleic Acids Research 16:10881, 1988; and Pearson and Lipman, Proc. Natl. Acad. Sci. USA 85:2444, 1988. Altschul et al., Nature Genet. 6:119, 1994, presents a detailed consideration of sequence alignment methods and homology calculations. The NCBI Basic Local Alignment Search Tool (BLAST) (Altschul et al., J. Mol. Biol. 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

In some instances, the selected antigen has one or more amino acid modification relative to the amino acid sequence of the naturally occurring strain from which it is derived (e.g., such as the modifications that stabilize a prefusion or postfusion conformation). Such differences can be an addition, deletion or substitution of one or more amino acids. A variant typically differs by no more than about 1%, or 2%, or 5%, or 10%, or 15%, or 20% of the amino acid residues. For example, a variant antigen polypeptide sequence can include 1, or 2, or up to 5, or up to about 10, or up to about 15, or up to about 50, or up to about 100 amino acid differences as compared to the reference polypeptide, such as the reference F antigen polypeptide sequences of SEQ ID NO:2. Thus, a variant in the context of an RSV F protein antigen typically shares at least 80%, or 85%, more commonly, at least about 90% or more, such as 95%, or even 98% or 99% sequence identity with a reference protein, e.g., the reference sequences illustrated in SEQ ID NO:2, and includes any of the exemplary PreF and/or PostF antigens disclosed herein (e.g., by reference to U.S. Pat. No. 8,563002 (WO2009079796); US Published patent application No. US2012/0093847 (WO2010/149745); US2011/ 0305727 (WO2011/008974); US2014/0141037; WO2012158613; McLellan et al., Science, Vol. 340: 1113-1117; McLellan et al., Science, Vol 342: 592-598; Rigter et al., PLOS One, Vol. 8: e71072; US2011/0305727 (WO2011/ 008974), and Swanson et al., PNAS, Vol. 108:9619-9624.

Additional variants included as a feature of this disclosure are F antigens (including PreF and PostF antigens) that include all or part of a nucleotide or amino acid sequence selected from the naturally occurring variants disclosed in US published application number 2010/0203071 (WO2008114149). Additional variants can arise through genetic drift, or can be produced artificially using site directed or random mutagenesis, or by recombination of two or more preexisting variants. Such additional variants are also suitable in the context of the F antigens disclosed herein. For example, the modification can be a substitution of one or more amino acids (such as two amino acids, three amino acids, four amino acids, five amino acids, up to about ten amino acids, or more) that do not alter the conformation or immunogenic epitopes of the resulting F (e.g., PreF or PostF) antigen.

Alternatively or additionally, the modification can include a deletion of one or more amino acids and/or an addition of one or more amino acids. Indeed, if desired, one or more of the polypeptide domains can be a synthetic polypeptide that does not correspond to any single strain, but includes component subsequences from multiple strains, or even from a consensus sequence deduced by aligning multiple strains of RSV virus polypeptides. For examples of consensus RSV F (as well as M and N) protein antigens, see, US 2014/0141042 (WO 2012/089833), which is incorporated herein by reference for the teaching of the design of exemplary F, M and N consensus sequence polypeptide antigens.

In certain embodiments, one or more of the polypeptide domains is modified by the addition of an amino acid sequence that constitutes a tag, which facilitates subsequent processing or purification. Such a tag can be an antigenic or epitope tag, an enzymatic tag or a polyhistidine tag. Typically the tag is situated at one or the other end of the protein, such as at the C-terminus or N-terminus of the antigen or fusion protein.

In addition to a polypeptide or peptide antigen, the immunogenic combinations disclosed herein also include a second immunogenic component that contains a nucleic acid that encodes an antigen of the same respiratory pathogen (as the peptide or polypeptide antigen contained in the first immunogenic component). It is contemplated that the nucleic acid is a nucleic acid other than a plasmid DNA. The nucleic acid can be in the form of a replicating or replication defective vector, such as a viral vector. Numerous viral vectors suitable for introducing immunogenic nucleic acids into a subject are known in the art, and include both DNA and RNA viruses. Suitable examples for encoding an antigen in the context of the immunogenic combinations disclosed herein include, for example: adenovirus vectors (replicating or replication deficient), pox virus vectors, including vaccinia virus vectors, such as modified vaccinia Ankara virus (MVA), NYVAC, avipox vectors, canarypox (ALVAC) and fowl pox virus (FPV), Alphavirus vectors (such as Sindbis virus, Semlike Forest virus (SFV), Ross River virus, and Venezuelan equine encephalitis (VEE) virus) and chimeras and replicons thereof, herpes virus vectors (e.g., cytomegalovirus (CMV)-derived vectors), arena virus vectors, such as lymphocytic choriomeningitis virus (LCMV) vectors, measles virus vectors, vesicular stomatitis virus vectors, pseudorabies virus, adeno-associated virus, retrovirus, lentivirus, viral like particles, and many others.

In one particular embodiment, the vector is an adenovirus. The production and use of Adenovirus vectors are well known to those of ordinary skill in the art. In the context of the immunogenic combinations disclosed here, examples of disclosure of the design, production and use of adenovirus vectors containing antigens of a respiratory pathogen can be found in, e.g., US published application no. US2014/ 0141042 (WO 2012/089833). Additional detail concerning the adenovirus vectors is found, e.g., in U.S. Pat. No. 8,216,834 (WO 2005/071093); and US published application no. US2012/0027788 (WO 2010/086189); US published application no. US20050214323.

Adenoviral vectors of use in the present invention may be derived from a range of mammalian hosts.

Over 100 distinct serotypes of adenovirus have been isolated which infect various mammalian species, 51 of which are of human origin. Thus one or more of the adenoviral vectors may be derived from a human adenovirus. Examples of such human-derived adenoviruses are Ad1, Ad2, Ad4, Ad5, Ad6, Ad11, Ad 24, Ad34, Ad35, particularly Ad5, Ad11 and Ad35. The human and nonhuman adenviral serotypes have been categorised into six subgenera (A-F) based on a number of biological, chemical, immunological and structural criteria.

Although Ad5-based vectors have been used extensively in a number of gene therapy trials, there may be limitations on the use of Ad5 and other human group C adenoviral vectors due to preexisting immunity in the general population due to natural infection. Ad5 and other human group C members tend to be among the most seroprevalent serotypes. Immunity to existing vectors may develop as a result of exposure to the vector during treatment. These types of preexisting or developed immunity to seroprevalent vectors may limit the effectiveness of gene therapy or vaccination efforts. Alternative adenovirus serotypes, thus constitute very important targets in the pursuit of gene delivery systems capable of evading the host immune response.

One such area of alternative serotypes are those derived from non human primates, especially adenoviruses isolated from chimpanzee, bonobos and gorillas. See U.S. Pat. No. 6,083,716 which describes the genome of two chimpanzee adenoviruses.

It has been shown that nonhuman simian adenoviral vectors induce strong immune responses to transgene products as efficiently as human adenoviral vectors (Fitzgerald et al. J. Immunol. 170:1416; (Colloca et al. (2012) Science-Translational Medicine 4:1-9; Roy et al. (2004) Virology 324: 361-372; Roy et al. (2010) Journal of Gene Medicine 13:17-25).

Non human primate adenoviruses can be isolated from the mesenteric lymph nodes or feces of the animals and can replicate in vitro in HEK 293 cells. Despite these similarities, nonhuman simian adenoviruses are phylogenetically and immunologically distinct from the more common human serotypes (Ad2 and Ad5).

Thus one or more of the adenoviral vectors may be derived from a non-human primate adenovirus eg a chimpanzee adenovirus such as one selected from serotypes ChAd3, ChAd63, ChAd83, ChAd155, Pan5, Pan6, Pan7 and Pan9. Specifically, the virus may be a non-human adenovirus, such as a simian adenovirus and in particular a chimpanzee adenovirus such as ChAd155, Pan 5, 6, 7 or 9. Examples of such strains are described in WO03/000283 and are available from the American Type Culture Collection, 10801 University Boulevard, Manassas, Va. 20110-2209, and other sources. Desirable chimpanzee adenovirus strains include Pan 5 [ATCC VR-591], Pan 6 [ATCC VR-592], and Pan 7 [ATCC VR-593]. Alternatively, adenoviral vectors may be derived from nonhuman simian adenoviruses derived from bonobos, such as PanAd1, PanAd2 or PanAd3. Examples of such vectors described herein can be found for example in WO2005/071093, WO2010/086189 and GB1510357.5.

Use of nonhuman simian adenoviruses is thought to be advantageous over use of human adenovirus serotypes because of the lack of pre-existing immunity, in particular the lack of cross-neutralising antibodies, to adenoviruses in the target population. Cross-reaction of the chimpanzee adenoviruses with pre-existing neutralizing antibody responses is only present in 2% of the target population compared with 35% in the case of certain candidate human adenovirus vectors. The chimpanzee adenoviruses are distinct from the more common human subtypes Ad2 and Ad5, but are more closely related to human Ad4 of subgroup E, which is not a prevalent subtype. Pan 6 is less closely related to Pan 5, 7 and 9.

The adenovirus of the invention may be replication defective. This means that it has a reduced ability to replicate in non-complementing cells, compared to the wild type virus. This may be brought about by mutating the virus e.g. by deleting a gene involved in replication, for example deletion of the E1a, E1b, E3 or E4 gene.

The adenoviral vectors in accordance with the present invention may be derived from replication defective adenovirus comprising a functional E1 deletion. Thus the adenoviral vectors according to the invention may be replication defective due to the absence of the ability to express adenoviral E1a and E1b, i.e., are functionally deleted in E1a and E1b. The recombinant adenoviruses may also bear functional deletions in other genes [see WO 03/000283] for example, deletions in E3 or E4 genes. The adenovirus delayed early gene E3 may be eliminated from the adenovirus sequence which forms part of the recombinant virus. The function of E3 is not necessary to the production of the recombinant adenovirus particle. Thus, it is unnecessary to replace the function of this gene product in order to package a recombinant adenovirus useful in the invention. In one particular embodiment the recombinant adenoviruses have functionally deleted E1 and E3 genes. The construction of such vectors is described in Roy et al., Human Gene Therapy 15:519-530, 2004.

Recombinant adenoviruses may also be constructed having a functional deletion of the E4 gene, although it may be desirable to retain the E4 ORF6 function. Adenovirus vectors according to the invention may also contain a deletion in the delayed early gene E2a. Deletions may also be made in any of the late genes L1 through to L5 of the adenovirus genome. Similarly deletions in the intermediate genes IX and IVa may be useful.

Other deletions may be made in the other structural or non-structural adenovirus genes. The above deletions may be used individually, i.e. an adenovirus sequence for use in the present invention may contain deletions of E1 only. Alternatively, deletions of entire genes or portions thereof effective to destroy their biological activity may be used in any combination. For example in one exemplary vector, the adenovirus sequences may have deletions of the E1 genes and the E4 gene, or of the E1, E2a and E3 genes, or of the E1 and E3 genes (such as functional deletions in E1a and E1b, and a deletion of at least part of E3), or of the E1, E2a and E4 genes, with or without deletion of E3 and so on. Such deletions may be partial or full deletions of these genes and may be used in combination with other mutations, such as temperature sensitive mutations to achieve a desired result. Adenoviral vectors of use in the present invention include PanAd3 (WO 2010/086189) and ChAd155 (GB1510357.5).

The adenoviral vectors can be produced on any suitable cell line in which the virus is capable of replication. In particular, complementing cell lines which provide the factors missing from the viral vector that result in its impaired replication characteristics (such as E1 and/or E4) can be used. Without limitation, such a cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources, such as PER.C6© cells, as represented by the cells deposited under ECACC no. 96022940 at the European Collection of Animal Cell Cultures (ECACC) at the Centre for Applied Microbiology and Research (CAMR, UK) or Her 96 cells (Crucell).

In another embodiment, the viral vector is a pox virus vector. In favorable embodiments the pox virus is selected from the group of: U.S. Pat. No. 6,761,893 (WO02/42480); U.S. Pat. Nos. 7,964,395; 7,964,396; US published application no. US2013/0183335 (WO2012/048817); and PCT published application no. WO2014/019718 provide exemplary vectors and methods for the production of MVA vectors suitable in the context of an immunogenic component as disclosed herein. Each of the preceding is incorporated herein by reference for the teaching of suitable MVA vectors and methods.

In another embodiment, the viral vector is an Alphavirus vector, such as an alphavirus replicon or other self-replicating RNA vector. Exemplary alphavirus vectors and methods for producing and delivering them suitable for use in the context of the immunogenic combinations disclosed herein are described in, e.g., US20090104226 (WO2006078294); US20110300205 (WO2011005799); US20130195968 (WO 2012/006376); US20130177639 (WO2012006377); WO2013006838; and WO2013006842, each of which are incorporated herein for their disclosure of exemplary self-replicating RNA vectors suitable in the context of the disclosed immunogenic combinations.

In the context of the immunogenic combinations disclosed herein, the polypeptide antigen of the respiratory pathogen, and the antigen of the same pathogen encoded by a nucleic acid can be the same or different. Favorably, in the context of the immunogenic combinations disclosed herein the two immunogenic components are homologous (that is related by descent from a common evolutionary precursor), and thus share at least partial sequence identity (as determined above). In some embodiments, the first immunogenic component and the antigen(s) encoded by the second immunogenic component of the immunogenic combination include at least one identical or homologous antigen. In certain embodiments, the antigens are non-identical, in which case, the antigens can comprise partially identical amino acid sequences, for example, such that they include at least one identical or partially identical immunogenic epitope. Partially identical epitopes can be, for example, selected from a corresponding portion of a homologous antigen of another strain or serotype of the pathogen.

In certain embodiments of the immunogenic combination, the antigen of the first component and the antigen encoded by the nucleic acid of the second component share substantial sequence identity, such as about 70% sequence identity across all or a portion of their length, for example, about 75% identity, about 80% identity, about 85% identity, about 90% identity or about or greater than 95% identity. In an embodiment in which one component includes (or encodes) one antigen, and the other component includes (or encodes) multiple antigens, the sequence identity is compared between the corresponding antigens. To illustrate, in an embodiment in which the first component contains an RSV F protein antigen, and the second component contains a nucleic acid that encodes an RSV F antigen and RSV, M and N antigens, the sequence identity is compared between the F proteins (without regard to the M and N protein components). Where multiple antigens are included in each component, at least one is expected to meet the threshold of 70% sequence identity.

For example, in one favorable embodiment to elicit an immune response specific for RSV, the immunogenic combination includes a first immunogenic component that contains an RSV F protein antigen. The second immunogenic component contains a nucleic acid that encodes an RSV F protein. In an embodiment, one or both of the immunogenic components can be an ectodomain of an RSV F Protein (FΔTM). In an embodiment, the antigens are identical. In another embodiment, the F protein antigens are non-identical in sequence. For example, in one exemplary embodiment described in more detail below, the first immunogenic component includes a polypeptide antigen that is a conformationally constrained F protein antigen, and the second immunogenic component includes a nucleic acid (for example, and adenovirus vector) that encodes an F protein polypeptide of a different sequence that is not conformationally constrained, e.g., a consensus sequence F protein polypeptide designed as described in US2012/0027788. In one embodiment, the first component contains an RSV F protein antigen, and the second component contains a nucleic acid that encodes an RSV F antigen and RSV, M and N antigens. More specifically, the first component contains an RSV F protein antigen conformationally constrained in the prefusion conformation, and the second component contains a nucleic acid that encodes an RSV FΔTM antigen and RSV M2-1 and N antigens, wherein a self-cleavage site is included between the RSV FΔTM antigen and the RSV M2-1 and a flexible linker is included between the RSV M2-1 and N antigens. More specifically, the first component may contain an RSV F protein antigen represented by SEQ ID NO:2, and the second component may contain an adenoviral vector carrying a nucleic acid insert represented by SEQ ID NO:3.

Optionally, one or both of the immunogenic components includes a plurality of antigens. Typically, these are selected from the same target pathogen. However, embodiments are contemplated in which antigens of multiple pathogens are included in the immunogenic combination.

Immunogenic Components and Combinations

In the context of the immunogenic combinations disclosed herein, the immunogenic components comprising (nucleic acid and protein) can be formulated for administration in a single immunogenic composition or in different immunogenic compositions. When formulated for administration in a single composition the components can be admixed prior to administration or stably co-formulated during manufacture.

The immunogenic compositions disclosed herein typically contain a pharmaceutically acceptable carrier or excipients. Pharmaceutically acceptable carriers and excipients are well known and can be selected by those of skill in the art. The adjective "pharmaceutically acceptable" indicates that the referent is suitable for administration to a subject (e.g., a human or animal subject). Remington's Pharmaceutical Sciences, by E. W. Martin, Mack Publishing Co., Easton, Pa., 15th Edition (1975), describes compositions and formulations (including diluents) suitable for pharmaceutical delivery of therapeutic and/or prophylactic compositions, including immunogenic compositions.

For example, in the context of the immunogenic components and combinations disclosed herein, the carrier or excipient can favorably include a buffer. Optionally, the carrier or excipient also contains at least one component that stabilizes solubility and/or stability. Examples of solubilizing/stabilizing agents include detergents, for example, laurel sarcosine and/or tween. Alternative solubilizing/stabilizing agents include arginine, and glass forming polyols (such as sucrose, trehalose and the like). Numerous pharmaceutically acceptable carriers and/or pharmaceutically acceptable excipients are known in the art and are described, e.g., in Remington's Pharmaceutical Sciences, by E. W. Martin, Mack Publishing Co., Easton, Pa., 5th Edition (975).

Accordingly, suitable excipients and carriers can be selected by those of skill in the art to produce a formulation suitable for delivery to a subject by a selected route of administration.

Suitable excipients include, without limitation: glycerol, Polyethylene glycol (PEG), Sorbitol, Trehalose, N-lauroyl-sarcosine sodium salt, L-proline, Non detergent sulfobetaine, Guanidine hydrochloride, Urea, Trimethylamine oxide, KCl, Ca2+, Mg2+, Mn2+, Zn2+ and other divalent cation related salts, Dithiothreitol, Dithioerytrol, and β-mercaptoethanol. Other excipients can be detergents (including: Tween80, Tween20, Triton X-00, NP-40, Empigen BB, Octylglucoside, Lauroyl maltoside, Zwittergent 3-08, Zwittergent 3-0, Zwittergent 3-2, Zwittergent 3-4, Zwittergent 3-6, CHAPS, Sodium deoxycholate, Sodium dodecyl sulphate, Cetyltrimethylammonium bromide).

Optionally, the disclosed immunogenic combinations also include an adjuvant, which adjuvant also may be used with the disclosed vaccine regimens, methods, uses and kits. In certain embodiments, the immunogenic component containing the polypeptide antigen of a respiratory pathogen is formulated with an adjuvant. In other embodiments, the immunogenic component containing the nucleic acid that encodes a respiratory pathogen antigen is formulated with an adjuvant. In an embodiment, both immunogenic components are administered in a composition containing an adjuvant. Typically, the adjuvant is admixed (e.g., prior to administration or stably formulated) with the antigenic component. When the combination immunogenic composition is to be administered to a subject of a particular age group, the adjuvant is selected to be safe and effective in the subject or population of subjects. Thus, when formulating a combination immunogenic composition for administration in an elderly subject (such as a subject greater than 65 years of age), the adjuvant is selected to be safe and effective in elderly subjects. Similarly, when the combination immunogenic composition is intended for administration in neonatal or infant subjects (such as subjects between birth and the age of two years), the adjuvant is selected to be safe and effective in neonates and infants. In the case of an adjuvant selected for safety and efficacy in neonates and infants, an adjuvant dose can be selected that is a dilution (e.g., a fractional dose) of a dose typically administered to an adult subject.

Additionally, the adjuvant is typically selected to enhance the desired aspect of the immune response when administered via a route of administration, by which the combination immunogenic composition is administered. For example, when formulating a combination immunogenic composition for nasal administration, proteosome and protollin are favorable adjuvants. In contrast, when the combination immunogenic composition is formulated for intramuscular administration, adjuvants including one or more of 3D-MPL, squalene (e.g., QS21), liposomes, and/or oil and water emulsions are favorably selected.

One suitable adjuvant for use with the immunogenic combinations disclosed herein is a non-toxic bacterial lipopolysaccharide derivative. An example of a suitable non-toxic derivative of lipid A, is monophosphoryl lipid A or more particularly 3-Deacylated monophoshoryl lipid A (3D-MPL). 3D-MPL is sold under the name MPL by GlaxoSmithKline Biologicals N.A., and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-γ (Th1) phenotype. 3D-MPL can be produced according to the methods disclosed in GB2220211 A. Chemically it is a mixture of 3-deacylated monophosphoryl lipid A with 3, 4, 5 or 6 acylated chains. In the compositions of the present disclosure small particle 3D-MPL can be used. Small particle 3D-MPL has a particle size such that it can be sterile-filtered through a 0.22 μm filter. Such preparations are described in WO94/21292.

A lipopolysaccharide, such as 3D-MPL, can be used at amounts between 1 and 50 μg, per human dose of the immunogenic composition. Such 3D-MPL can be used at a level of about 25 μg, for example between 20-30 μg, suitably between 21-29 μg or between 22 and 28 μg or between 23 and 27 μg or between 24 and 26 μg, or 25 μg. In another embodiment, the human dose of the immunogenic composition comprises 3D-MPL at a level of about 10 μg, for example between 5 and 15 μg, suitably between 6 and 14 μg, for example between 7 and 13 μg or between 8 and 12 μg or between 9 and 11 μg, or 10 μg. In a further embodiment, the human dose of the immunogenic composition comprises 3D-MPL at a level of about 5 μg, for example between 1 and 9 μg, or between 2 and 8 μg or suitably between 3 and 7 μg or 4 and μg, or 5 μg.

In other embodiments, the lipopolysaccharide can be a β(1-6) glucosamine disaccharide, as described in U.S. Pat. No. 6,005,099 and EP Patent No. 0 729 473 B1. One of skill in the art would be readily able to produce various lipopolysaccharides, such as 3D-MPL, based on the teachings of these references. Nonetheless, each of these references is incorporated herein by reference. In addition to the aforementioned immunostimulants (that are similar in structure to that of LPS or MPL or 3D-MPL), acylated monosaccharide and disaccharide derivatives that are a sub-portion to the above structure of MPL are also suitable adjuvants. In other embodiments, the adjuvant is a synthetic derivative of lipid A, some of which are described as TLR-4 agonists, and include, but are not limited to: OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetrade-canoylamino]-α-D-glucopyranosyldihydrogenphosphate), (WO 95/14026); OM 294 DP (3S, 9 R)—3—[(R)-dode-canoyloxytetradecanoylamino]-4-oxo-5-aza-9(R)-[(R)-3-hydroxytetradecanoylamino]decan-1,10-diol,1,10-bis(dihydrogenophosphate) (WO 99/64301 and WO 00/0462); and OM 197 MP-Ac DP (3S-, 9R) -3-[(R) -dodecanoyloxytet-radecanoylamino]-4-oxo-5-aza-9-[(R)-3-hydroxytetrade-canoylamino]decan-1,10-diol,1-dihydrogenophosphate 10-(6-aminohexanoate) (WO 01/46127).

Other TLR4 ligands which can be used are alkyl Glucosaminide phosphates (AGPs) such as those disclosed in WO 98/50399 or U.S. Pat. No. 6,303,347 (processes for preparation of AGPs are also disclosed), suitably RC527 or RC529 or pharmaceutically acceptable salts of AGPs as disclosed in U.S. Pat. No. 6,764,840. Some AGPs are TLR4 agonists, and some are TLR4 antagonists. Both are thought to be useful as adjuvants.

Other suitable TLR-4 ligands, capable of causing a signaling response through TLR-4 (Sabroe et al, JI 2003 p1630-5) are, for example, lipopolysaccharide from gram-negative bacteria and its derivatives, or fragments thereof, in particular a non-toxic derivative of LPS (such as 3D-MPL). Other suitable TLR agonists are: heat shock protein (HSP) 10, 60, 65, 70, 75 or 90; surfactant Protein A, hyaluronan oligosaccharides, heparan sulphate fragments, fibronectin fragments, fibrinogen peptides and b-defensin-2, and muramyl dipeptide (MDP). In one embodiment the TLR agonist is HSP 60, 70 or 90. Other suitable TLR-4 ligands are as described in WO 2003/011223 and in WO 2003/099195, such as compound I, compound II and compound III disclosed on pages 4-5 of WO2003/011223 or on pages 3-4 of WO2003/099195 and in particular those compounds disclosed in WO2003/011223 as ER803022, ER803058, ER803732, ER804053, ER804057, ER804058, ER804059, ER804442, ER804680, and ER804764. For example, one suitable TLR-4 ligand is ER804057.

Additional TLR agonists are also useful as adjuvants. The term "TLR agonist" refers to an agent that is capable of causing a signaling response through a TLR signaling pathway, either as a direct ligand or indirectly through generation of endogenous or exogenous ligand. Such natural or synthetic TLR agonists can be used as alternative or additional adjuvants. A brief review of the role of TLRs as adjuvant receptors is provided in Kaisho & Akira, Biochimica et Biophysica Acta 1589:1-13, 2002. These potential adjuvants include, but are not limited to agonists for TLR2, TLR3, TLR7, TLR8 and TLR9. Accordingly, in one embodiment, the adjuvant and combination immunogenic composition further comprises an adjuvant which is selected from the group consisting of: a TLR-1 agonist, a TLR-2 agonist, TLR-3 agonist, a TLR-4 agonist, TLR-5 agonist, a TLR-6 agonist, TLR-7 agonist, a TLR-8 agonist, TLR-9 agonist, or a combination thereof.

In one embodiment of the present disclosure, a TLR agonist is used that is capable of causing a signaling response through TLR-1. Suitably, the TLR agonist capable of causing a signaling response through TLR-1 is selected from: Tri-acylated lipopeptides (LPs); phenol-soluble modulin; Mycobacterium tuberculosis LP; S-(2,3-bis(palmitoy-loxy)-(2-RS)-propyl)-N-palmitoyl-(R)-Cys-(S)-Ser-(S)-Lys (4)-OH, trihydrochloride (Pam3Cys) LP which mimics the acetylated amino terminus of a bacterial lipoprotein and OspA LP from *Borrelia burgdorferi*.

In an alternative embodiment, a TLR agonist is used that is capable of causing a signaling response through TLR-2. Suitably, the TLR agonist capable of causing a signaling response through TLR-2 is one or more of a lipoprotein, a peptidoglycan, a bacterial lipopeptide from *M tuberculosis, B burgdorferi* or *T pallidum*; peptidoglycans from species including *Staphylococcus aureus*; lipoteichoic acids, mannuronic acids, *Neisseria* porins, bacterial fimbriae, Yersina virulence factors, CMV virions, measles haemagglutinin, and zymosan from yeast.

In an alternative embodiment, a TLR agonist is used that is capable of causing a signaling response through TLR-3. Suitably, the TLR agonist capable of causing a signaling response through TLR-3 is double stranded RNA (dsRNA), or polyinosinic-polycytidylic acid (Poly IC), a molecular nucleic acid pattern associated with viral infection.

In an alternative embodiment, a TLR agonist is used that is capable of causing a signaling response through TLR-5. Suitably, the TLR agonist capable of causing a signaling response through TLR-5 is bacterial flagellin.

In an alternative embodiment, a TLR agonist is used that is capable of causing a signaling response through TLR-6. Suitably, the TLR agonist capable of causing a signaling response through TLR-6 is mycobacterial lipoprotein, di-acylated LP, and phenol-soluble modulin. Additional TLR6 agonists are described in WO 2003/043572.

In an alternative embodiment, a TLR agonist is used that is capable of causing a signaling response through TLR-7. Suitably, the TLR agonist capable of causing a signaling response through TLR-7 is a single stranded RNA (ssRNA), loxoribine, a guanosine analogue at positions N7 and C8, or an imidazoquinoline compound, or derivative thereof. In one embodiment, the TLR agonist is imiquimod. Further TLR7 agonists are described in WO 2002/085905.

In an alternative embodiment, a TLR agonist is used that is capable of causing a signaling response through TLR-8. Suitably, the TLR agonist capable of causing a signaling response through TLR-8 is a single stranded RNA (ssRNA), an imidazoquinoline molecule with anti-viral activity, for example resiquimod (R848); resiquimod is also capable of recognition by TLR-7. Other TLR-8 agonists which can be used include those described in WO 2004/071459.

In an alternative embodiment, a TLR agonist is used that is capable of causing a signaling response through TLR-9. In one embodiment, the TLR agonist capable of causing a signaling response through TLR-9 is HSP90. Alternatively, the TLR agonist capable of causing a signaling response through TLR-9 is bacterial or viral DNA, DNA containing unmethylated CpG nucleotides, in particular sequence contexts known as CpG motifs. CpG-containing oligonucleotides induce a predominantly Th1 response. Such oligonucleotides are well known and are described, for example, in WO 96/02555, WO 99/33488 and U.S. Pat. Nos. 6,008,200 and 5,856,462. Suitably, CpG nucleotides are CpG oligonucleotides. Suitable oligonucleotides for use in the combination immunogenic composition are CpG containing oligonucleotides, optionally containing two or more dinucleotide CpG motifs separated by at least three, suitably at least six or more nucleotides. A CpG motif is a Cytosine nucleotide followed by a Guanine nucleotide. The CpG oligonucleotides are typically deoxynucleotides. In a specific embodiment the internucleotide in the oligonucleotide is phosphorodithioate, or suitably a phosphorothioate bond, although phosphodiester and other internucleotide bonds are possible. Also possible are oligonucleotides with mixed internucleotide linkages. Methods for producing phosphorothioate oligonucleotides or phosphorodithioate are described in U.S. Pat. Nos. 5,666,153, 5,278,302 and WO 95/26204.

Other adjuvants that can be used in the disclosed immunogenic combinations, and with the disclosed immunization regimens, methods, uses and kits, e.g., on their own or in combination with 3D-MPL, or another adjuvant described herein, are saponins, such as QS21.

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja Saponaria Molina), and fractions thereof, are described in U.S. Pat. No. 5,057,540 and "Saponins as vaccine adjuvants", Kensil, C. R., Crit Rev Ther Drug Carrier Syst, 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No.5,057,540 and EP 0 362 279 B1, which are incorporated herein by reference. Other saponins which have been used in systemic vaccination studies include those derived from other plant species such as Gypsophila and Saponaria (Bomford et al., Vaccine, 10(9):572-577, 1992).

QS21 is an Hplc purified non-toxic fraction derived from the bark of Quillaj a Saponaria Molina. A method for producing QS21 is disclosed in U.S. Pat. No. 5,057,540. Non-reactogenic adjuvant formulations containing QS21 are described in WO 96/33739. The aforementioned references are incorporated by reference herein. Said immunologically active saponin, such as QS21, can be used in amounts of between 1 and 50 μg, per human dose of the combination immunogenic composition. Advantageously QS21 is used at a level of about 25 μg, for example between 20-30 μg, suitably between 21-29 μg or between 22-28 μg or between 23-27 μg or between 24-26 μg, or 25 μg. In another embodiment, the human dose of the combination immunogenic composition comprises QS21 at a level of about 10 μg, for example between 5 and 15 μg, suitably between 6-14 μg, for example between 7-13 μg or between 8-12 μg or between 9-11 μg, or 10 μg. In a further embodiment, the human dose of the combination immunogenic composition comprises QS21 at a level of about 5 μg, for example between 1-9 μg, or between 2-8 μg or suitably between 3-7 μg or 4-6 μg, or 5 μg. Such formulations comprising QS21 and cholesterol have been shown to be successful adjuvants when formulated together with an antigen. Thus, for example, polypeptides of the disclosed immunogenic combinations can be provided with an adjuvant comprising a combination of QS21 and cholesterol.

Optionally, the adjuvant can alternatively or additionally include mineral salts such as an aluminium salt (for example, aluminum hydroxide, aluminum phosphate, aluminum potassium sulfate, aluminum hydroxyphosphate sulfate) or calcium salt (for example, calcium hydroxide, calcium fluoride, calcium phosphate). Other salts suitable in the formulation of an adjuvant include cerium(III) nitrate hexahydrate and zinc sulfate heptahydrate. For example, an adjuvant containing 3D-MPL in combination with an aluminium salt (e.g., aluminium hydroxide or "alum") is suitable for formulation in a combination immunogenic combinations containing antigen(s) of a respiratory pathogen as described herein. Alternatively, such mineral salt adjuvants may be used other than in combination with non-mineral-salt adjuvants, i.e. the combination immunogenic composition may be adjuvanted only with one, or more than one, mineral salt adjuvant such as aluminium hydroxide, aluminium phosphate and calcium phosphate, etc.

Another class of suitable adjuvants for use in the immunogenic combinations disclosed herein includes OMP-based immunostimulatory compositions. OMP-based immunostimulatory compositions are particularly suitable as mucosal adjuvants, e.g., for intranasal administration. OMP-based immunostimulatory compositions are a genus of preparations of outer membrane proteins (OMPs, including some porins) from Gram-negative bacteria, such as, but not limited to, *Neisseria* species (see, e.g., Lowell et al., J. Exp. Med. 167:658, 1988; Lowell et al., Science 240:800, 1988; Lynch et al., Biophys. J. 45:104, 1984; Lowell, in "New Generation Vaccines" 2nd ed., Marcel Dekker, Inc., New York, Basil, Hong Kong, page 193, 1997; U.S. Pat. Nos. 5,726,292; 4,707,543), which are useful as a carrier or in compositions for immunogens, such as bacterial or viral antigens. Some OMP-based immunostimulatory compositions can be referred to as "Proteosomes," which are hydrophobic and safe for human use. Proteosomes have the capability to auto-assemble into vesicle or vesicle-like OMP clusters of about 20 nm to about 800 nm, and to noncovalently incorporate, coordinate, associate (e.g., electrostatically or hydrophobically), or otherwise cooperate with protein antigens (Ags), particularly antigens that have a hydrophobic moiety. Any preparation method that results in the outer membrane protein component in vesicular or vesicle-like form, including multi-molecular membranous structures or molten globular-like OMP compositions of one or more OMPs, is included within the definition of Proteosome. Proteosomes can be prepared, for example, as described in the art (see, e.g., U.S. Pat. Nos. 5,726,292 or 5,985,284). Proteosomes can also contain an endogenous lipopolysaccharide or lipooligosaccharide (LPS or LOS, respectively) originating from the bacteria used to produce the OMP porins (e.g., *Neisseria* species), which generally will be less than 2% of the total OMP preparation.

Proteosomes are composed primarily of chemically extracted outer membrane proteins (OMPs) from *Neisseria menigitidis* (mostly porins A and B as well as class 4 OMP), maintained in solution by detergent (Lowell G H. Proteosomes for Improved Nasal, Oral, or Injectable Vaccines. In: Levine M M, Woodrow G C, Kaper J B, Cobon G S, eds, New Generation Vaccines. New York: Marcel Dekker, Inc. 1997; 193-206). Proteosomes can be formulated with a variety of antigens such as purified or recombinant proteins derived from viral sources, including the RSV F protein polypeptides disclosed herein, e.g., by diafiltration or traditional dialysis processes or with purified *B. pertussis* antigenic proteins. The gradual removal of detergent allows the formation of particulate hydrophobic complexes of approximately 100-200 nm in diameter (Lowell G H. Proteosomes for Improved Nasal, Oral, or Injectable Vaccines. In: Levine M M, Woodrow G C, Kaper J B, Cobon G S, eds, New Generation Vaccines. New York: Marcel Dekker, Inc. 1997; 193-206).

"Proteosome: LPS or Protollin" as used herein refers to preparations of proteosomes admixed, e.g., by the exogenous addition, with at least one kind of lipo-polysaccharide to provide an OMP-LPS composition (which can function as an immunostimulatory composition). Thus, the OMP-LPS composition can be comprised of two of the basic components of Protollin, which include (1) an outer membrane protein preparation of Proteosomes (e.g., Projuvant) prepared from Gram-negative bacteria, such as Neisseria meningitidis, and (2) a preparation of one or more liposaccharides. A lipo-oligosaccharide can be endogenous (e.g., naturally contained with the OMP Proteosome preparation), can be admixed or combined with an OMP preparation from an exogenously prepared lipo-oligosaccharide (e.g., prepared from a different culture or microorganism than the OMP preparation), or can be a combination thereof. Such exogenously added LPS can be from the same Gram-negative bacterium from which the OMP preparation was made or from a different Gram-negative bacterium. Protollin should also be understood to optionally include lipids, glycolipids, glycoproteins, small molecules, or the like, and combinations thereof. The Protollin can be prepared, for example, as described in U.S. Patent Application Publication No. 2003/0044425.

Combinations of different adjuvants, such as those mentioned hereinabove, can also be used in the disclosed immunogenic combinations (e.g., with individual components or admixtures thereof). For example, as already noted, QS21 can be formulated together with 3D-MPL. The ratio of QS21: 3D-MPL will typically be in the order of 1:10 to 10:1; such as 1:5 to 5:1, and often substantially 1:1. Typically, the ratio is in the range of 2.5:1 to 1:1 3D-MPL: QS21. Another combination adjuvant formulation includes 3D-MPL and an aluminium salt, such as aluminium hydroxide.

In some instances, the adjuvant formulation includes a mineral salt, such as an aluminium (alum) salt for example aluminium phosphate or aluminium hydroxide, or calcium phosphate. Where alum is present, e.g., in combination with 3D-MPL, the amount is typically between about 100 µg and 1 mg, such as from about 100 µg, or about 200 µg to about 750 µg, such as about 500 µg per dose.

In some embodiments, the adjuvant includes an oil and water emulsion, e.g., an oil-in-water emulsion. One example of an oil-in-water emulsion comprises a metabolisable oil, such as squalene, a tocol such as a tocopherol, e.g., alpha-tocopherol, and a surfactant, such as sorbitan trioleate (Span 85™) or polyoxyethylene sorbitan monooleate (Tween 80™), in an aqueous carrier. In certain embodiments, the oil-in-water emulsion does not contain any additional immunostimulants(s), (in particular it does not contain a non-toxic lipid A derivative, such as 3D-MPL, or a saponin, such as QS21). The aqueous carrier can be, for example, phosphate buffered saline. Additionally the oil-in-water emulsion can contain span 85 and/or lecithin and/or tricaprylin.

In another embodiment the combination immunogenic composition comprises an oil-in-water emulsion and optionally one or more further immunostimulants, wherein said oil-in-water emulsion comprises 0.5-10 mg metabolisable oil (suitably squalene), 0.5-11 mg tocol (suitably a tocopherol, such as alpha-tocopherol) and 0.4-4 mg emulsifying agent.

In one specific embodiment, the adjuvant formulation includes 3D-MPL prepared in the form of an emulsion, such as an oil-in-water emulsion. In some cases, the emulsion has a small particle size of less than 0.2 µm in diameter, as disclosed in WO 94/21292. For example, the particles of 3D-MPL can be small enough to be sterile filtered through a 0.22 micron membrane (as described in European Patent number 0 689 454). Alternatively, the 3D-MPL can be prepared in a liposomal formulation. Optionally, the adjuvant containing 3D-MPL (or a derivative thereof) also includes an additional immunostimulatory component.

The adjuvant is selected to be safe and effective in the population to which the immunogenic composition is administered. For adult and elderly populations, the formulations typically include more of an adjuvant component than is typically found in an infant formulation. In particular formulations using an oil-in-water emulsion, such an emulsion can include additional components, for example, such as cholesterol, squalene, alpha tocopherol, and/or a detergent, such as tween 80 or span85. In exemplary formulations, such components can be present in the following amounts: from about 1-50 mg cholesterol, from 2 to 10% squalene, from 2 to 10% alpha tocopherol and from 0.3 to 3% tween 80. Typically, the ratio of squalene: alpha tocopherol is equal to or less than 1 as this provides a more stable emulsion. In some cases, the formulation can also contain a stabilizer.

When a combination immunogenic composition with a RSV F protein polypeptide antigen is formulated for administration to an infant, the dosage of adjuvant is determined to be effective and relatively non-reactogenic in an infant subject. Generally, the dosage of adjuvant in an infant formulation is lower (for example, the dose may be a fraction of the dose provided in a formulation to be administered to adults) than that used in formulations designed for administration to adult (e.g., adults aged 65 or older). For example, the amount of 3D-MPL is typically in the range of 1 µg-200 µg, such as 10-100 µg, or 10 µg-50 µg per dose. An infant dose is typically at the lower end of this range, e.g., from about 1 µg to about 50 µg, such as from about 2 µg, or about 5 µg, or about 10 µg, to about 25 µg, or to about 50 µg. Typically, where QS21 is used in the formulation, the ranges are comparable (and according to the ratios indicated above). In the case of an oil and water emulsion (e.g., an oil-in-water emulsion), the dose of adjuvant provided to a child or infant can be a fraction of the dose administered to an adult subject.

An immunogenic combination as disclosed herein, or for use in the disclosed vaccination regimens, methods, uses and kits, typically contains an immunologically effective amount (or a fractional dose thereof) of the immunogenic components (and/or polypeptides or nucleic acids) and can be prepared by conventional techniques.

An "immunologically effective amount" is a quantity of a composition (typically, an immunogenic composition) used to elicit an immune response in a subject to the composition or to an antigen in the composition. Commonly, the desired result is the production of an antigen (e.g., pathogen)-specific immune response that is capable of or contributes to protecting the subject against the pathogen. However, to obtain a protective immune response against a pathogen can require multiple administrations of the immunogenic composition. Thus, in the context of this disclosure, the term immunologically effective amount encompasses a fractional dose that contributes in combination with previous or subsequent administrations to attaining a protective immune response.

Preparation of immunogenic compositions, including those for administration to human subjects, is generally described in Pharmaceutical Biotechnology, Vol. 61 Vaccine Design-the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

Typically, the amount of antigen (e.g. protein) or of nucleic acid encoding antigen in each dose of the immunogenic composition is selected as an amount which induces a protective (or immunoprotective) response without significant, adverse side effects in the typical subject. Protective in this context does not necessarily mean completely protective against infection; it means protection against symptoms or disease, especially severe disease associated with the pathogens. The amount of antigen can vary depending upon which specific antigen (or nucleic acid) is employed.

Thus, the antigen or nucleic acid that encodes an antigen is administered at an immunologically effective dose. It will be understood by those of skill in the art that the immunologically effective amount can differ between subjects based on parameters such as weight, age, and immunological and/or physiological status, such that, for example, an infant dose is generally lower than an adult dose, and a human dose can be different from the dose administered to an experimental (non-human animal) subject. For example, a human dose is typically 10×-20× that of the dose administered to a mouse. Generally, with respect to the polypeptide antigen component, it is expected that each human dose will comprise 1-1000 µg of each protein or antigen, such as from about 1 µg to about 100 µg, for example, from about 1 µg to about 50 µg, such as about 1 µg, about 2 µg, about 5 µg, about 10 µg, about 15 µg, about 20 µg, about 25 µg, about 30 µg, about 40 µg, or about 50 µg. Alternatively, the polypeptide component can be administered in an amount that is between 50 µg and 250 µg, such as about 50 µg, 75 µg, 100 µg, 120 µg, 150 µg, 175 µg, 200 µg or 250 µg. These amounts will be understood to be illustrative, and an integer or interval within the above ranges is acceptable.

With respect to the nucleic acid component, the amount is similarly calculated to provide an immunologically effective amount to the subject (in one or more administrations). Such an amount may be in the case of a nucleic acid, between 1 ng and 100 mg. For example, a suitable amount of a DNA can be from 1 µg to 100 mg. In the case of RNA, a suitable amount can be from 1 ng to 100 µg. An appropriate amount of the particular nucleic acid (e.g., vector) can readily be determined by those of skill in the art. Exemplary effective amounts of a nucleic acid component can be between 1 ng and 100 µg, such as between 1 ng and 1 µg (e.g., 100 ng-1 µg), or between 1 µg and 100 µg, such as 10 ng, 50 ng, 100 ng, 150 ng, 200 ng, 250 ng, 500 ng, 750 ng, or 1 µg (or any integer encompassed within or interval inclusive of these amounts). Effective amounts of a nucleic acid can also include from 1 µg to 500 µg, such as between 1 µg and 200 µg, such as between 10 and 100 µg, for example 1 µg, 2 µg, 5 µg, 10 µg, 20 µg, 50 µg, 75 µg, 100 µg, 150 µg, or 200 µg, or an integer or interval or fraction between 1 and 200 µg. Alternatively, an exemplary effective amount of a nucleic acid can be between 100 µg and 1 mg, such as from 100 µg to 500 µg, for example, 100 µg, 150 µg, 200 µg, 250 µg, 300 µg, 400 µg, 500 µg, 600 µg, 700 µg, 800 µg, 900 µg or 1 mg, or any integer or interval between 1 µg and 1 mg.

In the case of a recombinant viral vector (e.g., adenovirus) containing the nucleic acid component is typically administered at a dose that is $1 \times 10^5$ to $1 \times 10^{15}$ viral particles, such as from $1 \times 10^8$ to $1 \times 10^{12}$ (e.g., $1 \times 10^8$, $5 \times 10^8$, $1 \times 10^9$, $5 \times 10^9$, $1 \times 10^{10}$, $2.5 \times 10^{10}$, $5 \times 10^{10}$, $1 \times 10^{11}$, $5 \times 10^{11}$, $1 \times 10^{12}$ particles). Alternatively, a viral vector can be administered at a dose that is typically from $1 \times 10^5$ to $1 \times 10^{10}$ plaque forming units (PFU), such as $1 \times 10^5$ PFU, $5 \times 10^5$ PFU, $1 \times 10^6$ PFU, $5 \times 10^6$ PFU, $1 \times 10^7$ PFU, $5 \times 10^7$ PFU, $1 \times 10^8$ PFU, $5 \times 10^8$ PFU, 1×10⁹PFU, 5×10⁹PFU, or 1×10¹⁰PFU. As above, any integer or interval within the designated ranges can be administered.

Generally a human dose will be in a volume of between 0.5 ml and 2 ml. Thus the composition for the uses and methods described herein can be formulated in a volume of, for example 0.5, 1.0, 1.5 or 2.0 ml human dose per individual or combined immunogenic components.

The amount utilized in an immunogenic composition is selected based on the subject population. An optimal amount for a particular composition can be ascertained by standard studies involving observation of antibody titres and other responses in subjects. Following an initial vaccination, subjects can receive a second administration (e.g., boost) in about 4-12 weeks. For example, when administering an immunogenic composition to an infant subject, the initial and subsequent inoculations can be administered to coincide with other vaccines administered during this period.

Additional formulation details can be found in WO2010/149745, which is incorporated herein by reference for the purpose of providing additional details concerning formulation of immunogenic compositions comprising RSV F protein antigens such as PreF analogs.

The immunization embodiment described herein is carried out via a suitable route for administration, such as a parenteral method, including intramuscular, transdermal, intradermal, or cutaneous administration. For example, the immunization can be carried out cutaneously, which means that the antigen is introduced into the dermis and/or epidermis of the skin (e.g., intradermally). In certain favorable embodiments, the two immunogenic components of the immunogenic combination are administered colocationally, at or at approximately the same site on the subject, for example, to the same side or extremity. In the case of parenteral administration, colocationally means in proximity at the same (or approximately the same) site on the body, such as to the same site (e.g., by the same device), or within about 10 cm, or more commonly within about 5 cm, such as within about 2 cm, or within 1 cm. In some instances, the two or more components are combined (co-formulated) in a single composition for administration to the same site. Thus, it will be understood that in one favorable embodiment, the administration of the immunogenic components to a bilaterally symmetrical subject (such as a human), can be to the co-lateral side of the body. That is, the immunogenic component containing the polypeptide antigen and the immunogenic component that contains the nucleic acid that encodes an antigen are co-laterally administered. Optionally, the two components are co-formulated in a single immunogenic composition either during manufacture or prior to administration.

Delivery via the cutaneous route including the intradermal route can allow a lower dose of antigen than other routes such as intramuscular delivery. Therefore also provided is an immunogenic combination for cutaneous or intradermal delivery comprising antigens of a respiratory pathogen in a low dose e.g. less than the normal intramuscular dose, e.g. 50% or less of the normal intramuscular dose as provided above for the protein or nucleic acid components. Optionally the immunogenic composition for cutaneous or intradermal delivery also comprises an adjuvant e.g. an metallic salt or QS21 or 3D-MPL or a combination thereof.

Devices for cutaneous administration include short needle devices (which have a needle between about 1 and about 2 mm in length) such as those described in U.S. Pat. Nos. 4,886,499, 5,190,521, 5,328,483, 5,527,288, 4,270,537, 5,015,235, 5,141,496, 5,417,662 and EP1092444. Cutaneous vaccines may also be administered by devices which limit the effective penetration length of a needle into the skin, such as those described in WO99/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 5 4,790,824, 4,941,880, 4,940,460, WO 97/37705 and WO 97/13537.

Devices for cutaneous administration also include ballistic powder/particle delivery devices which use compressed gas to accelerate vaccine in powder form through the outer layers of the skin to the dermis. Additionally, conventional syringes may be used in the classical mantoux method of cutaneous administration. However, the use of conventional syringes requires highly skilled operators and thus devices which are capable of accurate delivery without a highly skilled user are preferred. Additional devices for cutaneous administration include patches comprising immunogenic compositions as described herein. A cutaneous delivery patch will generally comprise a backing plate which includes a solid substrate (e.g. occlusive or nonocclusive surgical dressing). Such patches deliver the immunogenic composition to the dermis or epidermis via microprojections which pierce the stratum corneum. Microprojections are generally between 10 Dm and 2 mm, for example 20 Dm to 500 Dm, 30 Dm to 1 mm, 100 to 200, 200 to 300, 300 to 400, 400 to 500, 500 to 600, 600 to 700, 700, 800, 800 to 900, 100 Dm to 400 Dm, in particular between about 200 Dm and 300 Dm or between about 150 Dm and 250 Dm. Cutaneous delivery patches generally comprise a plurality of microprojections for example between 2 and 5000 microneedles for example between 1000 and 2000 microneedles. The microprojections may be of any shape suitable for piercing the stratum corneum,epidermis and/or dermis Microprojections may be shaped as disclosed in WO2000/074765 and WO2000/074766 for example. The microprojections may have an aspect ratio of at least 3:1 (height to diameter at base), at least about 2:1, or at least about 1:1. One suitable shape for the microprojections is a cone with a polygonal bottom, for example hexagonal or rhombus-shaped. Other possible microprojection shapes are shown, for example, in U.S. Published Patent App. 2004/0087992. In a particular embodiment, microprojections have a shape which becomes thicker towards the base. The number of microprotrusions in the array is typically at least about 100, at least about 500, at least about 1000, at least about 1400, at least about 1600, or at least about 2000. The area density of microprotrusions, given their small size, may not be particularly high, but for example the number of microprotrusions per cm2 may be at least about 50, at least about 250, at least about 500, at least about 750, at least about 1000, or at least about 1500. In one embodiment of the disclosure the combination immunogenic composition is delivered to the subject within 5 hours of placing the patch on the skin of the host, for example, within 4 hours, 3 hours, 2 hours, 1 hour or 30 minutes. In a particular embodiment, the combination immunogenic composition is delivered within 20 minutes of placing the patch on the skin, for example within 30 seconds 1, 2, 3, 4, 5, 6, 7, 8, 9, 10, 11, 12, 13, 14, 15, 16, 17, 18 or 19 minutes.

The microprojections can be made of any suitable material known to the skilled person. In a particular embodiment at least part of the microprojections are biodegradable, in particular the tip of the microprojection or the outer most layer of the microprojection. In a particular embodiment substantially all the microprojection is biodegradable. The term "biodegradable" as used herein means degradable under expected conditions of in vivo use (e.g. insertion into skin), irrespective of the mechanism of biodegradation. Exemplary mechanisms of biodegradation include disintegration, dispersion, dissolution, erosion, hydrolysis, and enzymatic degradation.

Examples of microprojections comprising antigens are disclosed in WO2008/130587 and WO2009/048607. Methods of manufacture of metabolisable microneedles are disclosed in WO2008/130587 and WO2010/124255. Coating of microprojections with antigen can be performed by any method known to the skilled person for example by the methods disclosed in WO06/055844, WO06/055799.

Suitable delivery devices for cutaneous delivery including intradermal delivery, in the methods and uses described herein include the BD Soluvia™ device which is a microneedle device for intradermal administration, the Corium MicroCor™ patch delivery system, the Georgia Tech microneedle vaccine patch, the Nanopass microneedle delivery device and the Debiotech Nanoject™ microneedle device. Also provided is a cutaneous or intradermal delivery device containing a combination immunogenic component or combination as described herein, optionally formulated with an adjuvant.

The immunogenic combinations can be administered via a mucosal route, including routes, such as intranasal, or oral, that directly place the antigens in contact with the mucosa of the upper respiratory tract.

Thus, the immunogenic combinations, and the components thereof, are contemplated for use in medicine, and in particular for the prevention or treatment in a human subject of infection by, or disease associated with a respiratory pathogen, (such as RSV).

In a particular embodiment of such methods and uses, the subject is a human subject. Said human subject may be selected from the group of: a neonate; an infant; a child; an adolescent; an adult; and an elderly adult. The subject may be a pregnant female with a gestational infant. Alternatively, the subject may not be a pregnant female. Where the subject is a neonate, administration of the combination immunogenic composition may take place within 1 day, or within 1 week, or within 1 month of birth.

In connection with the disclosed method for eliciting an immune response against a respiratory pathogen, comprising administering to a subject an immunologically effective amount of the immunogenic combination disclosed herein, the elicited immune response against the respiratory pathogen (e.g., RSV) advantageously comprises a protective immune response that reduces or prevents incidence, or reduces severity, of infection with the pathogen (e.g., RSV) and/or reduces or prevents incidence, or reduces severity, of a pathological response following infection with the pathogen. Said elicited immune response may be a booster response.

Favorably, such administration reduces the symptoms or disease (for example, pneumonia and/or respiratory distress and failure, or the need for hospitalization due to severe respiratory disease) in such a cohort by at least about 50%, or at least about 60%, or by 60 to 70%, or by at least about 70%, or by at least about 80%, or by at least about 90% compared to unvaccinated subjects. Whether there is considered to be a need for hospitalization due to severe LRTI, or whether a particular case of LRTI is hospitalized, may vary from country to country and therefore severe LRTI as judged according to defined clinical symptoms well known in the art may be a better measure than the need for hospitalization.

When the immunogenic combination is administered to an infant, the composition can be administered one or more times. The first administration can be at or near the time of birth (e.g., on the day of or the day following birth), or within 1 week of birth or within about 2 weeks of birth. Alternatively, the first administration can be at about 4 weeks after birth, about 6 weeks after birth, about 2 months after birth, about 3 months after birth, about 4 months after birth, or later, such as about 6 months after birth, about 9 months after birth, or about 12 months after birth.

As mentioned above, the immunogenic components of the combination for use in the disclosed vaccination regimens, methods and uses may be co-formulated compositions as described herein, or may be different compositions which separately provide each component. Such "separate" compositions may be provided as kits.

In such a kit, the polypeptide antigen of the first immunogenic component and/or the nucleic acid that encodes an antigen of the second immunogenic component (as disclosed above) can be contained in one (combined or co-formulated) container or more than one container, such as in at least one (or one or more) pre-filled syringe. Such a syringe may be a multi-chamber (e.g., dual-chamber) syringe. In the case of a multi-chamber syringe, in an embodiment, the first immunogenic component is contained within one chamber, and the second immunogenic component is contained within a second chamber. Prior to administration, the two components can be admixed and then introduced to the subject at the same site (e.g., through a single needle). In another embodiment, the kit contains an alternative delivery device, such as a patch as disclosed herein.

The following examples are provided to illustrate certain particular features and/or embodiments. These examples should not be construed to limit the invention to the particular features or embodiments described.

EXAMPLES

Example 1

Combined Immunization of CD1 Mice with an Adenoviral Vector Expressing RSV F, N and M2.1 Proteins and An Adjuvanted Recombinant F Protein Induces a Broader Immune Response than Each Individual Vaccine Regimen Immunogenicity of two doses of the combined PanAd3 RSV (a PanAd 3 vector containing a nucleic acid insert which encodes the amino acid sequence represented in SEQ ID NO;4) and recombinant F (rF) protein/AS04 was evaluated in mice. Groups of CD1 mice (n=10/group) were immunized intra-muscularly twice at a 4-week interval with the following formulations ($1^{st}$ administration/$2^{nd}$ administration). In this example, the recombinant F protein was selected to be a conformationally constrained F protein analog that was engineered to be stabilized in the prefusion conformation (referred to hereafter in the Examples as rF or as PreF—this is the antigen represented in SEQ ID NO:2). In group 5, adenovirus and recombinant protein were co-administered by 2 injections at the same site separated by approximately 10 min.

| | 1st Administration | 2nd Administration |
|---|---|---|
| 1 | PanAd3 RSV IM $10^8$vp | PanAd3 RSV IM $10^8$vp |
| 2 | PanAd3 RSV IN $10^8$vp | MVA IM $10^7$pfu |
| 3 | PanAd3 RSV IM $10^8$vp | rF protein 0.5ug-AS04 |
| 4 | rF protein-0.5ug AS04 | rF protein 0.5ug-AS04 |
| 5 | PanAd3 RSV IM $10^8$vp + rF protein 0.5ug-AS04 | PanAd3 RSV IM $10^8$vp + rF protein 0.5ug-AS04 |

Sera from all mice were individually collected on Day 49 (20 days after the second immunization) and tested for the presence of RSV neutralizing antibodies using a plaque reduction assay.

Briefly, serial dilutions of each serum were pre-incubated with RSV A (Long strain) at 37° C. After incubation, the virus-serum mixture was transferred to plates previously seeded with Vero cells. On each plate, cells in one column were incubated with virus only (100% infectivity) and 2 wells received no virus or serum (cell controls). Plates were incubated for 2 hours at 33° C., medium was removed and RSV medium containing 0.5% CMC (low viscosity carboxymethylcellulose) was added to all wells. The plates were incubated for 3 days at 33° C. before immunofluorescence staining.

For staining, cell monolayers were washed with PBS and fixed with 1% paraformaldehyde. RSV-positive cells were detected using a commercial goat anti-RSV antiserum followed by a rabbit anti-goat IgG conjugated to FITC. The number of stained plaques per well was counted using an automated imaging system. Neutralizing antibody titer of each serum was determined as the inverse of the serum dilution causing 60% reduction in the number of plaques as compared to the control without serum (ED60). Results are illustrated in FIG. 1. The statistical method employed to compare different groups was an Analysis of Variance (ANOVA 1) on the log10 values.

Figure 2:
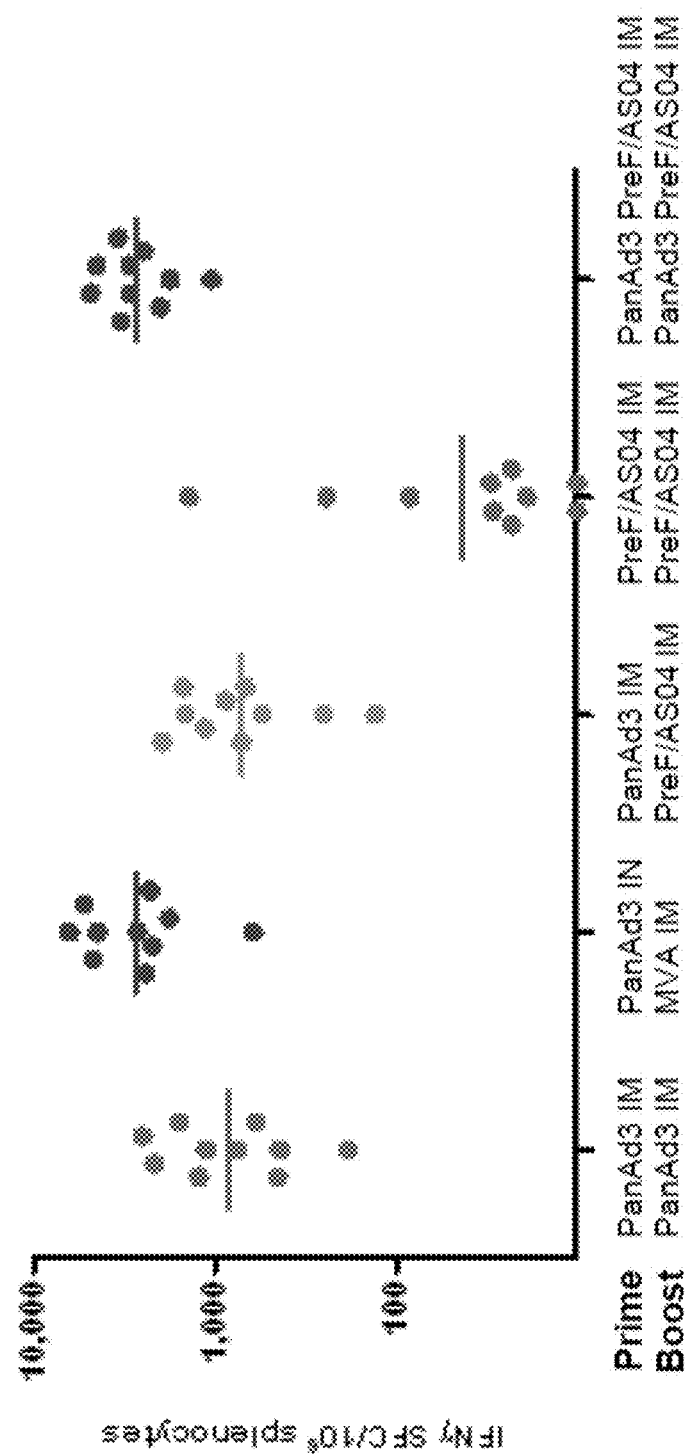
FIG. 2 is a graph illustrating interferon-gamma (IFNγ) production following immunization according to various regimens.

The cellular response was evaluated by measuring IFNγ-producing splenocytes 3 weeks after the second immunization. Antigen-specific IFNγ production by splenocytes was determined by a standard ELISpot assay. Briefly, multi-screen 96-well filtration plates were coated with anti-mouse IFNγ antibody and incubated overnight at +4° C. The following day, lymphocytes were prepared and incubated in Ag-coated wells for 16 hours at 37° C. in the presence of the peptides spanning the corresponding antigens. After overnight incubation, the cells were removed and biotinylated anti-mouse IFNγ was added and incubated 3 hours at room temperature. For development, alkaline phosphatase-conjugated streptavidin was added, followed by the addition of 1-Step NBT-BCIP Development Solution. Plates were acquired and analyzed by an automated plate reader. ELISpot data were expressed as IFNγ spot forming cells (SFC) per million splenocytes. Results are illustrated in FIG. 2.

Results presented in FIG. 1 indicate that the co-administration of PanAd3 RSV and ajduvanted recombinant F protein (co-ad group) induced the highest levels of neutralizing antibodies. Additionally, as compared to two doses of ajduvanted recombinant F protein, the co-ad group induced a much higher cellular response (FIG. 2). A mirror situation was observed when comparing the co-ad group to two doses of PanAd3 RSV: the co-ad group induced a slightly higher T-cell response but significantly higher neutralizing antibody titers. Although, the prime PanAd3 RSV/boost MVA group induced a high cellular response (FIG. 2), the neutralizing antibody titers in this group were significantly lower than those observed in the co-ad group (FIG. 1). In conclusion, co-administration of PanAd3 RSV and ajduvanted recombinant F protein resulted in the highest combined humoral and cellular responses of all the tested vaccine regimens.

Example 2

Combined Immunization of Balb/c Mice with An Adenoviral Vector Expressing RSV F, N and M2.1 Proteins and An Adjuvanted Recombinant F Protein Induces High Levels of Neutralizing Antibodies and CD8 T-Cell Responses The immunogenicity of the combined PanAd3 RSV+rF/AS04 was evaluated by measuring the neutralizing antibody response as well as identifying M2.1-specific CD8 T cells in the blood of immunized mice (inbred Balb/c), 14 days after the second immunization. Groups of Balb/c mice (n=11/group) were immunized intra-muscularly twice at a 3-week interval with the following formulations (1st/2nd).

| Group | 1st Administration | 2nd Administration |
|---|---|---|
| 1 | PanAd3 RSV IM $10^8$vp | PanAd3 RSV IM $10^8$vp |
| 2 | PanAd3 RSV IM $10^8$vp + rF protein 0.5ug | PanAd3 RSV IM $10^8$vp + rF protein 0.5ug (coformulated) |
| 3 | PanAd3 RSV IM $10^8$vp + rF protein 0.5 μg-Alum | PanAd3 RSV IM $10^8$vp + rF protein 0.5 μg-Alum (colocalized) |
| 4 | PanAd3 RSV IM $10^8$vp + rF protein 0.5 μg-AS04 | PanAd3 RSV IM $10^8$vp + rF protein 0.5 μg-AS04 0.5ug (colocalized) |
| 5 | PBS | PBS |

Figure 3:
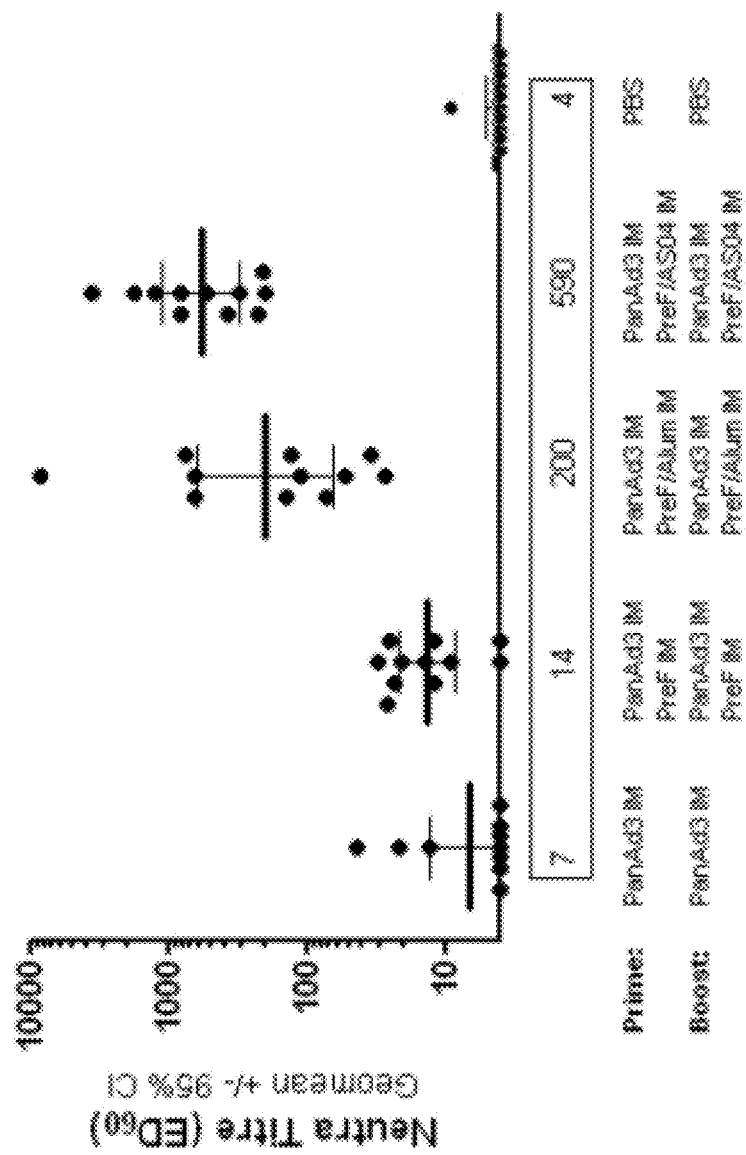
FIG. 3 is a graph illustrating RSV A neutralizing titre following immunization according to various regimens.

The neutralizing antibody response was evaluated as described in Example 1, results are illustrated in FIG. 3. Two doses of a combination vaccine composed of PanAd3 RSV and the recombinant F protein (PreF) adjuvanted with either Alum or AS04 induced significantly higher titers than 2 doses of PanAd3 RSV.

Figure 4:
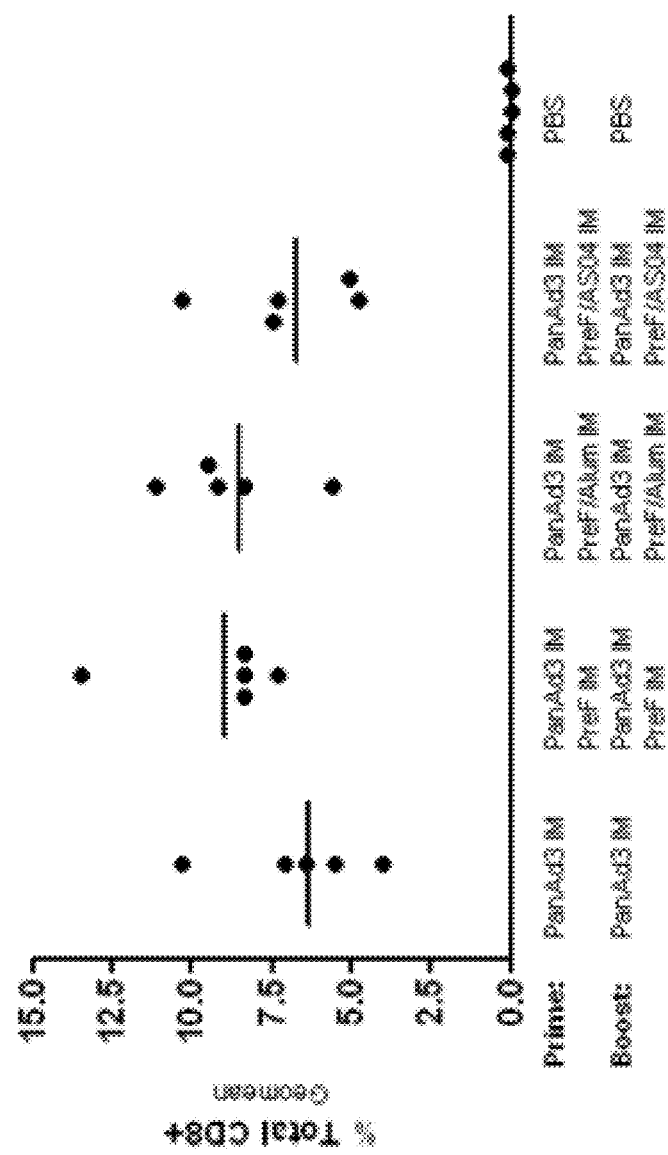
FIG. 4 is a graph illustrating RSV M2-1-specific CD8+ T cells following immunization according to various regimens.

The CD8 T-cell response was measured by identifying M2.1-specific cells in whole blood with a fluorochrome-tagged pentameric major histocompatibility complex (MHC) class I carrying the M2.1 82-90 epitope. To this end, blood was collected from each mouse, red blood cells were lysed, and cells were stained with a fluorescent viability marker, CD3, CD8 and B-220 antibodies and the MHC pentamer. Stained cells were analyzed by flow cytometry (LSR, Beckton Dickinson) and the proportion of pentamer-positive CD8 T-cells was determined (FIG. 4).

Vaccination with two doses of PanAd3 RSV or with any of the co-administration regimens induced a strong M2.1-specific CD8 response. When combined with the neutralizing antibody data, the CD8 T-cell data indicate that a vaccine regimen consisting of co-administration of PanAd3 RSV and rF adjuvanted with either Alum or AS04 combines strong humoral and cellular immune responses.

Example 3

Concurrent Immunization of Balb/c Mice with An Adenoviral Vector Expressing RSV F, N and M2.1 Proteins and An Adjuvanted Recombinant F Protein Induces Strong Humoral Immune Responses and Protects from RSV Challenge Immunogenicity of two doses of co-administered PanAd3 RSV+RSV-rF/AS04 was evaluated in Balb/c mice. Groups of Balb/c mice (n=13/group) were immunized intra-muscularly twice at a 3-week interval with the following formulations:

| Group | 1st Administration | 2nd Administration |
|---|---|---|
| 1 | PanAd3 RSV IN $10^8$vp | MVA IM $10^7$pfu |
| 2 | PanAd3 RSV IM $10^8$vp | MVA IM $10^7$pfu |
| 3 | PanAd3 RSV IN $10^8$vp | rF protein 2 µg-AS04 |
| 4 | PanAd3 RSV IM $10^8$vp | rF protein 2 µg-AS04 |
| 5 | PanAd3 RSV IM $10^8$vp + rF protein 2 µg-AS04 | PanAd3 RSV IM $10^8$vp + rF protein 2 µg-AS04 |
| 6 | rF protein 2 µg-AS04 | rF protein 2 µg-AS04 |
| 7 | Live RSV 8.3 × $10^5$pfu | no vaccine |
| 8 | FI-RSV 1/150 | FI-RSV 1/150 |
| 9 | PBS | PBS |

In group 5, adenovirus and recombinant protein were co-administered by 2 injections at the same site separated by approximately 10 minutes.

Serum was collected 14 days after the second immunization (study day 35), at which time animals were challenged intranasally with 2.9×$10^6$ pfu live RSV A Long. Lungs from 5 animals were collected 4 days after challenge for evaluation of lung viral load. The neutralizing antibody response was evaluated as described in Example 1, 14 days after the second immunization.

Figure 5:
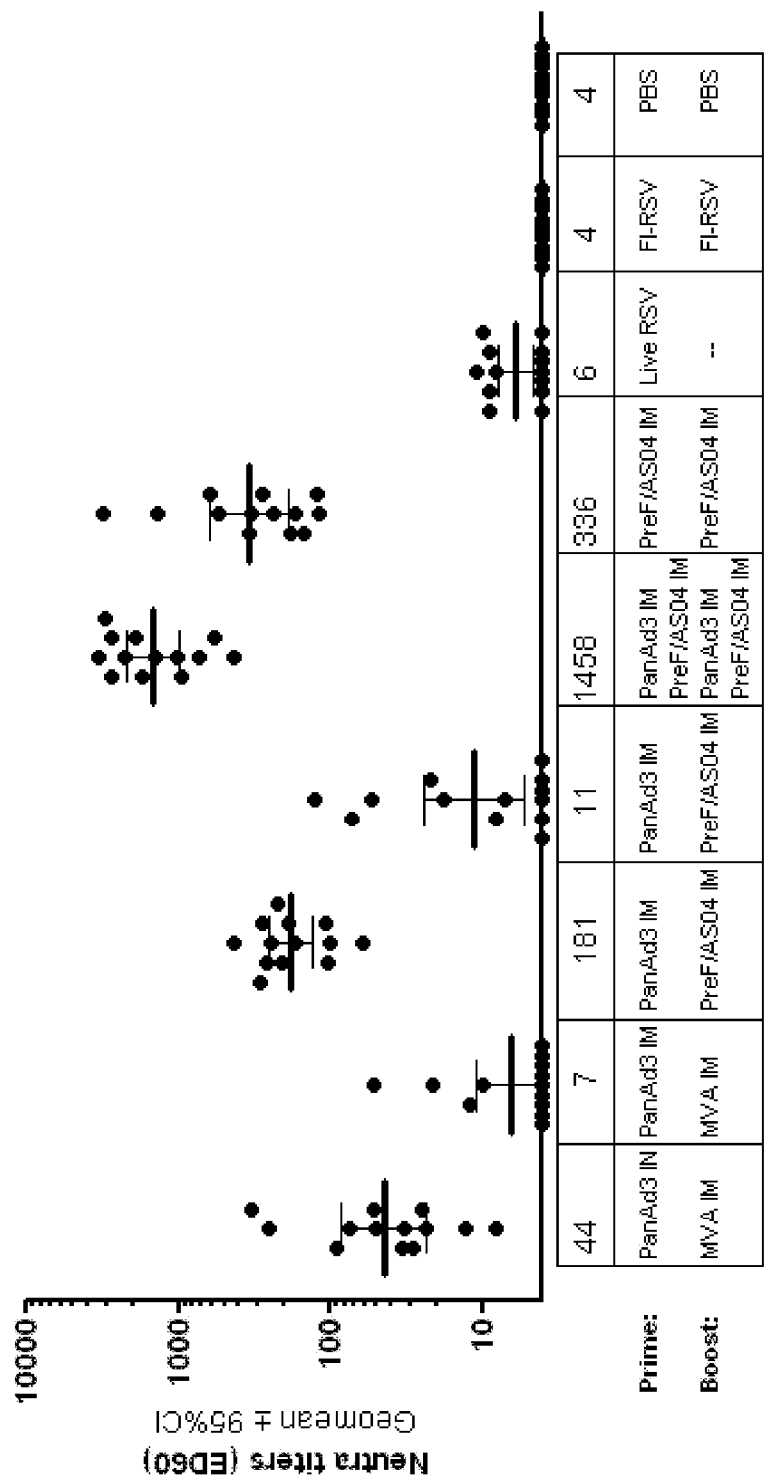
FIG. 5 is a graph illustrating neutralizing titre following immunization according to various regimens.

As observed in CD1 mice, in Balb/c the co-administration of PanAd3 RSV and adjuvanted F (PreF) protein resulted in levels of RSV neutralizing antibodies significantly higher than in all other tested groups, notably two doses of adjuvanted F protein or the sequential administration of a combination of PanAd3 RSV and MVA or PanAd3 RSV and recombinant protein (FIG. 5).

Figure 6:
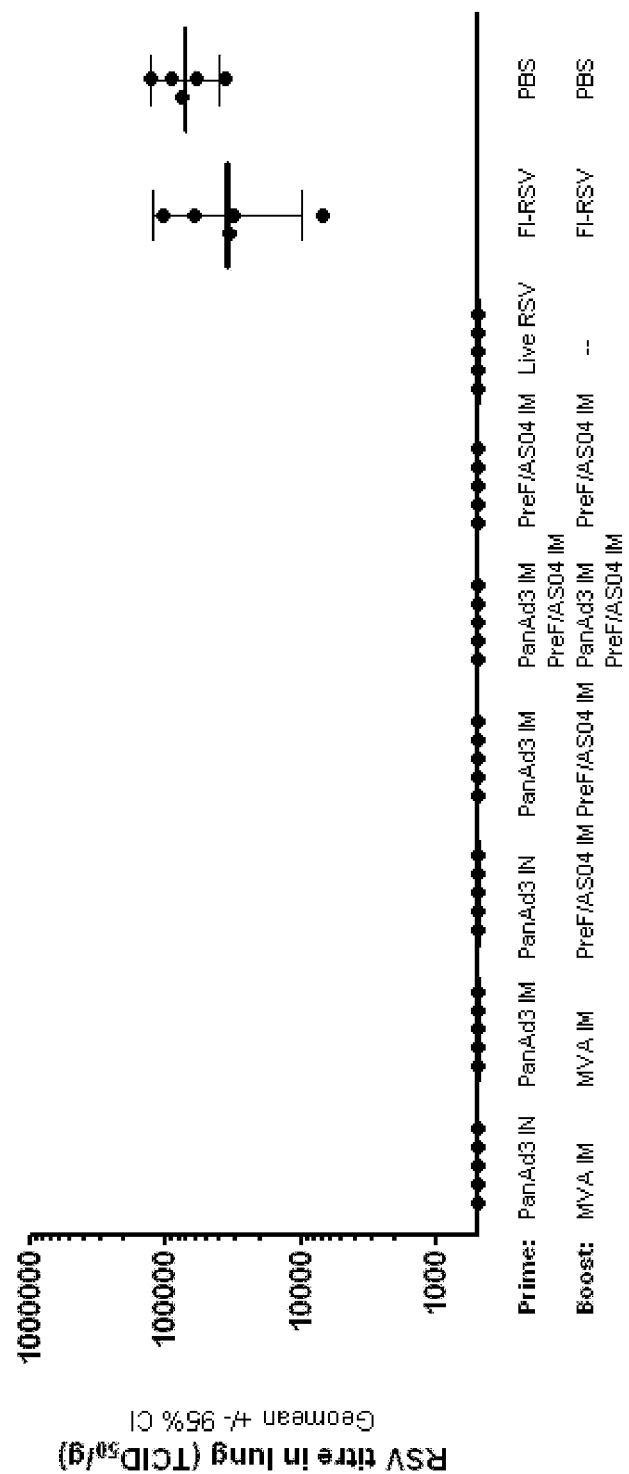
FIG. 6 is a graph illustrating RSV titre in lung following immunization according to various regimens.

To measure the efficacy of these exemplary vaccines, lungs were harvested 4 days post RSV challenge and individually weighed and homogenized. Serial dilutions (8 replicates each) of each lung homogenate were incubated with Vero cells and wells containing plaques were identified by immunofluorescence, 6 days after seeding. The viral titer was determined using the Spearman-Kärber method for TCID50 calculation and was expressed per gram of lung. Viral replication was inhibited in the lungs of all vaccinated animals, indicating that all tested vaccine regimens were protective in this model (FIG. 6).

Example 4

Concurrent Immunization of Balb/c Mice with An Adenoviral Vector Expressing RSV Proteins and An Adjuvanted Recombinant F (PreF) Protein Induces a Th1 phenotype in Lung T Cells After RSV Challenge and Does Not Induce Lung Eosinophilia or Mucus Production The effect of vaccination with a regimen comprising an adenovirus vector RSV candidate and adjuvanted protein on the Th1/Th2 response of lung CD4 T-cells, lung eosinophilia and mucus production after challenge was evaluated in Balb/c mice. FI-RSV was used as a positive control for enhanced pathology. Groups of Balb/c mice (n=12 or 13/group) were immunized intra-muscularly twice at a 3-week interval with the following formulations:

| Group | 1st Administration | 2nd Administration |
|---|---|---|
| 1 | PanAd3 RSV IN $10^8$vp | MVA IM $10^7$pfu |
| 2 | PanAd3 RSV IM $10^8$vp | MVA IM $10^7$pfu |
| 3 | PanAd3 RSV IN $10^8$vp | rF protein 2 µg-AS04 |
| 4 | PanAd3 RSV IM $10^8$vp | rF protein 2 µg-AS04 |
| 5 | PanAd3 RSV IM $10^8$vp + rF protein 2 µg-AS04 | PanAd3 RSV IM $10^8$vp + rF protein 2 µg-AS04 |
| 6 | rF protein 2 µg-AS04 | rF protein 2 µg-AS04 |
| 7 | Live RSV 8.3 × $10^5$pfu | no vaccine |
| 8 | FI-RSV 1/150 | FI-RSV 1/150 |
| 9 | PBS | PBS |

In group 5, adenovirus and recombinant protein were co-administered by 2 injections at the same site separated by approximately 10 minutes.

Fourteen days after the second immunization (study day 35), animals were challenged intranasally with 1-3×$10^6$ pfu live RSV A Long. Lungs were collected from 12 animals/group and 4 pools of 3 lungs were prepared. The lungs were minced and incubated in RPMI containing Liberase TL and DNAse for 45 min at 37° C. on orbital shaker. All tissues were then homogenized, filtered through sterile 100 µm Nylon cell strainer and lymphocytes were isolated by Percoll gradient. White cells were collected from the interface and incubated with overlapping peptides from the F antigen for 6 h at 37° C., with addition of Brefeldin A after the first 30 min of incubation. Plates were stored overnight at 4° C. On the next days, cells were centrifuged, resuspensed, washed, incubated with a viability marker, washed, fixed and permeabilized and stained with fluorochrome-conjugated antibodies to CD4, CD8, CD45, IL-13 and IFNγ. Cells were acquired on flow cytometer (LSR, Becton Dickinson) and the percentage of $CD45^{pos}CD4^{pos}CD8^{neg}IFN\gamma^{pos}/IL-13^{neg}$ cells (Th1) and $CD45^{pos}CD4^{pos}CD8^{neg}IFN\gamma^{neg}/IL-13^{pos}$ cells (Th2) cells were determined. The ratio of Th2/Th1 cells was calculated (FIG. 7).

Figure 7:
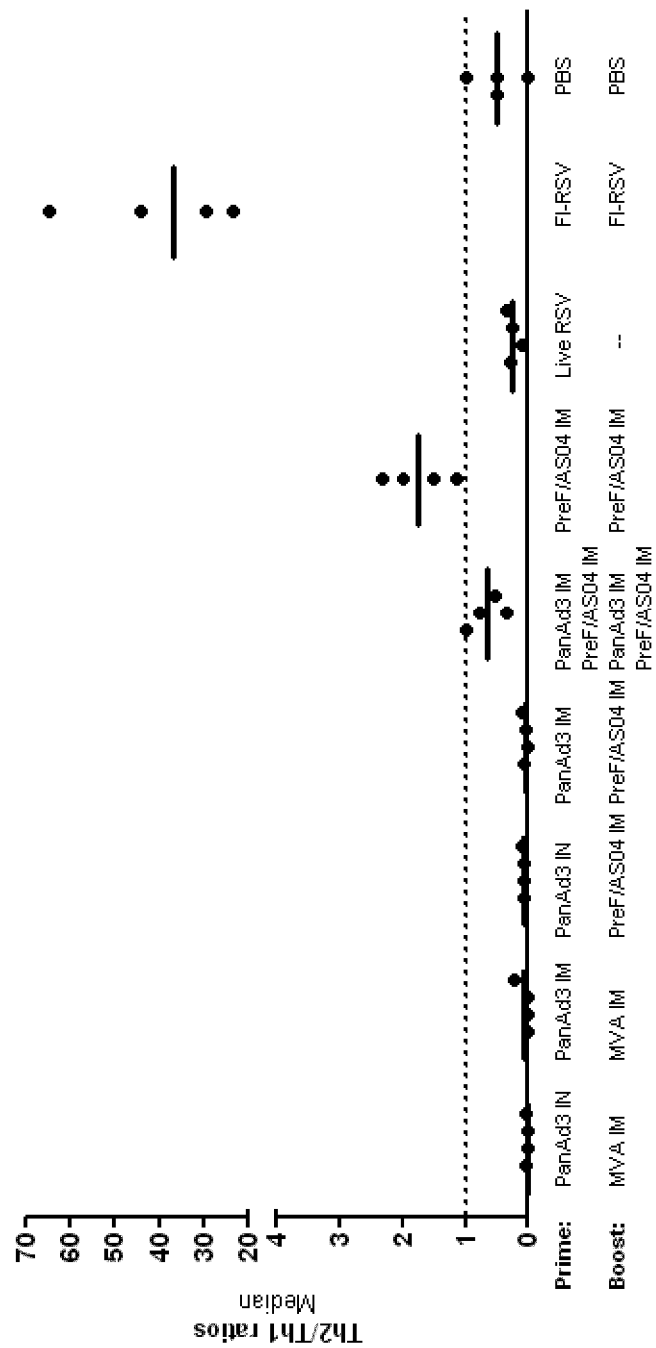
FIG. 7 is a graph illustrating the ratio of Th1 and Th2 T cells following immunization according to various regimens.

FIG. 7 shows that the combination vaccine PanAd3 RSV+rF/AS04 shifts the Th2/Th1 ratio towards Th1 when compared to the rF/AS04 formulation (the balanced Th2/Th1 ratio of 1 is indicated by the dotted line). All the vaccine formulations containing rF, PanAd3 RSV or MVA combinations induce a much lower Th2/Th1 ratio than the one observed in the FI-RSV group, a vaccine regimen known to induce high levels of CD4 Th2 cells.

For histopathology, the left lung from 13 animals was collected, inflated in formalin and periodic acid-Schiff staining was performed on formalin-fixed paraffin-embedded (FFPE) mouse lung tissue sections. The stained slides underwent quantitative analysis using image analysis software. For quantitative analysis of PAS-positive tissue (mucus-producing cells), the area (divided by a factor of 10) of PAS-positive segmented tissue was normalized by the perimeter of the airway epithelium, and expressed as the mean PAS load per millimeter of basement membrane (BM)±standard deviation. This was typically performed on 20 airways per subject and the average PAS/mmBM per subject was calculated (FIG. 8).

Figure 8:
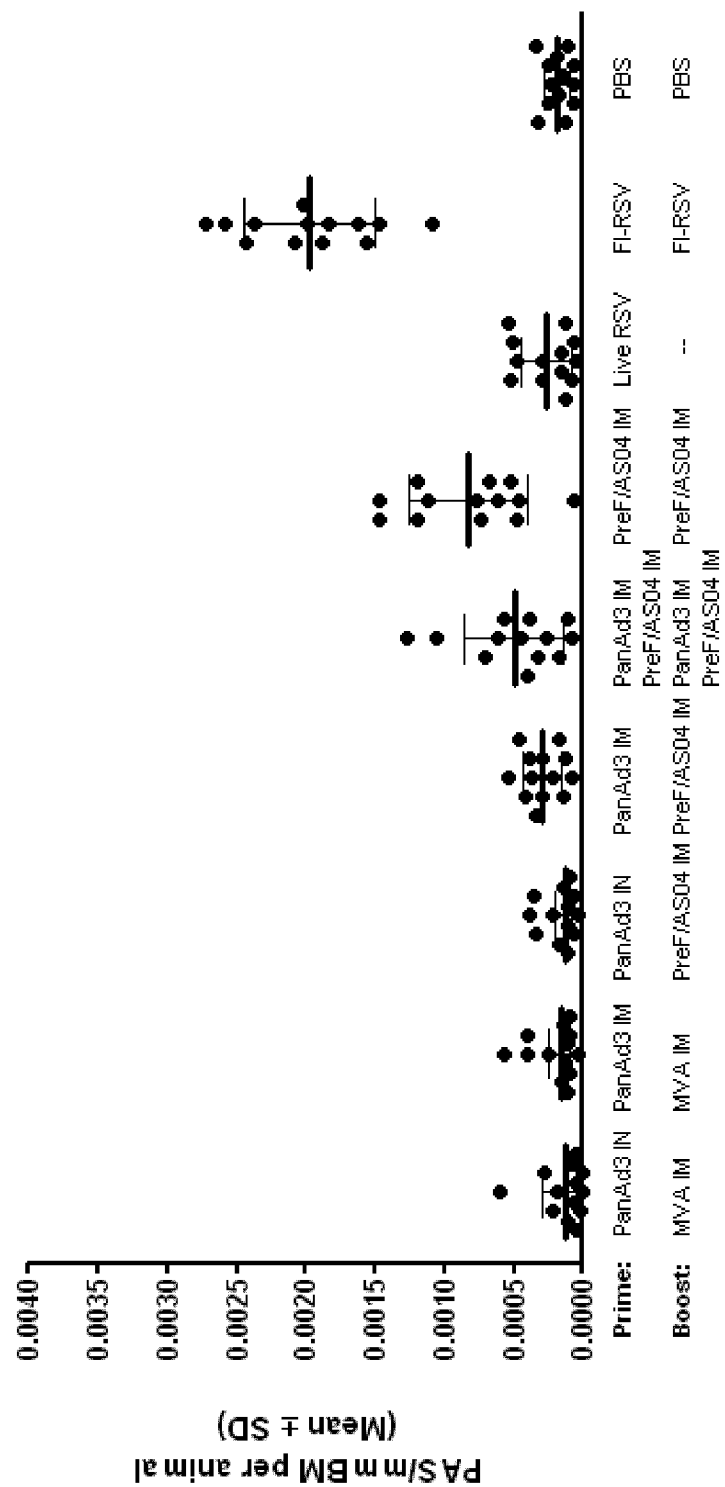
FIG. 8 is a graph illustrating the number of mucus-producing cells in lungs following challenge of subjects immunized according to various regimens.

FIG. 8 shows that the combination vaccine PanAd3 RSV+rF/AS04 is able to reduce the number of mucus-producing cells when compared to the fF/AS04 formulation. In addition, the co-administration formulation and all other tested PanAd3 RSV-, MVA- and fF/AS04 combinations induce significantly lower mucus-producing cells than the FI-RSV vaccine after RSV challenge.

Bronchoalveolar lavage (BAL) fluid was collected from the right lung lobe of 8 animals. BAL differential was performed by staining of BAL cells with fluorochrome-conjugated antibodies to CD45, CD11c and SiglecF. Cells were acquired on flow cytometer (LSR, Becton Dickinson) and the percentage of CD45$^{pos}$SiglecFP$^{pos}$CD11c$^{neg}$(eosinophils) cells was determined. The percentage of eosinophils in BAL was used as a marker of enhanced pathology (FIG. 9).

Figure 9:
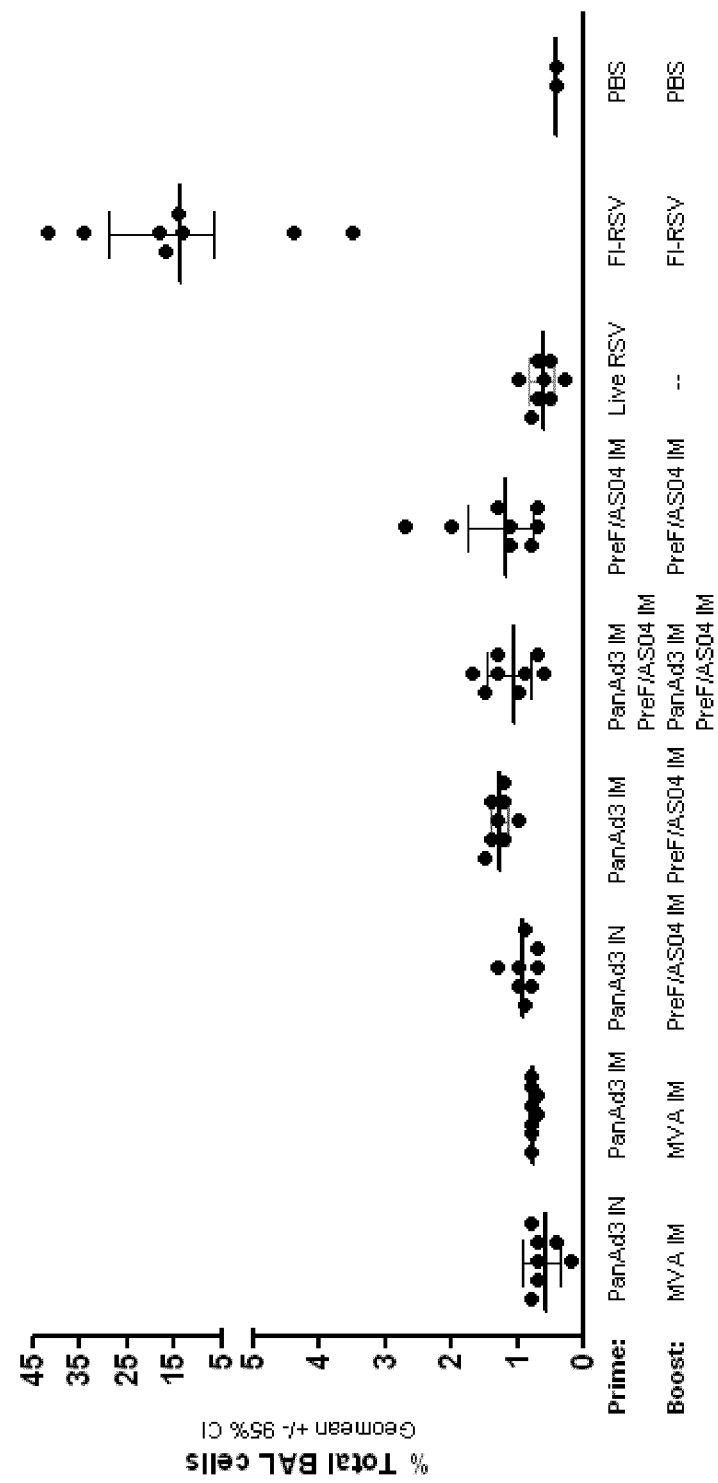
FIG. 9 is a graph illustrating the number of eosinophils in bronchoalveolar lavage (BAL) fluid following challenge of subjects immunized according to various regimens.

FIG. 9 shows that very low levels of eosinophils are observed in the PanAd3 RSV+fF/AS04 co-administration groups as well as in the other vaccine groups with the exception of FI-RSV. Taken together, the data shown in FIGS. 7 to 9 indicate that the concurrent administration vaccine composed of PanAd3 RSV and fF/AS04 is not associated with enhanced pathology upon RSV challenge, as shown by a Th1-skewed lung CD4 T cell response and low levels of mucus-producing cells and eosinophils in the lungs.

Example 5

Concurrent Immunization of Balb/c Mice with An Adenoviral Vector Expressing RSV Proteins and Adjuvanted Recombinant F Protein at Two Protein and Three Adjuvant Doses Induces a Neutralizing Antibody and a T Cell Response, and a Th1 Phenotype in Lung T Cells After RSV Challenge, with Significantly Reduced Lung Viral Load The immunogenicity and effect of vaccination on the Th1/Th2 response of lung CD4 T-cells, lung eosinophilia and mucus production after challenge was evaluated in Balb/c mice with a co-administration regimen comprising an adenovirus vector (Chimpanzee Adenovirus 155; ChAd155-RSV) RSV candidate containing a nucleic acid expressing RSV F, N and M2.1(SEQ ID NO: 4) and adjuvanted protein (PreF, SEQ ID NO:2), at two protein and three alum adjuvant doses. Groups of Balb/c mice (n=15/group) were immunized intra-muscularly, twice at a 3-week interval, with the following formulations concurrently (a few minutes apart):

| Group | Co-administered: Formulation 1 + Formulation 2 |
|---|---|
| 1 | ChAd155-RSV IM 10$^8$vp + PreF protein 2 µg and Alum hydroxide (50 µg) |
| 2 | ChAd155-RSV IM 10$^8$vp + PreF protein 2 µg and Alum hydroxide (17 µg) |
| 3 | ChAd155-RSV IM 10$^8$vp + PreF protein 2 µg and Alum hydroxide (6 µg) |
| 4 | ChAd155-RSV IM 10$^8$vp + PreF protein 0.2 µg and Alum hydroxide (50 µg) |
| 5 | ChAd155-RSV IM 10$^8$vp + PreF protein 0.2 µg and Alum hydroxide (17 µg) |
| 6 | ChAd155-RSV IM 10$^8$vp + PreF protein 0.2 µg and Alum hydroxide (6 µg) |
| 7 | ChAd155-RSV RSV IM 10$^8$vp + PreF protein 2 µg and AS04D (50 µg) |
| 8 | PBS + ChAd155-RSV IM 10$^8$vp |
| 9 | PreF protein 2 µg-and Alum hydroxide (50 µg) + PBS |
| 10 | Alum Adsorbed FI-RSV 1/150 |
| 11 | Live RSV ~3.6 × 10$^6$pfu |
| 12 | PBS + PBS |

Figure 10:
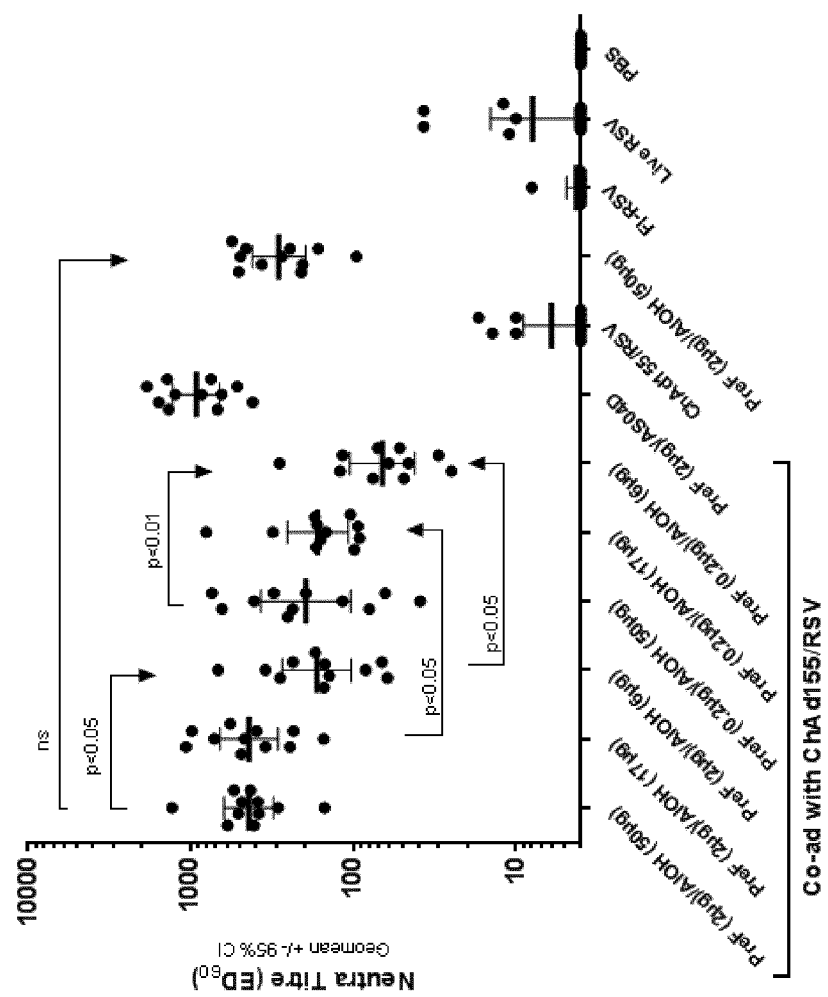
FIG. 10 is a graph illustrating RSV A neutralizing titre following immunization according to various regimens.

Immunogenicity: Sera from 11 mice/group were individually collected on Day 35 (14 days after the second immunization) and tested for the presence of RSV neutralizing antibodies using a plaque reduction assay as described in Example 1. Results are illustrated in FIG. 10. Two doses of a combination vaccine composed of concurrently administered ChAd155-RSV and recombinant F (PreF) protein adjuvanted with either Alum or AS04 induced similar neutralizing antibody titres than 2 doses of protein adjuvanted with 50 µg of Alum, but significantly higher titers than 2 doses of ChAd155-RSV. The combination of ChAd155-RSV and adjuvanted protein allowed reduction of the dose of Alum to 17 µg while maintaining a neutralizing antibody response similar to that of the protein adjuvanted with 50 µg (alone or concurrantly with ChAd155-RSV). A dose response was observed between the 2 µg and 0.2 µg protein doses and the lowest level of Alum (6 µg) resulted in lower titres of neutralizing antibody at both protein doses.

Figure 11:
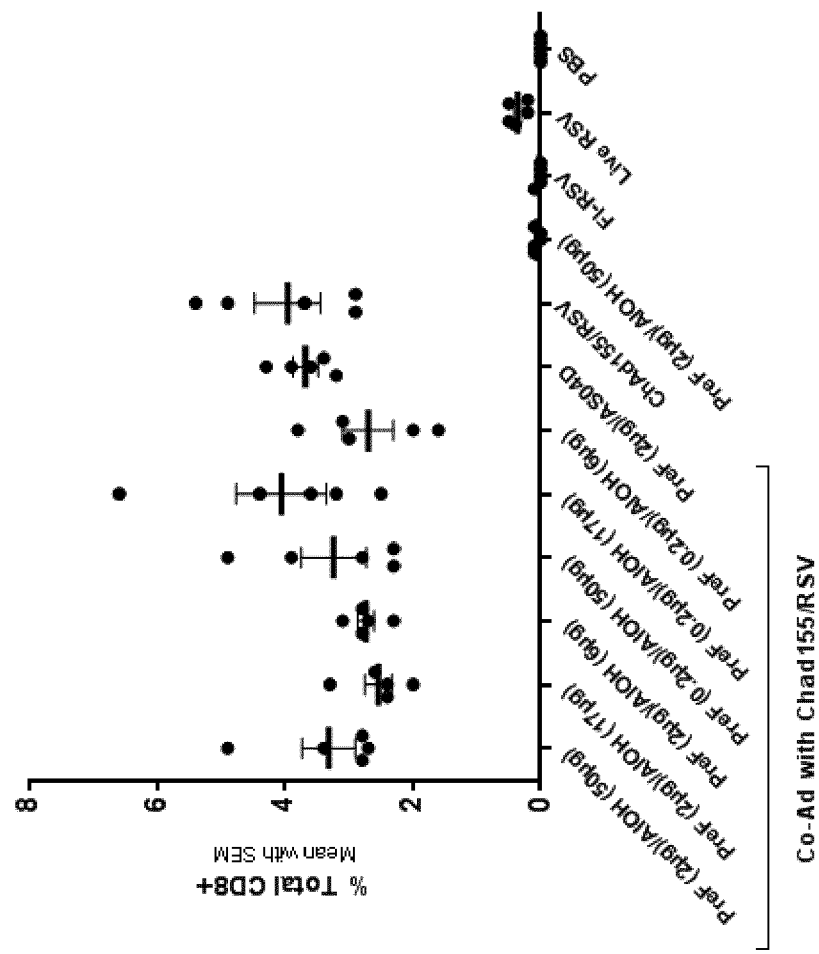
FIG. 11 is a graph illustrating RSV M2-1-specific CD8+ T cells following immunization according to various regimens.

The CD8 T-cell response was measured by identifying M2.1-specific cells in whole blood with a fluorochrome-tagged pentameric major histocompatibility complex (MHC) class I carrying the M2.1 82-90 epitope. To this end, blood was collected from 5 mice/group, 14 days after the second immunization. Red blood cells were lysed, and cells were stained with a fluorescent viability marker, CD3, CD8 and B-220 antibodies and the MHC pentamer. Stained cells were analyzed by flow cytometry (LSR, Beckton Dickinson) and the proportion of pentamer-positive CD8 T-cells was determined (FIG. 11). A similar CD8 response was detected in whole blood T calls in all groups immunized with ChAd155 RSV, but not in the group immunized with PreF protein alone.

Figure 12:
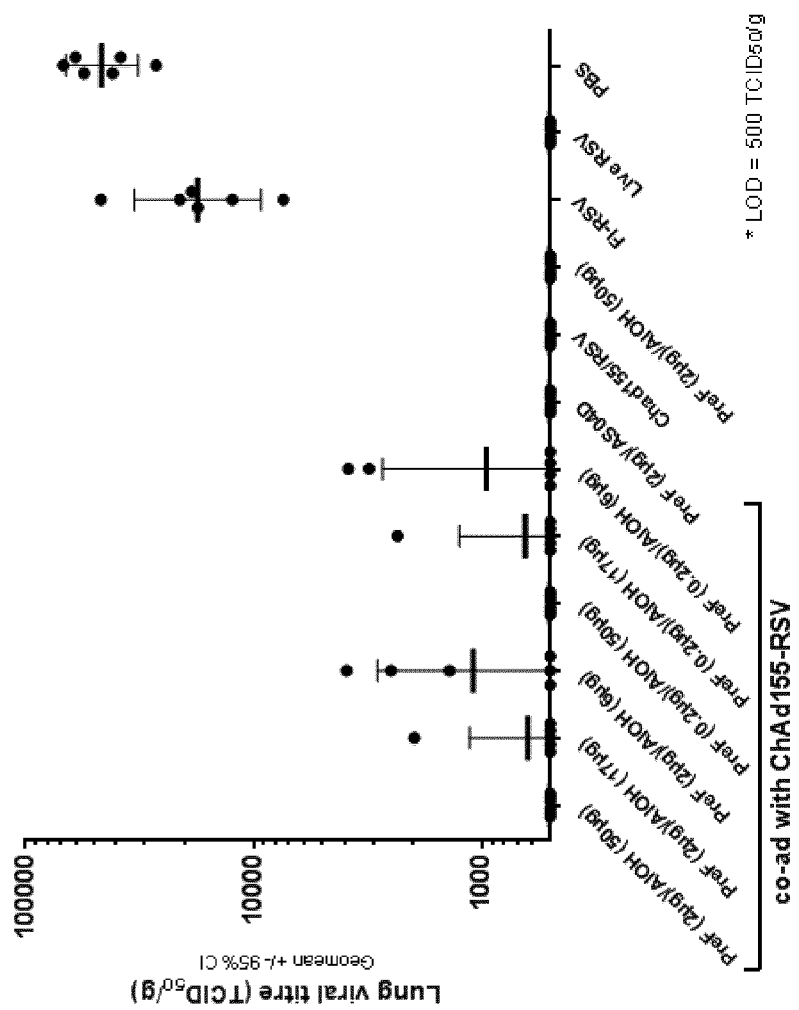
FIG. 12 is a graph illustrating lung viral titre following challenge of subjects immunized according to various regimens.

Response to Challenge: Mice were challenged intranasally with 1-3×10$^6$ pfu live RSV A Long. At day 4 post-challenge, lungs were harvested and individually weighed and homogenized. Serial dilutions (8 replicates each) of each lung homogenate were incubated with Vero cells and wells containing RSV plaques were identified by immunofluorescence, 6 days after seeding. The viral titer was determined using the Spearman-Kärber method for TCID50 calculation and was expressed per gram of lung (FIG. 12). Most animals in the ChAd155-RSV and/or adjuvanted protein groups showed full protection (undetectable viral load in lungs). There was a trend for slightly lower protection with the lowest alum dose.

Figure 13:
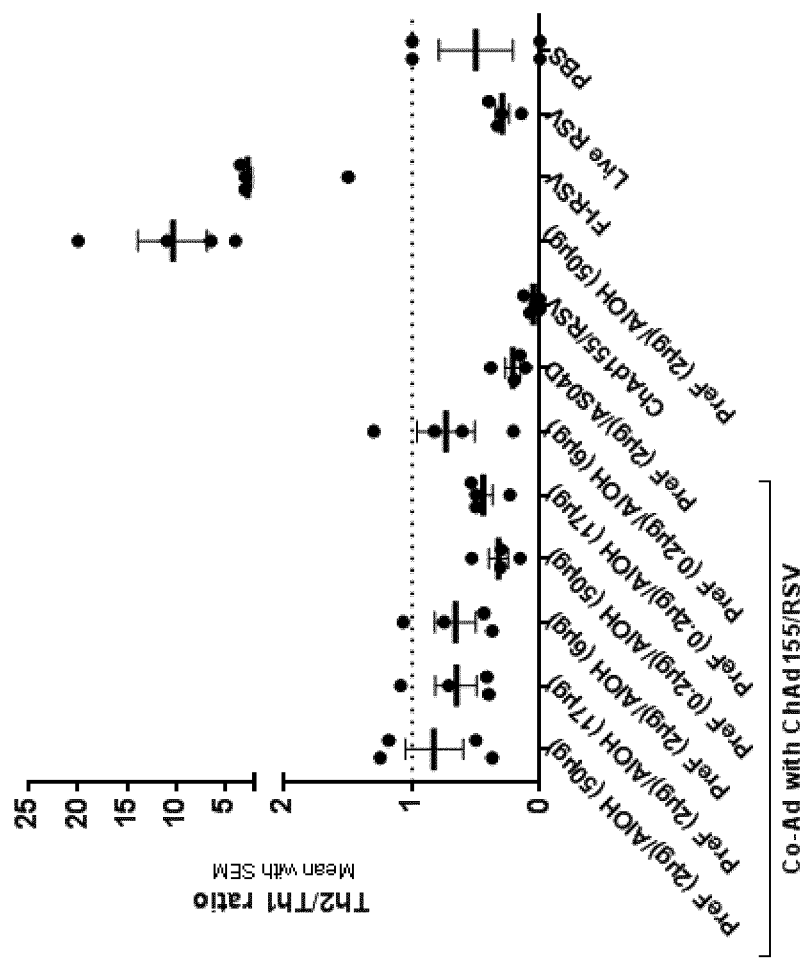
FIG. 13 is a graph illustrating the ratio of Th1 and Th2 T cells following immunization according to various regimens.

Lungs were collected from 4 animals/group at 4 days post-challenge and prepared as described in Example 4. Following restimulation of lymphocytes with pooled peptides from the F antigen, cells were stained for flow cytometry analysis of intracellular cytokines as described in Example 4 and the ratio of Th2/Th1 cells was calculated (FIG. 13). Following restimulation of lung lymphocytes with pooled peptides from the M2.1 antigen carried out in an analogous fashion, the proportion of IFNγ-expressing CD8+ T cells was calculated (FIG. 14).

FIG. 13 shows that ChAd155 RSV+PreF (at all adjuvant doses) shifts the Th2/Th1 ratio towards Th1 when compared to the PreF/Alum formulation (the balanced Th2/Th1 ratio of 1 is indicated by the dotted line) and the choice and dose of adjuvant has little impact. All the vaccine formulations containing ChAd155 RSV+PreF combinations also induce a lower Th2/Th1 ratio than that observed in the FI-RSV group, a vaccine regimen known to induce high levels of CD4 Th2 cells and associated with enhanced RSV disease.

Figure 14:
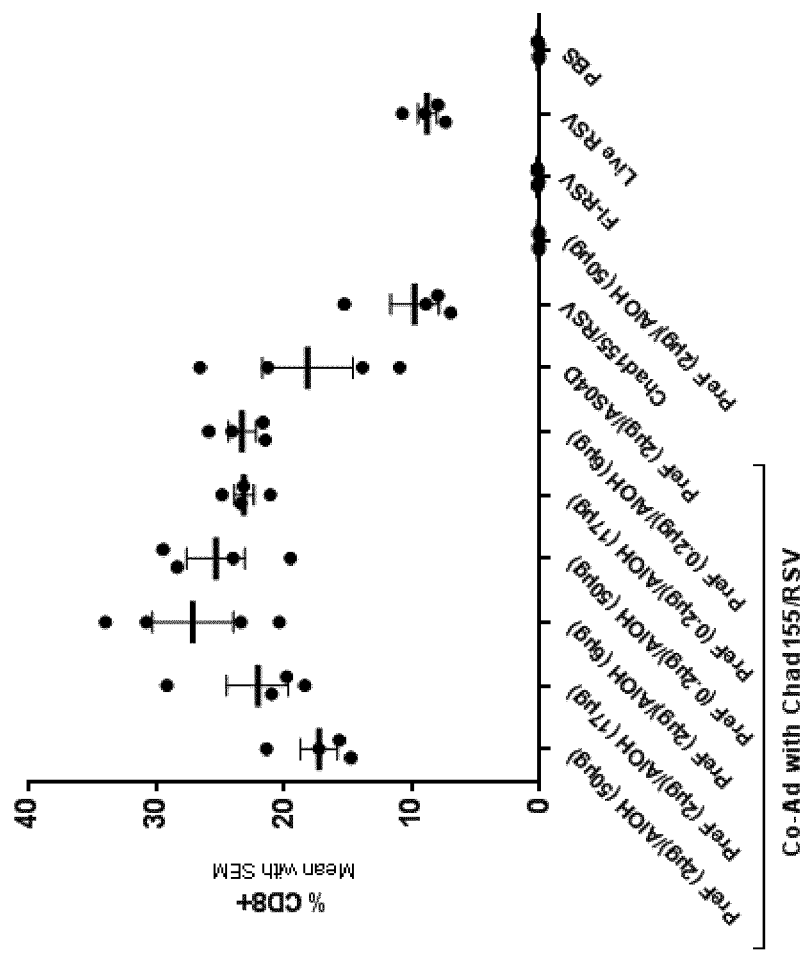
FIG. 14 is a graph illustrating RSV M2-1-specific CD8+ T cells following challenge of subjects immunized according to various regimens.

FIG. 14 shows that high levels of INFg-expressing CD8+ T cells were detected in the lungs of all of the co-administration ChAd155 RSV+PreF groups. At the higher protein dose, reduction in Alum correlated with higher CD8 response, but the adjuvant level had little impact at the lower protein dose. CD8 levels were lower in the lungs of mice immunized with ChAd155 RSV alone than in the co-administration groups, and undetectable in the PreF protein/Alum group.

For histopathology, Periodic Acid Schiff staining was performed to quantify mucus-producing cells on formalin-fixed paraffin-embedded (FFPE) mouse lung tissue sections as described in Example 4. Mucus-producing cells are associated with enhanced RSV pathology induced by FI-RSV in the Balb/c RSV challenge model. The average PAS/mmBM per subject was calculated (FIG. 15).

Figure 15:
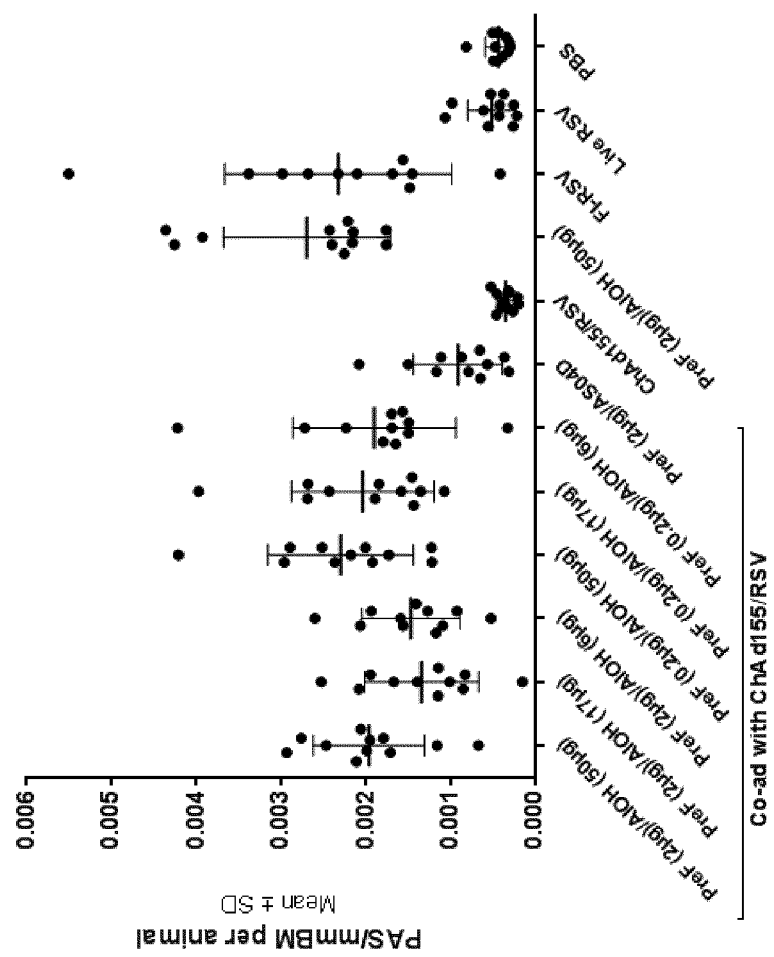
FIG. 15 is a graph illustrating the number of mucus-producing cells in lungs following challenge of subjects immunized according to various regimens.

FIG. 15 shows that the co-administration of ChAd155-RSV with PreF/Alum does not increase the number of mucus-producing cells after RSV challenge when compared to the PreF/Alum formulation. At the higher protein dose, reduction in Alum correlated with lower numbers of mucus-producing cells, but the adjuvant level had less impact at the lower protein dose. The combination of ChAd155-RSV with PreF/AS04D induced lower levels of mucus-producing cells than the equivalent ChAd155-RSV/PreF+Alum combination. The lowest number of mucus-producing cells was seen with ChAd155-RSV administered alone.

The results in FIGS. 10-15 indicate that the concurrent administration vaccine composed of ChAd155 RSV and adjuvanted PreF protein antigen is able to induce protective neutralizing antibody and T cell responses with a Th1/Th2 balanced CD4 response and no enhanced pathology upon RSV challenge.

---

SEQUENCE LISTING

SEQ ID NO: 1: Nucleotide sequence of an exemplary
conformationally constrained PreF antigen.
ATGGAGCTGCTGATCCTGAAAACCAACGCCATCACCGCCATCCTGGCCGC
CGTGACCCTGTGCTTCGCCTCCTCCCAGAACATCACCGAGGAGTTCTACC
AGTCCACCTGCTCCGCCGTGTCCAAGGGCTACCTGTCCGCCCTGCGGACC
GGCTGGTACACCTCCGTGATCACCATCGAGCTGTCCAACATCAAGGAAAA
CAAGTGCAACGGCACCGACGCCAAGGTGAAGCTGATCAAGCAGGAGCTGG
ACAAGTACAAGAGCGCCGTGACCGAACTCCAGCTGCTGATGCAGTCCACC
CCTGCCACCAACAACAAGTTTCTGGGCTTCCTGCAGGGCGTGGGCTCCGC
CATCGCCTCCGGCATCGCCGTGAGCAAGGTGCTGCACCTGGAGGGCGAGG
TGAACAAGATCAAGAGCGCCCTGCTGTCCACCAACAAGGCCGTGGTGTCC
CTGTCCAACGGCGTGTCCGTGCTGACCTCCAAGGTGCTGGATCTGAAGAA
CTACATCGACAAGCAGCTGCTGCCTATCGTGAACAAGCAGTCCTGCTCCA
TCTCCAACATCGAGACCGTGATCGAGTTCCAGCAGAAGAACAACCGGCTG
CTGGAGATCACCCGCGAGTTCTCCGTGAACGCCGGCGTGACCACCCCTGT
GTCCACCTACATGCTGACCAACTCCGAGCTGCTGTCCCTGATCAACGACA
TGCCTATCACCAACGACCAGAAAAAACTGATGTCCAACAACGTGCAGATC
GTGCGGCAGCAGTCCTACAGCATCATGAGCATCATCAAGGAAGAGGTGCT
GGCCTACGTGGTGCAGCTGCCTCTGTACGGCGTGATCGACACCCCTTGCT
GGAAGCTGCACACCTCCCCCCTGTGCACCACCAACACCAAGGAGGGCTCC
AACATCTGCCTGACCCGGACCGACCGGGGCTGGTACTGCGACAACGCCGG
CTCCGTGTCCTTCTTCCCTCTGGCCGAGACCTGCAAGGTGCAGTCCAACC
GGGTGTTCTGCGACACCATGAACTCCCTGACCCTGCCTTCCGAGGTGAAC
CTGTGCAACATCGACATCTTCAACCCCAAGTACGACTGCAAGATCATGAC
CAGCAAGACCGACGTGTCCTCCAGCGTGATCACCTCCCTGGGCGCCATCG
TGTCCTGCTACGGCAAGACCAAGTGCACCGCCTCCAACAAGAACCGGGGA
ATCATCAAGACCTTCTCCAACGGCTGCGACTACGTGTCCAATAAGGGCGT
GGACACCGTGTCCGTGGGCAACACACTGTACTACGTGAATAAGCAGGAGG
GCAAGAGCCTGTACGTGAAGGGCGAGCCTATCATCAACTTCTACGACCCT
CTGGTGTTCCCTTCCGACGAGTTCGACGCCTCCATCAGCCAGGTGAACGA
GAAGATCAACGGGACCCTGGCCTTCATCCGGAAGTCCGACGAGAAGCTGC
ATAACGTGGAGGACAAGATCGAGGAGATCCTGTCCAAAATCTACCACATC
GAGAACGAGATCGCCCGGATCAAGAAGCTGATCGGCGAGGCC SEQ ID NO: 2: Amino acid sequence of an exemplary
conformationally constrained PreF antigen.
MELLILKTNAITAILAAVTLCFASSQNITEEFYQSTCSAVSKGYLSALRT
GWYTSVITIELSNIKENKCNGTDAKVKLIKQELDKYKSAVTELQLLMQST
PATNNKFLGFLQGVGSAIASGIAVSKVLHLEGEVNKIKSALLSTNKAVVS
LSNGVSVLTSKVLDLKNYIDKQLLPIVNKQSCSISNIETVIEFQQKNNRL
LEITREFSVNAGVTTPVSTYMLTNSELLSLINDMPITNDQKKLMSNNVQI
VRQQSYSIMSIIKEEVLAYVVQLPLYGVIDTPCWKLHTSPLCTTNTKEGS
NICLTRTDRGWYCDNAGSVSFFPLAETCKVQSNRVFCDTMNSLTLPSEVN
LCNIDIFNPKYDCKIMTSKTDVSSSVITSLGAIVSCYGKTKCTASNKNRG
IIKTFSNGCDYVSNKGVDTVSVGNTLYYVNKQEGKSLYVKGEPIINFYDP
LVFPSDEFDASISQVNEKINGTLAFIRKSDEKLHNVEDKIEEILSKIYHI
ENEIARIKKLIGEA SEQ ID NO: 3: Nucleotide sequence of an exemplary
nucleic acid that encodes RSV antigens.
ATGGAACTGCTGATCCTGAAGGCCAACGCCATCACCACCATCCTGACCGC
CGTGACCTTCTGCTTCGCCAGCGGCCAGAACATCACCGAGGAATTCTACC
AGAGCACCTGTAGCGCCGTGAGCAAGGGCTACCTGAGCGCCCTGAGAACC
GGCTGGTACACCAGCGTGATCACCATCGAGCTGAGCAACATCAAAGAAAA
CAAGTGCAACGGCACCGACGCCAAAGTGAAGCTGATCAAGCAGGAACTGG
ACAAGTACAAGAACGCCGTGACCGAGCTGCAGCTGCTGATGCAGAGCACC
CCCGCCACCAACAACCGGGCCAGACGGGAGCTGCCCCGGTTCATGAACTA
CACCCTGAACAACGCCAAAAAGACCAACGTGACCCTGAGCAAGAAGCGGA
AGCGGCGGTTCCTGGGCTTTCTGCTGGGCGTGGGCAGCGCCATTGCCAGC
GGCGTGGCCGTGTCTAAGGTGCTGCACCTGGAAGGCGAAGTGAACAAGAT
CAAGAGCGCCCTGCTGAGCACCAACAAGGCCGTGGTGTCCCTGAGCAACG
GCGTGAGCGTGCTGACCAGCAAGGTGCTGGATCTGAAGAACTACATCGAC
AAGCAGCTGCTGCCCATCGTGAACAAGCAGAGCTGCAGCATCAGCAACAT
CGAGACAGTGATCGAGTTCCAGCAGAAGAACAACCGGCTGCTGGAAATCA
CCCGGGAGTTCAGCGTGAACGCCGGCGTGACCACCCCTGTGTCCACCTAC
ATGCTGACCAACAGCGAGCTGCTGAGCCTGATCAACGACATGCCCATCAC
CAACGACCAGAAAAAGCTGATGAGCAACAACGTGCAGATCGTGCGGCAGC
AGAGCTACTCCATCATGTCCATCATCAAAGAAGAGGTGCTGGCCTACGTG
GTGCAGCTGCCCCTGTACGGCGTGATCGACACCCCCTGCTGGAAGCTGCA
CACCAGCCCCCTGTGCACCACCAACACCAAAGAGGGCAGCAACATCTGCC
TGACCCGGACCGACAGAGGCTGGTACTGCGACAACGCCGGCAGCGTGTCA
TTCTTTCCACAGGCCGAGACATGCAAGGTGCAGGACAACCGGGTTCTG
CGACACCATGAACAGCCTGACCCTGCCCTCCGAAGTGAACCTGTGCAACG
TGGACATCTTCAACCCCAAGTACGACTGCAAGATCATGACCTCCAAGACC
GACGTGTCCAGCTCCGTGATCACCTCCCTGGGCGCCATCGTGTCCTGCTA
CGGCAAGACCAAGTGCACCGCCAGCAACAAGAACCGGGGCATCATCAAGA
CCTTCAGCAACGGCTGCGACTACGTGTCCAACAAGGGGGTGGACACCGTG
TCCGTGGGCAACACCCTGTACTACGTGAACAAACAGGAAGGCAAGAGCCT
GTACGTGAAGGGCGAGCCCATCATCAACTTCTACGACCCCCTGGTGTTCC
CCAGCGACGAGTTCGACGCCAGCATCAGCCAGGTGAACGAGAAGATCAAC
CAGAGCCTGGCCTTCATCCGGAAGTCCGACGAGCTGCTGCACAATGTGAA
TGCCGGCAAGTCCACCACCAACCGGAAGCGGAGAGCCCTGTGAAGCAGA
CCCTGAACTTCGACCTGCTGAAGCTGGCCGGCGACGTGGAGAGCAATCCC
GGCCCTATGGCCCTGAGCAAAGTGAAACTGAACGATACACTGAACAAGGA
CCAGCTGCTGTCCAGCAGCAAGTACACCATCCAGCGGAGCACCGGCGACA
GCATCGATACCCCCAACTACGACGTGCAGAAGCACATCAACAAGCTGTGC
GGCATGCTGCTGATCACAGAGGACGCCAACCACAAGTTCACCGGCCTGAT
CGGCATGCTGTACGCCATGAGCCGGCTGGGCCGGGAGGACACCATCAAGA
TCCTGCGGGACGCCGGCTACCACGTGAAGGCCAATGGCGTGGACGTGACC
ACACACCGGCAGGACATCAACGGCAAAGAAATGAAGTTCGAGGTGCTGAC
CCTGGCCAGCCTGACCACCGAGATCCAGATCAATATCGAGATCGAGAGCC
GGAAGTCCTACAAGAAAATGCTGAAAGAAATGGGCGAGGTGGCCCCCGAG
TACAGACACGACAGCCCCGACTGCGGCATGATCATCCTGTGTATCGCCGC
CCTGGTGATCACAAAGCTGGCCGCTGGCGACAGATCTGGCCTGACAGCCG
TGATCAGACGGGCCAACAATGTGCTGAAGAACGAGATGAAGCGGTACAAG
GGCCTGCTGCCCAAGGACATTGCCAACAGCTTCTACGAGGTGTTCGAGAA
GTACCCCCACTTCATCGACGTGTTCGTGCACTTCGGCATTGCCCAGAACA
GCACCAGAGGCGGCTCCAGAGTGGAGGGCATCTTCGCCGGCCTGTTCATG
AACGCCTACGGCGCTGGCCAGGTGATGCTGAGATGGGGCGTGCTGGCCAA
GAGCGTGAAGAACATCATGCTGGGCCACGCCAGCGTGCAGGCCGAGATGG
AACAGGTGGTGGAGGTGTACGAGTACGCCCAGAAGCTGGGCGGAGAGGCC
GGCTTCTACCACATCCTGAACAACCCTAAGGCCTCCCTGCTGTCCCTGAC
CCAGTTCCCCCACTTCTCCAGCGTGGTGCTGGGAAATGCCGCCGGACTGG
GCATCATGGGCGAGTACCGGGGCACCCCCAGAAACCAGGACCTGTACGAC
GCCGCCAAGGCCTACGCCGAGCAGCTGAAAGAAAACGGCGTGATCAACTA
CAGCGTGCTGGACCTGACCGCTGAGGAACTGGAAGCCATCAAGCACCAGC
TGAACCCCAAGGACAACGACGTGGAGCTGGGAGGCGGAGGATCTGGCGGC
GGAGGCATGAGCAGACGGAACCCCTGCAAGTTCGAGATCCGGGGCCACTG
CCTGAACGGCAAGCGGTGCCACTTCAGCCACAACTACTTCGAGTGGCCCC
CTCATGCTCTGCTGGTGCGGCAGAACTTCATGCTGAACCGGATCCTGAAG
TCCATGGACAAGAGCATCGACACCCTGAGCGAGATCAGCGGAGCCGCCGA
GCTGGACAGAACCGAGGAATATGCCCTGGGCGTGGTGGGAGTGCTGGAAA
GCTACATCGGCTCCATCAACAACATCACAAAGCAGAGCGCCTGCGTGGCC
ATGAGCAAGCTGCTGACAGAGCTGAACAGCGACGACATCAAGAAGCTGAG
GGACAACGAGGAACTGAACAGCCCCAAGATCCGGGTGTACAACACCGTGA
TCAGCTACATTGAGAGCAACCGCAAGAACAACAAGCAGACCATCCATCTG
CTGAAGCGGCTGCCCGCCGACGTGCTGAAAAAGACCATCAAGAACACCCT
GGACATCCACAAGTCCATCACCATCAACAATCCCAAAGAAAGCACCGTGT
CTGACACCAACGATCACGCCAAGAACAACGACACCACC SEQ ID NO: 4: Amino acid sequence of an exemplary
nucleic acid that encodes RSV antigens.
MELLILKANAITTILTAVTFCFASGQNITEEFYQSTCSAVSKGYLSALRT
GWYTSVITIELSNIKENKCNGTDAKVKLIKQELDKYKNAVTELQLLMQST
PATNNRARRELPRFMNYTLNNAKKTNVTLSKKRKRRFLGFLLGVGSAIAS

SEQUENCE LISTING

```
GVAVSKVLHLEGEVNKIKSALLSTNKAVVSLSNGVSVLTSKVLDLKNYID
KQLLPIVNKQSCSISNIETVIEFQQKNNRLLEITREFSVNAGVTTPVSTY
MLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVS
FFPQAETCKVQSNRVFCDTMNSLTLPSEVNLCNVDIFNPKYDCKIMTSKT
DVSSSVITSLGAIVSCYGKTKCTASNKNRGIIKTFSNGCDYVSNKGVDTV
SVGNTLYYVNKQEGKSLYVKGEPIINPYDPLVFPSDEFDASISQVNEKIN
QSLAFIRKSDELLHNVNAGKSTTNRKRRAPVKQTLNFDLLKLAGDVESNP
GPMALSKVKLNDTLNKDQLLSSSKYTIQRSTGDSIDTPNYDVQKHINKLC
GMLLITEDANHKFTGLIGMLYAMSRLGREDTIKILRDAGYHVKANGVDVT
THRQDINGKEMKFEVLTLASLTTEIQINIEIESRKSYKKMLKEMGEVAPE
YRHDSPDCGMIILCIAALVITKLAAGDRSGLTAVIRRANNVLKNEMKRYK
GLLPKDIANSFYEVFEKYPHFIDVFVHFGIAQSSTRGGSRVEGIFAGLFM
NAYGAGQVMLRWGVLAKSVKNIMLGHASVQAMEQVVEVYEYAQKLGGEA
GFYHILNNPKASLLSLTQFPHFSSVVLGNAAGLGIMGEYRGTPRNQDLYD
AAKAYAEQLKENGVINYSVLDLTAEELEAIKHQLNPKDNDVELGGGGSGG
GGMSRRNPCKFEIRGHCLNGKRCHFSHNYFEWPPHALLVRQNFMLNRILK
SMDKSIDTLSEISGAAELDRTEEYALGVVGVLESYIGSINNITKQSACVA
MSKLLTELNSDDIKKLRDNEELNSPKIRVYNTVISYIESNRKNNKQTIHL
LKRLPADVLKKTIKNTLDIHKSITINNPKESTVSDTNDHAKNNDTT

Positions 1-524   = FΔTM protein

Positions 525-552 = 2a sequence

Positions 553-943 = N protein

Positions 944-1146 = M2-1 protein
```

We claim:

1. An immunogenic combination of compositions comprising:
a) a first immunogenic composition comprising an F protein antigen of respiratory syncytial virus (RSV), wherein the F protein antigen is constrained in the pre-fusion conformation, wherein the first immunogenic composition comprises a polypeptide with the amino acid sequence represented by: (i) a polypeptide with at least 95% sequence identity to SEQ ID NO:2; or (ii) a polypeptide comprising SEQ ID NO:2; and b) a second immunogenic composition comprising an adenoviral vector comprising a nucleic acid encoding an RSV FΔTM antigen and RSV M2-1 and N antigens of respiratory syncytial virus (RSV);

wherein the first immunogenic composition and the second immunogenic composition are formulated for concurrent administration, and wherein the first immunogenic composition, or the second immunogenic composition, or both further comprise an adjuvant.

2. The immunogenic combination of claim 1, wherein the antigens of the first and second immunogenic compositions comprise one or more identical immunogenic epitopes.

3. The immunogenic combination of claim 1, wherein the first and at least second immunogenic composition comprise a plurality of antigens.

4. The immunogenic combination of claim 1, wherein a self-cleavage site is included between the RSV FΔTM antigen and the RSV M2-1 and a flexible linker is included between the RSV M2-1 and N antigens.

5. The immunogenic combination of claim 1, wherein the first and second immunogenic compositions are formulated in different compositions.

6. The immunogenic combination of claim 1, wherein the first and second immunogenic compositions are formulated in a single composition (co-formulated).

7. The immunogenic combination of claim 1 wherein the adjuvant is selected from the group consisting of a metallic salt, 3-D-monophosphoryl-lipid-A (MPL), a saponin, and an oil and water emulsion, a liposome and a nanoparticle.

8. The immunogenic combination of claim 7, wherein the metallic salt is (i) an aluminum salt selected from the group consisting of: aluminum hydroxide, aluminum potassium sulfate, aluminum hydroxyphosphate sulfate, and aluminum phosphate, or (ii) a calcium salt selected from the group consisting of calcium phosphate and calcium fluoride.

9. A method for eliciting an immune response specific for respiratory syncytial virus (RSV) in a subject, the method comprising a step of administering the immunogenic combination of claim 1 to the subject.

10. A method for preventing, reducing, or treating an infection by respiratory syncytial virus (RSV) in a subject comprising a step of administering the immunogenic combination of claim 1 to the subject.

11. A process for making the immunogenic combination of claim 1 comprising a step of formulating a first immunogenic composition comprising an F protein antigen of respiratory syncytial virus (RSV), wherein the F protein antigen is constrained in the pre-fusion conformation and a second immunogenic composition comprising an adenoviral vector comprising a nucleic acid encoding an RSV FΔTM antigen and RSV M2-1 and N antigens of respiratory syncytial virus (RSV) for concurrent administration, wherein the first immunogenic composition comprises a polypeptide with the amino acid sequence represented by: (i) a polypeptide with at least 95% sequence identity to SEQ ID NO:2; or (ii) a polypeptide comprising SEQ ID NO:2.

12. A method of vaccination for the prevention, reduction or treatment of infection by respiratory syncytial virus (RSV), comprising a step of concurrently administering an immunogenic combination of claim 1.

13. The immunogenic combination of claim 1, wherein the second immunogenic composition comprises a nucleic acid which encodes an amino acid represented by SEQ ID NO:4.

\* \* \* \* \*

UNITED STATES PATENT AND TRADEMARK OFFICE
CERTIFICATE OF CORRECTION

PATENT NO. : 11,571,472 B2
APPLICATION NO. : 15/318490
DATED : February 7, 2023
INVENTOR(S) : Ann-Muriel Steff et al.

It is certified that error appears in the above-identified patent and that said Letters Patent is hereby corrected as shown below:

In the Claims

Claim 1, Column 55, Line 3:
Change: "an RSV FATM antigen and RSV M2-1and N antigens"
To: -- an RSV FΔTM antigen and RSV M2-1 and N antigens --

Claim 11, Column 56, Line 17:
Change: "vector comprising a nucleic acid encoding an RSV FATM"
To: -- vector comprising a nucleic acid encoding an RSV FΔTM --

Signed and Sealed this
Eighteenth Day of April, 2023

Katherine Kelly Vidal
*Director of the United States Patent and Trademark Office*

SEQUENCE LISTING

<160> NUMBER OF SEQ ID NOS: 4

<210> SEQ ID NO 1
<211> LENGTH: 1542
<212> TYPE: DNA
<213> ORGANISM: Respiratory syncytial virus

<400> SEQUENCE: 1

```
atggagctgc tgatcctgaa aaccaacgcc atcaccgcca tcctggccgc cgtgaccctg      60
tgcttcgcct cctcccagaa catcaccgag gagttctacc agtccacctg ctccgccgtg     120
tccaagggct acctgtccgc cctgcggacc ggctggtaca cctccgtgat caccatcgag     180
ctgtccaaca tcaaggaaaa caagtgcaac ggcaccgacg ccaaggtgaa gctgatcaag     240
caggagctgg acaagtacaa gagcgccgtg accgaactcc agctgctgat gcagtccacc     300
cctgccacca caacaagtt tctgggcttc ctgcagggcg tgggctccgc catcgcctcc     360
ggcatcgccg tgagcaaggt gctgcacctg gagggcgagg tgaacaagat caagagcgcc     420
ctgctgtcca ccaacaaggc cgtggtgtcc ctgtccaacg gcgtgtccgt gctgacctcc     480
aaggtgctga tctgaagaa ctacatcgac aagcagctgc tgcctatcgt gaacaagcag     540
tcctgctcca tctccaacat cgagaccgtg atcgagttcc agcagaagaa caaccggctg     600
ctggagatca cccgcgagtt ctccgtgaac gccggcgtga ccacccctgt gtccacctac     660
atgctgacca actccgagct gctgtccctg atcaacgaca tgcctatcac caacgaccag     720
aaaaaactga tgtccaacaa cgtgcagatc gtgcggcagc agtcctacag catcatgagc     780
atcatcaagg aagaggtgct ggcctacgtg gtgcagctgc ctctgtacgg cgtgatcgac     840 acccccttgct ggaagctgca cacctccccc ctgtgcacca ccaacaccaa ggagggctcc     900
aacatctgcc tgacccggac cgaccggggc tggtactgcg acaacgccgg ctccgtgtcc     960
ttcttccctc tggccgagac ctgcaaggtg cagtccaacc gggtgttctg cgacaccatg    1020 aactcctga ccctgcctc cgaggtgaac ctgtgcaaca tcgacatctt caaccccaag    1080
tacgactgca agatcatgac cagcaagacc gacgtgtcct ccagcgtgat cacctccctg    1140
ggcgccatcg tgtcctgcta cggcaagacc aagtgcaccg cctccaacaa gaaccgggga    1200
atcatcaaga ccttctccaa cggctgcgac tacgtgtcca ataagggcgt ggacaccgtg    1260
tccgtgggca cacactgtta ctacgtgaat aagcaggagg caagagcct gtacgtgaag    1320 ggcgagccta tcatcaactt ctacgaccct ctggtgttcc cttccgacga gttcgacgcc    1380
tccatcagcc aggtgaacga gaagatcaac ggaccctgg ccttcatccg gaagtccgac    1440
```
gagaagctgc ataacgtgga ggacaagatc gaggagatcc tgtccaaaat ctaccacatc  1500
gagaacgaga tcgcccggat caagaagctg atcggcgagg cc  1542

<210> SEQ ID NO 2
<211> LENGTH: 514
<212> TYPE: PRT
<213> ORGANISM: Respiratory syncytial virus

<400> SEQUENCE: 2

Met Glu Leu Leu Ile Leu Lys Thr Asn Ala Ile Thr Ala Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Ser Ala Val Thr Glu Leu Gln Leu Leu
                85                  90                  95

Met Gln Ser Thr Pro Ala Thr Asn Asn Lys Phe Leu Gly Phe Leu Gln
            100                 105                 110

Gly Val Gly Ser Ala Ile Ala Ser Gly Ile Ala Val Ser Lys Val Leu
        115                 120                 125

His Leu Glu Gly Glu Val Asn Lys Ile Lys Ser Ala Leu Leu Ser Thr
    130                 135                 140

Asn Lys Ala Val Val Ser Leu Ser Asn Gly Val Ser Val Leu Thr Ser
145                 150                 155                 160

Lys Val Leu Asp Leu Lys Asn Tyr Ile Asp Lys Gln Leu Leu Pro Ile
                165                 170                 175

Val Asn Lys Gln Ser Cys Ser Ile Ser Asn Ile Glu Thr Val Ile Glu
            180                 185                 190

Phe Gln Gln Lys Asn Asn Arg Leu Leu Glu Ile Thr Arg Glu Phe Ser
        195                 200                 205

Val Asn Ala Gly Val Thr Thr Pro Val Ser Thr Tyr Met Leu Thr Asn
    210                 215                 220

Ser Glu Leu Leu Ser Leu Ile Asn Asp Met Pro Ile Thr Asn Asp Gln
225                 230                 235                 240

Lys Lys Leu Met Ser Asn Asn Val Gln Ile Val Arg Gln Gln Ser Tyr
                245                 250                 255

Ser Ile Met Ser Ile Ile Lys Glu Glu Val Leu Ala Tyr Val Val Gln
            260                 265                 270

Leu Pro Leu Tyr Gly Val Ile Asp Thr Pro Cys Trp Lys Leu His Thr
        275                 280                 285

Ser Pro Leu Cys Thr Thr Asn Thr Lys Glu Gly Ser Asn Ile Cys Leu
    290                 295                 300

Thr Arg Thr Asp Arg Gly Trp Tyr Cys Asp Asn Ala Gly Ser Val Ser
305                 310                 315                 320

Phe Phe Pro Leu Ala Glu Thr Cys Lys Val Gln Ser Asn Arg Val Phe
                325                 330                 335

Cys Asp Thr Met Asn Ser Leu Thr Leu Pro Ser Glu Val Asn Leu Cys
            340                 345                 350

```
Asn Ile Asp Ile Phe Asn Pro Lys Tyr Asp Cys Lys Ile Met Thr Ser
            355                 360                 365
Lys Thr Asp Val Ser Ser Val Ile Thr Ser Leu Gly Ala Ile Val
    370                 375                 380
Ser Cys Tyr Gly Lys Thr Lys Cys Thr Ala Ser Asn Lys Asn Arg Gly
385                 390                 395                 400
Ile Ile Lys Thr Phe Ser Asn Gly Cys Asp Tyr Val Ser Asn Lys Gly
                405                 410                 415
Val Asp Thr Val Ser Val Gly Asn Thr Leu Tyr Tyr Val Asn Lys Gln
            420                 425                 430
Glu Gly Lys Ser Leu Tyr Val Lys Gly Glu Pro Ile Ile Asn Phe Tyr
        435                 440                 445
Asp Pro Leu Val Phe Pro Ser Asp Glu Phe Asp Ala Ser Ile Ser Gln
        450                 455                 460
Val Asn Glu Lys Ile Asn Gly Thr Leu Ala Phe Ile Arg Lys Ser Asp
465                 470                 475                 480
Glu Lys Leu His Asn Val Glu Asp Lys Ile Glu Ile Leu Ser Lys
                485                 490                 495
Ile Tyr His Ile Glu Asn Glu Ile Ala Arg Ile Lys Lys Leu Ile Gly
            500                 505                 510
Glu Ala
```

<210> SEQ ID NO 3
<211> LENGTH: 3438
<212> TYPE: DNA
<213> ORGANISM: Respiratory syncytial virus

<400> SEQUENCE: 3

```
atggaactgc tgatcctgaa ggccaacgcc atcaccacca tcctgaccgc cgtgaccttc    60
tgcttcgcca gcggccagaa catcaccgag gaattctacc agagcacctg tagcgccgtg   120
agcaagggct acctgagcgc cctgagaacc ggctggtaca ccagcgtgat caccatcgag   180
ctgagcaaca tcaaagaaaa caagtgcaac ggcaccgacg ccaaagtgaa gctgatcaag   240
caggaactgg acaagtacaa gaacgccgtg accgagctgc agctgctgat gcagagcacc   300
cccgccacca acaaccgggc cagacgggag ctgccccggt tcatgaacta caccctgaac   360
aacgccaaaa agaccaacgt gaccctgagc aagaagcgga gcggcggtt cctgggcttt   420
ctgctgggcg tgggcagcgc cattgccagc ggcgtggccg tgtctaaggt gctgcacctg   480
gaaggcgaag tgaacaagat caagagcgcc ctgctgagca ccaacaaggc cgtggtgtcc   540
ctgagcaacg gcgtgagcgt gctgaccagc aaggtgctgg atctgaagaa ctacatcgac   600
aagcagctgc tgcccatcgt gaacaagcag agctgcagca tcagcaacat cgagacagtg   660
atcgagttcc agcagaagaa caaccggctg ctggaaatca cccgggagtt cagcgtgaac   720
gccggcgtga ccacccctgt gtccacctac atgctgacca cagcgagct gctgagcctg   780
atcaacgaca tgcccatcac caacgaccag aaaaagctga tgagcaacaa cgtgcagatc   840
gtgcggcagc agagctactc catcatgtcc atcatcaaag aagaggtgct ggcctacgtg   900
gtgcagctgc ccctgtacgg cgtgatcgac acccccgct ggaagctgca caccagcccc   960
ctgtgcacca ccaacaccaa agagggcagc aacatctgcc tgacccggac cgacagaggc  1020
tggtactgcg acaacgccgg cagcgtgtca ttctttccac aggccgagac atgcaaggtg  1080
cagagcaacc gggtgttctg cgacaccatg aacagcctga cctgccctc cgaagtgaac  1140
ctgtgcaacg tggacatctt caaccccaag tacgactgca agatcatgac ctccaagacc  1200
```

```
gacgtgtcca gctccgtgat cacctccctg ggcgccatcg tgtcctgcta cggcaagacc    1260
aagtgcaccg ccagcaacaa gaaccggggc atcatcaaga ccttcagcaa cggctgcgac    1320
tacgtgtcca acaagggggt ggacaccgtg tccgtgggca caccctgta ctacgtgaac     1380 aaacaggaag gcaagagcct gtacgtgaag ggcgagccca tcatcaactt ctacgacccc    1440
ctggtgttcc ccagcgacga gttcgacgcc agcatcagcc aggtgaacga gaagatcaac    1500
cagagcctgg ccttcatccg gaagtccgac gagctgctgc acaatgtgaa tgccggcaag    1560
tccaccacca accggaagcg gagagcccct gtgaagcaga ccctgaactt cgacctgctg    1620
aagctggccg cgacgtggaa gagcaatccc ggccctatgg ccctgagcaa agtgaaactg    1680
aacgatacac tgaacaagga ccagctgctg tccagcagca agtacaccat ccagcggagc    1740
accggcgaca gcatcgatac ccccaactac gacgtgcaga gcacatcaa caagctgtgc     1800 ggcatgctgc tgatcacaga ggacgccaac cacaagttca ccggcctgat cggcatgctg    1860
tacgccatga gccggctggg ccgggaggac accatcaaga tcctgcggga cgccggctac    1920
cacgtgaagg ccaatggcgt ggacgtgacc acacaccggc aggacatcaa cggcaaagaa    1980
atgaagttcg aggtgctgac cctggccagc ctgaccaccg agatccagat caatatcgag    2040
atcgagagcc ggaagtccta caagaaaatg ctgaagaaa tgggcgaggt ggcccccgag     2100
tacagacacg cagccccga ctgcggcatg atcatcctgt gtatcgccgc cctggtgatc      2160
acaaagctgg ccgctggcga cagatctggc ctgacagccg tgatcagacg ggccaacaat    2220
gtgctgaaga cgagatgaa gcggtacaag ggcctgctgc ccaaggacat tgccaacagc     2280
ttctacgagg tgttcgagaa gtaccccac ttcatcgacg tgttcgtgca cttcggcatt     2340
gcccagagca gcaccagagg cggctccaga gtggagggca tcttcgccgg cctgttcatg    2400
aacgcctacg cgctggcca ggtgatgctg agatggggcg tgctggccaa gagcgtgaag     2460
aacatcatgc tgggccacgc cagcgtgcag gccgagatgg aacaggtggt ggaggtgtac    2520
gagtacgccc agaagctggg cggagaggcc ggcttctacc acatcctgaa caacccctaag   2580 gcctccctgc tgtccctgac ccagttcccc cacttctcca gcgtggtgct gggaaatgcc    2640
gccggactgg gcatcatggg cgagtaccgg ggcacccca gaaaccagga cctgtacgac     2700
gccgccaagg cctacgccga gcagctgaaa gaaaacggcg tgatcaacta cagcgtgctg    2760
gacctgaccg ctgaggaact ggaagccatc aagcaccagc tgaaccccaa ggacaacgac    2820
gtggagctgg gaggcggagg atctggcggc ggaggcatga gcagacggaa ccctgcaag     2880 ttcgagatcc ggggccactg cctgaacggc aagcggtgcc acttcagcca caactacttc    2940
gagtggcccc tcatgctctc tgctggtgcgg cagaacttca tgctgaaccg gatcctgaag   3000
tccatggaca gagcatcga caccctgagc gagatcagcg gagccgccga gctggacaga    3060
accgaggaat atgccctggg cgtggtggga gtgctggaaa gctacatcgg ctccatcaac    3120
aacatcacaa agcagagcgc ctgcgtggcc atgagcaagc tgctgacaga gctgaacagc    3180
gacgacatca gaagctgag ggacaacgag gaactgaaca gccccaagat ccgggtgtac     3240
aacaccgtga tcagctacat tgagagcaac cgcaagaaca acaagcagac catccatctg    3300
ctgaagcggc tgcccgccga cgtgctgaaa aagaccatca gaacaccct ggacatccac     3360 aagtccatca ccatcaacaa tcccaaagaa agcaccgtgt ctgacaccaa cgatcacgcc    3420
aagaacaacg acaccacc                                                 3438
```

<210> SEQ ID NO 4
<211> LENGTH: 1146
<212> TYPE: PRT
<213> ORGANISM: Respiratory syncytial virus

<400> SEQUENCE: 4

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365
```

```
Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Arg Lys Arg Arg
    515                 520                 525

Ala Pro Val Lys Gln Thr Leu Asn Phe Asp Leu Leu Lys Leu Ala Gly
530                 535                 540

Asp Val Glu Ser Asn Pro Gly Pro Met Ala Leu Ser Lys Val Lys Leu
545                 550                 555                 560

Asn Asp Thr Leu Asn Lys Asp Gln Leu Leu Ser Ser Lys Tyr Thr
                565                 570                 575

Ile Gln Arg Ser Thr Gly Asp Ser Ile Asp Thr Pro Asn Tyr Asp Val
            580                 585                 590

Gln Lys His Ile Asn Lys Leu Cys Gly Met Leu Leu Ile Thr Glu Asp
    595                 600                 605

Ala Asn His Lys Phe Thr Gly Leu Ile Gly Met Leu Tyr Ala Met Ser
    610                 615                 620

Arg Leu Gly Arg Glu Asp Thr Ile Lys Ile Leu Arg Asp Ala Gly Tyr
625                 630                 635                 640

His Val Lys Ala Asn Gly Val Asp Val Thr Thr His Arg Gln Asp Ile
                645                 650                 655

Asn Gly Lys Glu Met Lys Phe Glu Val Leu Thr Leu Ala Ser Leu Thr
            660                 665                 670

Thr Glu Ile Gln Ile Asn Ile Glu Ile Glu Ser Arg Lys Ser Tyr Lys
    675                 680                 685

Lys Met Leu Lys Glu Met Gly Glu Val Ala Pro Glu Tyr Arg His Asp
    690                 695                 700

Ser Pro Asp Cys Gly Met Ile Ile Leu Cys Ile Ala Ala Leu Val Ile
705                 710                 715                 720

Thr Lys Leu Ala Ala Gly Asp Arg Ser Gly Leu Thr Ala Val Ile Arg
                725                 730                 735

Arg Ala Asn Asn Val Leu Lys Asn Glu Met Lys Arg Tyr Lys Gly Leu
            740                 745                 750

Leu Pro Lys Asp Ile Ala Asn Ser Phe Tyr Glu Val Phe Glu Lys Tyr
    755                 760                 765

Pro His Phe Ile Asp Val Phe Val His Phe Gly Ile Ala Gln Ser Ser
    770                 775                 780
```

-continued

Thr Arg Gly Gly Ser Arg Val Glu Gly Ile Phe Ala Gly Leu Phe Met
785             790             795             800

Asn Ala Tyr Gly Ala Gly Gln Val Met Leu Arg Trp Gly Val Leu Ala
        805             810             815

Lys Ser Val Lys Asn Ile Met Leu Gly His Ala Ser Val Gln Ala Glu
        820             825             830

Met Glu Gln Val Val Glu Val Tyr Glu Tyr Ala Gln Lys Leu Gly Gly
        835             840             845

Glu Ala Gly Phe Tyr His Ile Leu Asn Asn Pro Lys Ala Ser Leu Leu
850             855             860

Ser Leu Thr Gln Phe Pro His Phe Ser Ser Val Val Leu Gly Asn Ala
865             870             875             880

Ala Gly Leu Gly Ile Met Gly Glu Tyr Arg Gly Thr Pro Arg Asn Gln
            885             890             895

Asp Leu Tyr Asp Ala Ala Lys Ala Tyr Ala Glu Gln Leu Lys Glu Asn
            900             905             910

Gly Val Ile Asn Tyr Ser Val Leu Asp Leu Thr Ala Glu Glu Leu Glu
            915             920             925

Ala Ile Lys His Gln Leu Asn Pro Lys Asp Asn Asp Val Glu Leu Gly
930             935             940

Gly Gly Gly Ser Gly Gly Gly Met Ser Arg Arg Asn Pro Cys Lys
945             950             955             960

Phe Glu Ile Arg Gly His Cys Leu Asn Gly Lys Arg Cys His Phe Ser
            965             970             975

His Asn Tyr Phe Glu Trp Pro Pro His Ala Leu Leu Val Arg Gln Asn
            980             985             990

Phe Met Leu Asn Arg Ile Leu Lys Ser Met Asp Lys Ser Ile Asp Thr
            995             1000            1005

Leu Ser Glu Ile Ser Gly Ala Ala Glu Leu Asp Arg Thr Glu Glu
    1010            1015            1020

Tyr Ala Leu Gly Val Val Gly Val Leu Glu Ser Tyr Ile Gly Ser
    1025            1030            1035

Ile Asn Asn Ile Thr Lys Gln Ser Ala Cys Val Ala Met Ser Lys
    1040            1045            1050

Leu Leu Thr Glu Leu Asn Ser Asp Asp Ile Lys Lys Leu Arg Asp
    1055            1060            1065

Asn Glu Glu Leu Asn Ser Pro Lys Ile Arg Val Tyr Asn Thr Val
    1070            1075            1080

Ile Ser Tyr Ile Glu Ser Asn Arg Lys Asn Asn Lys Gln Thr Ile
    1085            1090            1095

His Leu Leu Lys Arg Leu Pro Ala Asp Val Leu Lys Lys Thr Ile
    1100            1105            1110

Lys Asn Thr Leu Asp Ile His Lys Ser Ile Thr Ile Asn Asn Pro
    1115            1120            1125

Lys Glu Ser Thr Val Ser Asp Thr Asn Asp His Ala Lys Asn Asn
    1130            1135            1140

Asp Thr Thr
    1145